United States Patent
Hedhammar et al.

(10) Patent No.: US 9,309,299 B2
(45) Date of Patent: *Apr. 12, 2016

(54) SPIDER SILK FUSION PROTEIN STRUCTURES FOR BINDING TO AN ORGANIC TARGET

(71) Applicant: SPIBER TECHNOLOGIES AB, Uppsala (SE)

(72) Inventors: My Hedhammar, Stockholm (SE); Jan Johansson, Stockholm (SE); Anna Rising, Uppsala (SE); Per Åke Nygren, Ekerö (SE)

(73) Assignee: SPIBER TECHNOLOGIES AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/753,101

(22) Filed: Jun. 29, 2015

(65) Prior Publication Data

US 2015/0291674 A1 Oct. 15, 2015

Related U.S. Application Data

(63) Continuation of application No. 13/880,628, filed as application No. PCT/EP2011/068626 on Oct. 25, 2011, now Pat. No. 9,115,204.

(30) Foreign Application Priority Data

Oct. 27, 2010 (EP) .................................... 10189059

(51) Int. Cl.
| | |
|---|---|
| *C07K 14/435* | (2006.01) |
| *A61K 47/48* | (2006.01) |
| *B01D 15/38* | (2006.01) |
| *B01J 20/281* | (2006.01) |
| *C07K 16/06* | (2006.01) |
| *B01D 15/20* | (2006.01) |
| *C07D 495/04* | (2006.01) |
| *C07K 14/31* | (2006.01) |
| *C07K 14/76* | (2006.01) |
| *C12N 5/00* | (2006.01) |

(52) U.S. Cl.
CPC .......... *C07K 14/43518* (2013.01); *B01D 15/20* (2013.01); *C07D 495/04* (2013.01); *C07K 14/31* (2013.01); *C07K 14/76* (2013.01); *C07K 16/065* (2013.01); *C12N 5/0068* (2013.01); *C07K 2319/01* (2013.01)

(58) Field of Classification Search
None
See application file for complete search history.

(56) References Cited

U.S. PATENT DOCUMENTS

| | | | |
|---|---|---|---|
| 2005/0261479 A1 | 11/2005 | Hoffmann et al. | |
| 2009/0263430 A1 | 10/2009 | Scheibel et al. | |

FOREIGN PATENT DOCUMENTS

| | | |
|---|---|---|
| CN | 1642976 A | 7/2005 |
| CN | 101185878 A | 5/2008 |
| CN | 101190409 A | 6/2008 |
| EP | 0 704 532 A2 | 4/1996 |
| EP | 0 985 732 A2 | 3/2000 |
| EP | 2 157 099 A1 | 2/2010 |
| WO | WO 03/080655 A1 | 10/2003 |
| WO | WO 2005/111068 A2 | 11/2005 |
| WO | WO 2006/076711 A2 | 7/2006 |
| WO | WO 2007/078239 A2 | 7/2007 |
| WO | WO 2010/097385 A1 | 9/2010 |
| WO | WO 2010/123450 A1 | 10/2010 |

OTHER PUBLICATIONS

"Antibody Purification Handbook", GE Healthcare, 2007, pp. 1-164.
Bini et al., "RGD-Functionalized Bioengineered Spider Dragline Silk Biomaterial," Biomacromolecules, 2006, vol. 7, No. 11, pp. 3139-3145.
Bottomley et al., "Elution of human IgG from affinity columns containing immobilised variants of protein A," Journal of Immunological Methods, 1995, vol. 182, pp. 185-192.
Gomes et al., "Antimicrobial functionalized genetically engineered spider silk," Biomaterials, 2011, vol. 32, pp. 4255-4266.
Gülich et al., "Protein engineering of an IgG-binding domain allows milder elution conditions during affinity chromatography," Journal of Biotechnology, 2000, vol. 76, pp. 233-244.

(Continued)

*Primary Examiner* — Suzanne M Noakes
*Assistant Examiner* — Jae W Lee
(74) *Attorney, Agent, or Firm* — Birch, Stewart, Kolasch & Birch, LLP

(57) ABSTRACT

A protein structure capable of selective interaction with an organic target is provided. The protein structure is a polymer comprising as a repeating structural unit a recombinant fusion protein that is capable of selective interaction with the organic target. The fusion protein is comprising the moieties B, REP and CT, and optionally NT. B is a non-spidroin moiety of more than 30 amino acid residues, which provides the capacity of selective interaction with the organic target. REP is a moiety of from 70 to 300 amino acid residues and is derived from the repetitive fragment of a spider silk protein. CT is a moiety of from 70 to 120 amino acid residues and is derived from the C-terminal fragment of a spider silk protein. NT is an optional moiety of from 100 to 160 amino acid residues and is derived from the N-terminal fragment of a spider silk protein. The fusion protein and protein structure thereof is useful as an affinity medium and a cell scaffold material.

19 Claims, 21 Drawing Sheets

(56) References Cited

OTHER PUBLICATIONS

Hober et al., "Protein A chromatography for antibody purification," Journal of Chromatography B, 2007, vol. 848, pp. 40-74.

Huang et al., "The effect of genetically engineered spider silk-dentin matrix protein 1 chimeric protein on hydroxyapatite nucleation," Biomaterials, 2007, vol. 28, pp. 2358-2367.

International Search Report issued in PCT/EP2011/068626, mailed on Jan. 31, 2012.

Linhult et al., "Mutational analysis of the interaction between albumin-binding domain from streptococcal protein G and human serum albumin," Protein Science, 2002, vol. 11, pp. 206-213.

Nilsson et al., "Affinity Fusion Strategies for Detection, Purification, and Immobilization of Recombinant Proteins," Protein Expression and Purification, 1997, vol. 11, pp. 1-16.

Nord et al., "Binding proteins selected from combinatorial libraries of an α-helical bacterial receptor domain," Nature Biotechnology, Aug. 1997, vol. 15, pp. 772-777.

Pouchkina-Stantcheva et al., "Molecular studies of a novel dragline silk from a nursery web spider, Euprosthenops sp. (Pisauridae)," Comparative Biochemistry and Physiology, Part B, 2004, vol. 138, pp. 371-376.

Rising et al., "N-Terminal Nonrepetitive Domain Common to Dragline, Flagelliform, and Cylindriform Spider Silk Proteins," Biomacromolecules, 2006, vol. 7, pp. 3120-3124.

Rising et al., "Spider silk proteins: recent advances in recombinant production, structure-function relationships and biomedical applications," Cellular and Molecular Life Sciences, 2010.

Spiess et al., "Recombinant Spider Silk Proteins for Applications in Biomaterials," Macromolecular Bioscience, 2000, vol. 10, pp. 998-1007.

Spiess et al., "Structural characterization and functionalization of engineered spider silk films," Soft Matter, 2010, vol. 6, pp. 4168-4174.

Stark et al., "Macroscopic Fibers Self-Assembled from Recombinant Miniature Spider Silk Proteins," Biomacromolecules, 2007, vol. 8, pp. 1695-1701.

Tai, P.L. et al, "Inter-specific sequence conservation and intra-individual sequence variation in a spider silk gene," International Journal of Biological Macromolecules, 2004, vol. 34, pp. 237-243.

Thompson et al., "Clustal W: improving the sensitivity of progressive multiple sequence alignment through sequence weighting, position-specific gap penalties and weight matrix choice," Nucleic Acids Research, 1994, vol. 22, No. 22, pp. 4673-4680.

Wang et al., "Functionalization of Silk Fibroin with NeutrAvidin and Biotin," Macromolecular Bioscience, 2011, vol. 11, pp. 100-110.

Widhe et al., "Recombinant spider silk as matrices for cell culture," Biomaterials, 2010, vol. 31, pp. 9575-9585.

Wong Po Foo et al., "Novel nanocomposites from spider silk-silica fusion (chimeric) proteins," PNAS, Jun. 20, 2006, vol. 103, No. 25, pp. 9428-9433.

Wu et al., "Intracellular production of a soluble and functional monomeric streptavidin in *Escherichia coli* and its application for affinity purification of biotinylated proteins," Protein Expression and Purification, 2006, vol. 46, pp. 268-273.

| | | | | | |
|---|---|---|---|---|---|
| CThyb_Esp | SRLSSPEASS | RVSSAVSNLV | SSG-PTNSAA | LSSTISNVVS | QIGASNPGLS |
| CTnat_Eau | SRLSSPSAVS | RVSSAVSSLV | SNG-QVNMAA | LPNIISNISS | SVSASAPGAS |
| AF350266_At1 | SRLSSPGAAS | RVSSAVTSLV | SSGGPTNSAA | LSNTISNVVS | QISSSNPGLS |
| AY666062_Cm1 | SHLSSPEASS | RVSSAVSNLV | SSG-STNSAA | LPNTISNVVS | QISSSNPGLS |
| AF350273_Lg1 | SALAAPATSA | RISSHASTLL | SNG-PTNPAS | ISNVISNAVS | QISSSNPGAS |
| AY953074_Lh1 | SALSAPATSA | RISSHASALL | SSG-PTNPAS | ISNVISNAVS | QISSSNPGAS |
| AY666068_Mh1 | SHLSSPEASS | RVSSAVSNLV | SGG-STNSAA | LPNTISNVVS | QISSSNPGLS |
| U20329_Nc1 | SRLSSPQASS | RVSSAVSNLV | ASG-PTNSAA | LSSTISNVVS | QIGASNPGLS |
| AY666076_Np1 | SRLSSPEASS | RVSSAVSNLV | SSG-PTNSAA | LSNTISNVVS | QISSSNPGLS |
| AF350277_Nm1 | SRLSSPQASS | RVSSAVSNLV | ASG-PTNSAA | LSSTISNAVS | QIGASNPGLS |
| AF350279_Ns1 | SRLSSPEASS | RVSSAVSNLV | SSG-PTNSAA | LSSTISNVVS | QIGASNPGLS |
| AY666057_Ov1 | SRLSSPEASS | RVSSAVSNLV | SSG-PTNSAA | LSNTISNVVS | QISSSNPGLS |
| AY666064_Ps1 | SRLSSPEASS | RVSSAVSNLV | SSG-PTNSAA | LPNTISNVVS | QISSSNPGLS |
| AF350285_Tk1 | SLLSSPASNA | RISSAVSALA | SGA-ASGPGY | LSSVISNVVS | QVSSNSGGLV |
| AF350286_Tv1 | SRLSSPASNA | RISSAVSALA | SGG-ASSPGY | LSSIISNVVS | QVSSNNDGLS |
| ABU20328_Ab2 | SRLSSSAASS | RVSSAVSSLV | SSG-PTTPAA | LSNTISSAVS | QISASNPGLS |
| AY365016_Aam2 | -RLSSPQASS | RVSSAVSTLV | SSG-PTNPAS | LSNAIGSVVS | QVSASNPGLP |
| AF350263_Aau2 | SRLSSPQASS | RVSSAVSTLV | SSG-PTNPAA | LSNAISSVVS | QVSASNPGLS |
| AF350267_At2 | SRLSSPQASS | RVSSAVSTLV | SSG-PTNPAS | LSNAISSVVS | QVSSSNPGLS |
| AF350272_Gm2 | SRLSSPQAGA | RVSSAVSALV | ASG-PTSPAA | VSSAISNVAS | QISASNPGLS |
| AF350275_Lg2 | SALSSPTTHA | RISSHASTLL | SSG-PTNSAA | ISNVISNAVS | QVSASNPGSS |
| AY953075_Lh2 | SALSSPTTHA | RISSHASTLL | SSG-PTNAAA | LSNVISNAVS | QVSASNPGSS |
| AY654293_Nc2 | SRLASPDSGA | RVASAVSNLV | SSG-PTSSAA | LSSVISNAVS | QIGASNPGLS |
| AF350278_Nm2 | SRLASPDSGA | RVASAVSNLV | SSG-PTSSAA | LSSVISNAVS | QIGASNPGLS |
| AF350280_Ns2 | SRLASPDSGA | RVASAVSNLV | SSG-PTSSAA | LSSVIXNAVS | QIGASNPGLS |
| AF350269_DtFb1 | SRLSSPEAAS | RVSSAVSSLV | SNG-QVNVDA | LPSIISNLSS | SISASATTAS |
| AF350270_DtFb2 | SRLSSPQAAS | RVSSAVSSLV | SNG-QVNVAA | LPSIISSLSS | SISASSTAAS |
| U47853_ADF1 | SRLSSAGAAS | RVSNVAAIA | SAG----AAA | LPNVISNIYS | GVLSS--GVS |
| U47854_ADF2 | SRLSSPSAAA | RVSSAVS-LV | SNGGPTSPAA | LSSSISNVVS | QISASNPGLS |
| U47855_ADF3 | SRLSSPAASS | RVSSAVSSLV | SSG-PTKHAA | LSNTISSVVS | QVSASNPGLS |
| U47856_ADF4 | SVYLRLQPRL | RVSSAVSSLV | SSG-PTNGAA | VSGALNSLVS | QISASNPGLS |
| | | | | | |
| Consensus | SRLSSPQASS | RVSSAVSNLV | SSG-PTNSAA | LSNTISNVVS | QISASNPGLS |

Fig 1

| | |
|---|---|
| CThyb_Esp | GCDVLVQALL EVVSALIHIL GSSSIGQVNY GSAGQATQLV GQSVYQALGE F |
| CTnat_Eau | GCEVIVQALL EVITALVQIV SSSSVGYINP SAVNQITNVV ANAMAQVMG- - |
| AF350266_At1 | GCDVLVQALL EIVSALVHIL GSANIGQVNS SGVGRSASIV GQSINQAFS- - |
| AY666062_Cm1 | GCDVLVQALL EVVSALIHIL GSSSIGQVNY GSAGQATQIV ---------- - |
| AF350273_Lg1 | SCDVLVQALL ELVTALLTII GSSNVGNVNY DSSGQYAQVV SQSVQNAFV- - |
| AY953074_Lh1 | ACDVLVQALL ELVTALLTII GSSNIGSVNY DSSGQYAQVV TQSVQNVFS- - |
| AY666068_Mh1 | GCDVLVQALL EVVSALIHIL GSSSIGQVDY GSAGQATQIV GQSA------ - |
| U20329_Nc1 | GCDVLIQALL EVVSALIQIL GSSSIGQVNY GSAGQATQIV GQSVYQALG- - |
| AY666076_Np1 | GCDVLVQALL EVVSALIHIL GSSSIGQVNY GSAGQATQIV ---------- - |
| AF350277_Nm1 | GCDVLIQALL EVVSALIHIL GSSSIGQVNY GSAGQATQ-- ---------- - |
| AF350279_Ns1 | GCDVLIQALL EVVSALVHIL GSSSIGQVNY GSAGQATQ-- ---------- - |
| AY666057_Ov1 | GCDVLVQALL EVVSAPIHIL GSSSIGQVNY GSAGQATQIV ---------- - |
| AY666064_Ps1 | GCDVLVQALL EVVSALIHIL GSSSIGQVNY GSAGQATQIV ---------- - |
| AF350285_Tk1 | GCDTLVQALL EAAAALVRVL ASSSGGQVNL NTAGYTSQL- ---------- - |
| AF350286_Tv1 | GCDTVVQALL EVAAALVRVL ASSNIGQVNL NTAGYTSQL- ---------- - |
| ABU20328_Ab2 | GCDVLVQALL EVVSALVHIL GSSSVGQINY GASAQYAQMV ---------- - |
| AY365016_Aam2 | SCDVLVQALL EIVSALVHIL GSSSIGQINY SASSQYARLV GQSIAQALG- - |
| AF350263_Aau2 | GCDVLVQALL ELVSALVHIL GSSSIGQINY AAS------- ---------- - |
| AF350267_At2 | GCDVLVQALL EIVSALVHIL GSSSIGQINY AASSQYAQLV GQSLTQALG- - |
| AF350272_Gm2 | GCDVLVQALL EIVSALVSIL SSASIGQINY GASGQYAAMI ---------- - |
| AF350275_Lg2 | SCDVLVQALL ELITALISIV DSSNIGQVNY GSSGQYAQMV G--------- - |
| AY953075_Lh2 | SCDVLVQALL EIITALISIL DSSVGQVNY GSSGQYAQIV GQSMQQAMG- - |
| AY654293_Nc2 | GCDVLIQALL EIVSACVTIL SSSSIGQVNY GAASQFAQVV GQSVLSAF-- - |
| AF350278_Nm2 | GCDVLIQALL EIVSACVTIL SSSSIGQVNY GAA------- ---------- - |
| AF350280_Ns2 | GCDVLIXALL EIVSACVTIL SSSSIGQVNY GAA------- ---------- - |
| AF350269_DtFb1 | DCEVLVQVLL EVVSALVQIV CS-------- ---------- ---------- - |
| AF350270_DtFb2 | DCEVLVQVLL EIVSALVQIV SSANVGYINP EASGSLN-AV GSALAAAMG- - |
| U47853_ADF1 | SSEALIQALL EVISALIHVL GSASIGRVSS VGVNSALNAV QNAVGAYAG- - |
| U47854_ADF2 | GCDILVQALL EIISALVHIL GSANIGPVNS SSAGQSASIV GQSVYRALS- - |
| U47855_ADF3 | GCDLVQALL EVVSALVSIL GSSSIGQINY GASAQYTQMV GQSVAQALA- - |
| U47856_ADF4 | GCDALVQALL ELVSALVAIL SSASIGQVNV SSVSQSTQMI SQALS----- - |
| Consensus | GCDVLVQALL EVVSALVHIL GSSSIGQVNY GSAGQATQIV GQSVAQALGE F |

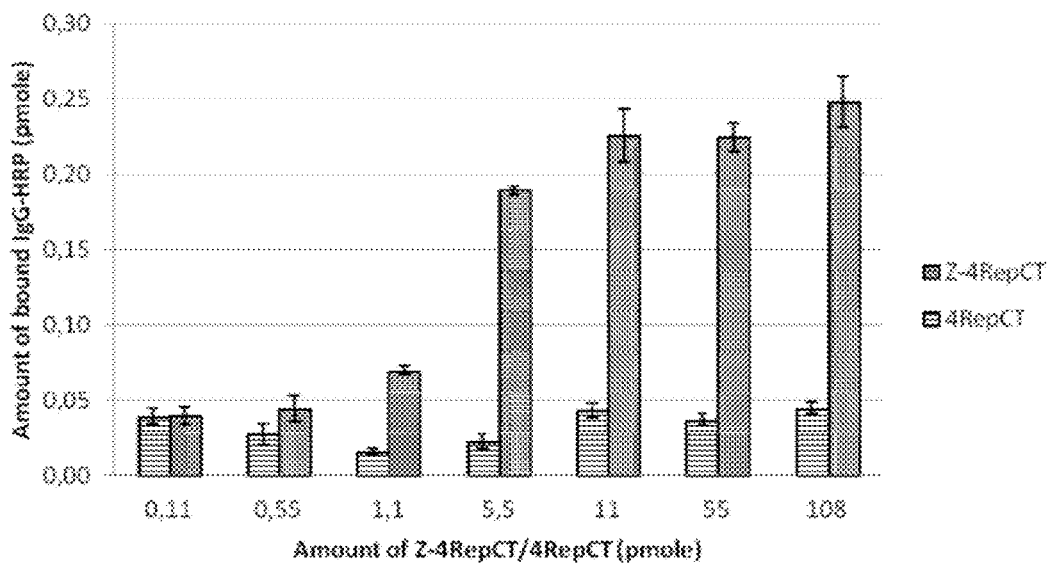
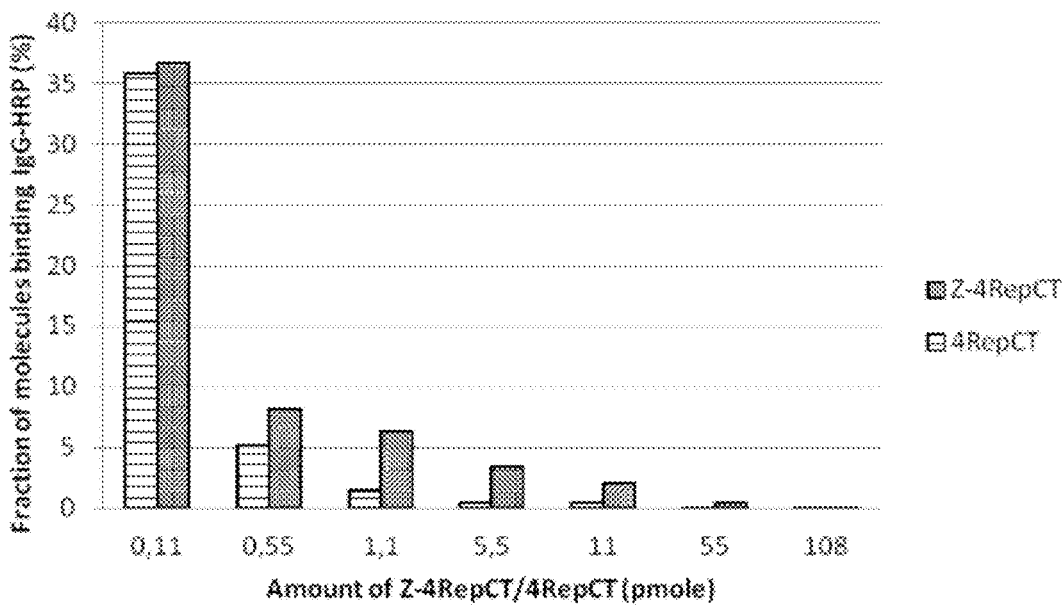
Fig 24

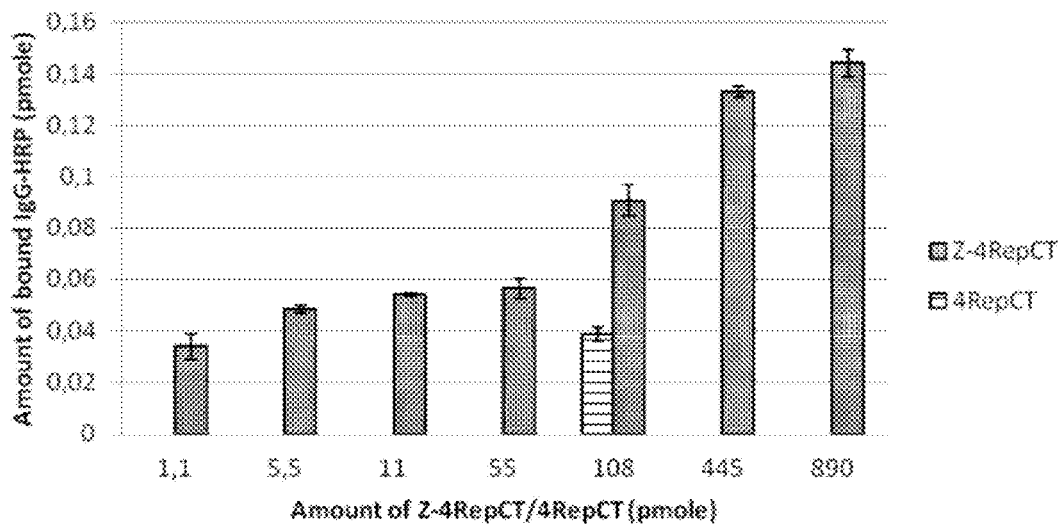
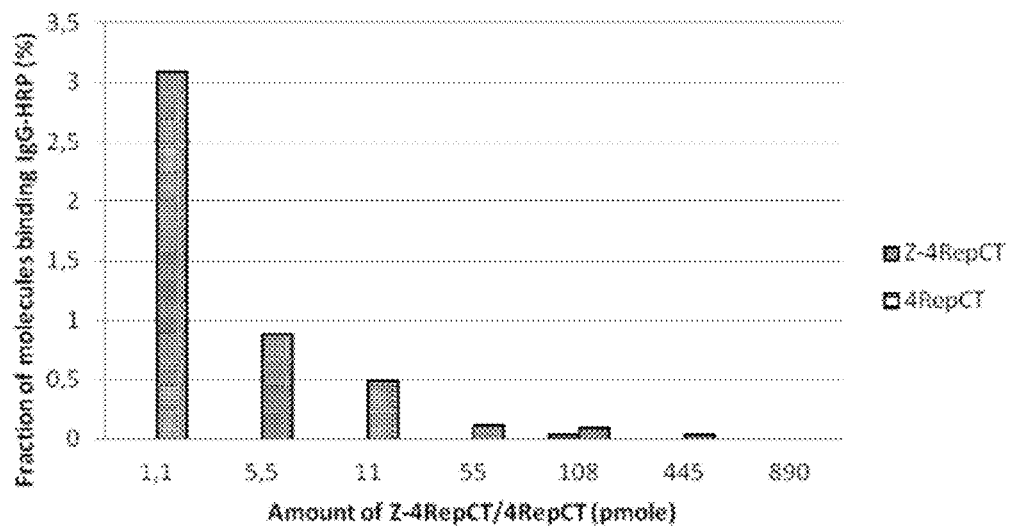
Fig 25

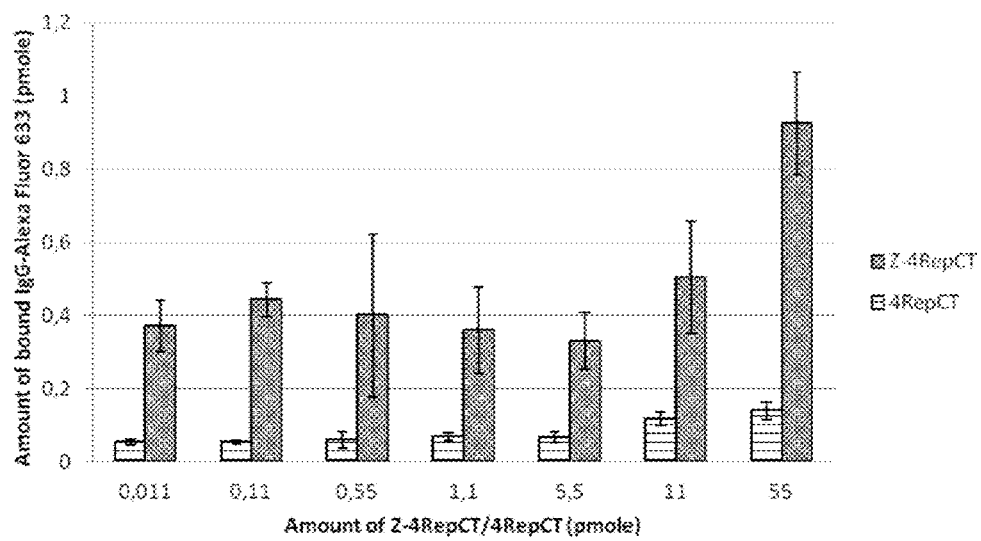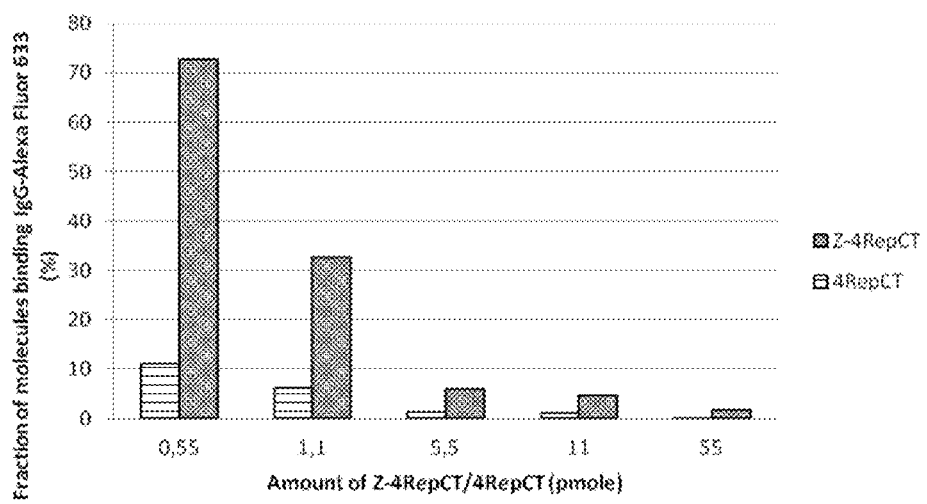
Fig 27

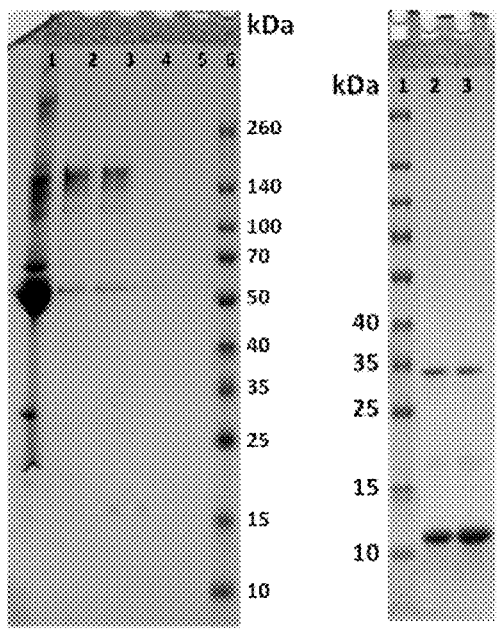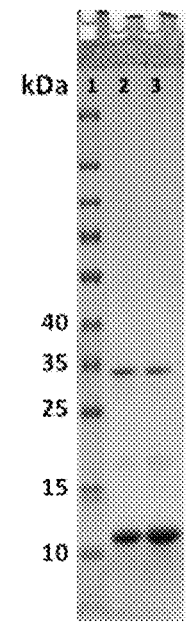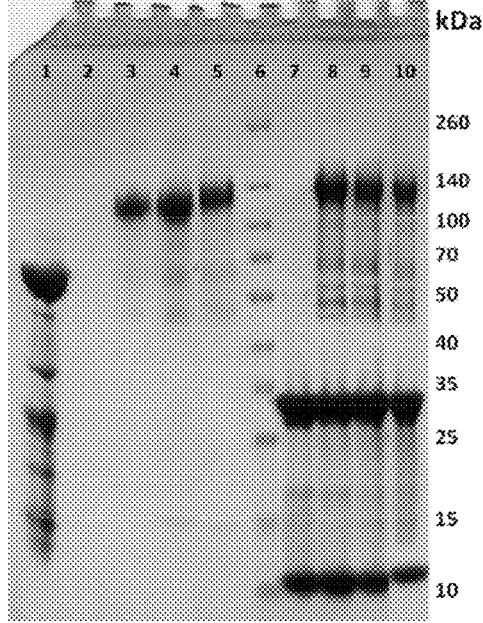
Fig 28　　　　　Fig 29　　　　　Fig 30
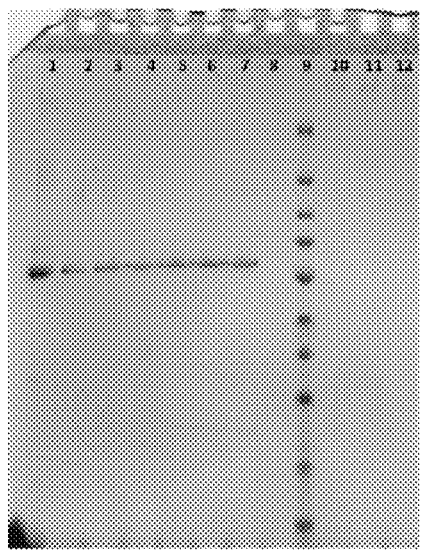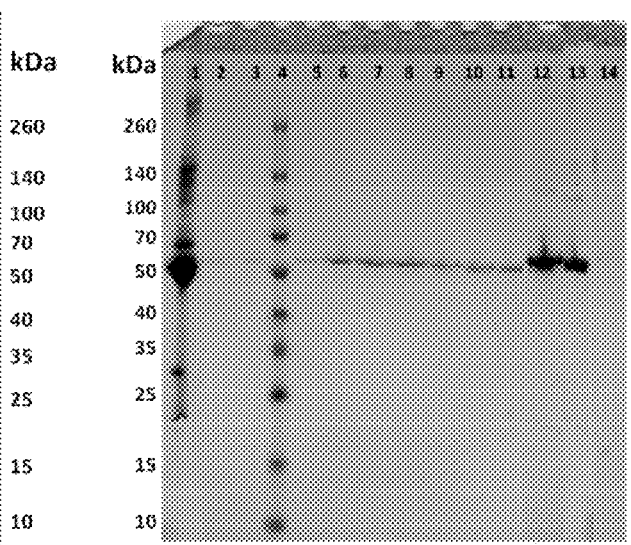
Fig 31　　　　　Fig 32

SPIDER SILK FUSION PROTEIN STRUCTURES FOR BINDING TO AN ORGANIC TARGET

This application is a Continuation of U.S. patent application Ser. No. 13/880,628 filed on Aug. 6, 2013, which is the National Phase of PCT International Application No. PCT/EP2011/068626 filed on Oct. 25, 2011 and claims priority under 35 U.S.C. §119(a) to patent application Ser. No. 10/189,059.8 filed in Europe on Oct. 27, 2010, all of which are hereby expressly incorporated by reference into the present application.

TECHNICAL FIELD OF THE INVENTION

The present invention relates to the field of recombinant fusion proteins, and more specifically to fusion proteins comprising moieties derived from spider silk proteins (spidroins). The present invention provides methods for providing a protein structure which is a polymer comprising a recombinant fusion protein, which is comprising moieties derived from spidroins. There is also provided novel protein structures for binding to an organic target.

BACKGROUND TO THE INVENTION

In applied protein chemistry, it is a common problem how to formulate or present a biologically active peptide or protein to the relevant site of activity, typically an organic target, such as a nucleic acid, a protein, a complex of proteins, or a complex of a protein(s) and/or lipids and/or carbohydrates and/or a nucleic acid(s). The simplest solution is simply to provide an aqueous solution of the biologically active peptide or protein. Many applications do however require some further means to achieve the desired goal. For instance, the peptides/proteins may be associated with a lipid mixture or chemically immobilized to a support structure.

Applications for peptides/proteins immobilized to a support structure include preparative and analytical separation procedures, such as bioprocesses, chromatography, cell capture and culture, active filters, and diagnostics. Structures based on extracellular matrix proteins, e.g. collagen, are disclosed in EP 704 532 and EP 985 732.

It has also been suggested to use spider silk proteins in a supporting structure. Spider silks are nature's high-performance polymers, obtaining extraordinary toughness and extensibility due to a combination of strength and elasticity. Spiders have up to seven different glands which produce a variety of silk types with different mechanical properties and functions. Dragline silk, produced by the major ampullate gland, is the toughest fiber. It consists of two main polypeptides, mostly referred to as major ampullate spidroin (MaSp) 1 and 2, but e.g. as ADF-3 and ADF-4 in *Araneus diadematus*. These proteins have molecular masses in the range of 200-720 kDa. Spider dragline silk proteins, or MaSps, have a tripartite composition; a non-repetitive N-terminal domain, a central repetitive region comprised of many iterated poly-Ala/Gly segments, and a non-repetitive C-terminal domain. It is generally believed that the repetitive region forms intermolecular contacts in the silk fibers, while the precise functions of the terminal domains are less clear. It is also believed that in association with fiber formation, the repetitive region undergoes a structural conversion from random coil and α-helical conformation to β-sheet structure. The C-terminal region of spidroins is generally conserved between spider species and silk types.

WO 07/078239 and Stark, M. et al., Biomacromolecules 8: 1695-1701, (2007) disclose a miniature spider silk protein consisting of a repetitive fragment with a high content of Ala and Gly and a C-terminal fragment of a protein, as well as soluble fusion proteins comprising the spider silk protein. Fibers of the spider silk protein are obtained spontaneously upon liberation of the spider silk protein from its fusion partner.

Rising, A. et al., CMLS 68(2): 169-184 (2010) reviews advances in the production of spider silk proteins.

US 2009/0263430 discloses chemical coupling of the enzyme β-galactosidase to films of a miniature spider silk protein. However, chemical coupling may require conditions which are unfavourable for protein stability and/or function. Proteins containing multiple repeats of a segment derived from the repetitive region of spider silk proteins have been designed to include a RGD cell-binding segment (Bini, E et al., Biomacromolecules 7:3139-3145 (2006)) and/or a R5 peptide (Wong Po Foo, C et al., Proc Natl Acad Sci 103 (25): 9428-9433 (2006)) or other protein segments involved in mineralization (Huang, J et al., Biomaterials 28: 2358-2367 (2007); WO 2006/076711). In these prior art documents, films are formed by solubilizing the fusion proteins in the denaturing organic solvent hexafluoroisopropanol (HFIP) and drying.

US 2005/261479 A1 discloses a method of for purification of recombinant silk proteins having an affinity tag, involving magnetic affinity separation of individual silk proteins from complex mixtures without formation of silk protein fibers or other polymer structures.

Known supporting structures and associated techniques have certain drawbacks with regard to e.g. economy, efficiency, stability, regenerating capacity, bioactivity and biocompatibility.

SUMMARY OF THE INVENTION

It is an object of the present invention to provide a novel protein structure that is capable of selective interaction with an organic target.

It is also an object of the present invention to provide a protein structure that is capable of selective interaction with an organic target, wherein the structure is formed without use of harsh solvents which may have an unpredictable effect on the secondary structure or activity of the protein and/or remain in the protein structure.

It is one object of the present invention to provide a stable protein structure that is capable of selective interaction with an organic target, which protein structure can readily be regenerated after use, e.g. with chemical treatment.

It is another object of the present invention to provide a stable protein structure that is biocompatible and suitable for cell culture and as an implant.

It is yet another object of the invention to provide a protein structure with a high density of evenly spaced functionalities that are capable of selective interaction with an organic target.

It is a further object of the invention to provide a protein structure which maintains its selective binding ability upon storage at +4° C. or at room temperature for months.

It is also an object of the invention to provide a protein structure which is autoclavable, i.e. maintains its selective binding ability after sterilizing heat treatment.

For these and other objects that will be evident from the following disclosure, the present invention provides according to a first aspect a fusion protein and a protein structure consisting of polymers comprising as a repeating structural unit the fusion protein as set out in the claims.

According to a related aspect, the present invention provides an isolated polynucleic acid encoding the fusion protein and a method of producing the fusion protein as set out in the claims.

The present invention provides according to another aspect a method for providing a protein structure as set out in the claims.

The present invention provides according to a further aspect an affinity medium as set out in the claims.

The present invention provides according to one aspect a cell scaffold material as set out in the claims. According to a related aspect, the present invention also provides a combination of cells and a cell scaffold material according to the claims.

The present invention provides according to an aspect novel uses of a protein structure and a fusion protein as set out in the claims.

The present invention provides according to another aspect a method for separation of an organic target from a sample as set out in the claims.

The present invention provides according to a further aspect a method for immobilization and optionally cultivation of cells as set out in the claims.

BRIEF DESCRIPTION OF THE DRAWINGS

FIG. 1 shows a sequence alignment of spidroin C-terminal domains.

FIG. 2 shows a sequence alignment of spidroin N-terminal domains.

FIG. 24-26 shows graphs illustrating binding of IgG-HRP to a fusion protein film comprising Z domains.

FIG. 27 shows graphs illustrating binding of IgG-Alexa Fluor 633 to a fusion protein film comprising Z domains.

FIG. 28 shows a non-reducing SDS-PAGE gel illustrating the functionality of the Z domain in a fusion protein after autoclaving.

FIG. 29 shows a SDS-PAGE gel of cleavage products from Protease 3C treatment of a fusion protein fiber comprising Z domains.

FIG. 30 shows a non-reducing SDS-PAGE gel illustrating the functionality of the Z domain in fusion protein structures formed in the presence of an organic target (IgG).

FIG. 31-32 shows non-reducing SDS-PAGE gels illustrating the functionality of the Abd domain in fusion protein structures.

Figure 3:
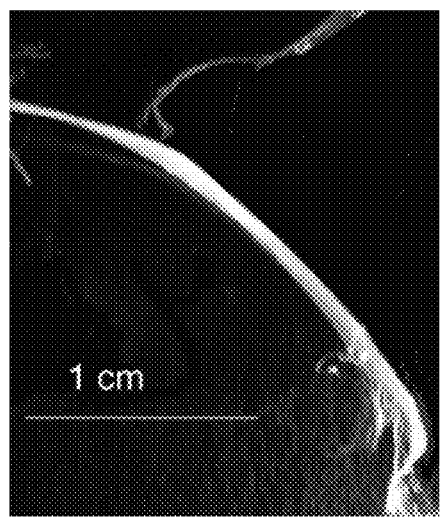
FIG. 3 shows a macroscopic fiber of a fusion protein comprising a Z domain.

| List of appended sequences | |
|---|---|
| SEQ ID NO | |
| 1 | 4Rep |
| 2 | 4RepCT |
| 3 | NT4Rep |
| 4 | NT5Rep |
| 5 | NT4RepCTHis |
| 6 | NT |
| 7 | CT |
| 8 | consensus NT sequence |
| 9 | consensus CT sequence |
| 10 | repetitive sequence from *Euprosthenops australis* MaSp1 |
| 11 | consensus G segment sequence 1 |
| 12 | consensus G segment sequence 2 |
| 13 | consensus G segment sequence 3 |
| 14 | HisZQG4Rep4CT |
| 15 | HisZQG4Rep4CT (DNA) |
| 16 | HisAbdQG4RepCT |
| 17 | HisAbdQG4RepCT (DNA) |
| 18 | HisC2QG4RepCT |
| 19 | HisC2QG4RepCT (DNA) |
| SEQ ID NO | |
| 20 | 4RepCT 2 |
| 21 | 4RepCT 2 (DNA) |
| 22 | M44RepCT |
| 23 | M44RepCT (DNA) |
| 24 | modM44RepCT |
| 25 | modM44RepCT (DNA) |
| 26 | 4RepCTM4 |
| 27 | 4RepCTM4 (DNA) |

DETAILED DESCRIPTION OF THE INVENTION

The present invention is generally based on the insight that solid protein structures capable of selective interaction with an organic target can be prepared in the form of polymers of a recombinant fusion protein as a repeating structural unit. The fusion protein is comprising at least one non-spidroin moiety of more than 30 amino acid residues that is capable of selective interaction with the organic target, and moieties corresponding to at least the repetitive and the C-terminal fragments of a spider silk protein. Surprisingly, the moieties derived from the spider silk protein can be induced to rearrange structurally and as a result form polymeric, solid structures, while the non-spidroin moiety is not structurally rearranged but maintains its desirable structure and function, i.e. capability of selective interaction with the organic target. The protein structures can be obtained without a chemical coupling step or a denaturing method step, which facilitates the procedure and improves the chances of obtaining a fusion protein with maintained functionality of its moieties, in particular when the functions are dependent on the secondary structure of the moieties. The formation of these fusion protein polymers can be tightly controlled, and this insight has been developed into further novel protein structures, methods of producing the protein structures and uses of the protein structures in various applications and methods.

The fusion protein according to the invention thus harbors both the desired selective interaction activity and an internal solid support activity that is employed in the protein structure under physiological conditions. It must be considered as surprising that the binding activity of the fusion protein is maintained although the non-spidroin moiety is covalently attached to the spidroin moiety when the latter is structurally rearranged to form polymeric, solid structures. In fact, the heat and/or chemical stability and/or binding activity of the moiety providing the selective interaction activity may be increased when integrated in a fusion protein structure according to the invention. The protein structure also provides a high and predictable density of the selective interaction activity towards an organic target. Losses of valuable protein moieties with selective interaction activity are minimized, since all expressed protein moieties are associated with the solid support.

The polymers which are formed from the fusion proteins according to the invention are solid structures and are useful for their physical properties, especially the useful combination of high strength, elasticity and light weight. A particularly useful feature is that the spidroin-derived moieties of the fusion protein are biochemically robust and suitable for regeneration, e.g. with acid, base or chaotropic agents, and suitable for heat sterilization, e.g. autoclaving at 120° C. for 20 min. The polymers are also useful for their ability to support cell adherence and growth. The properties derived from dragline silk are attractive in development of new materials for medical or technical purposes. In particular, protein structures according to the invention are useful in preparative and analytical separation procedures, such as chromatography, cell capture, selection and culture, active filters, and diagnostics. Protein structures according to the invention are also useful in medical devices, such as implants and medical products, such as wound closure systems, band-aids, sutures, wound dressings, and scaffolds for cell immobilization, cell culture, tissue engineering and guided cell regeneration.

The present invention provides a recombinant fusion protein that is capable of selective interaction with an organic target, which fusion protein is comprising the moieties B, REP and CT, and optionally NT. The present invention also provides a protein structure that is capable of selective interaction with an organic target, wherein said protein structure is a polymer comprising, and optionally consisting of, the recombinant fusion protein according to the invention, i.e. comprising, and optionally consisting of, the moieties B, REP and CT, and optionally NT.

Although the REP and the CT moieties of the fusion proteins in the examples by necessity relate to specific proteins, e.g. proteins derived from major spidroin 1 (MaSp1) from *Euprosthenops australis*, it is considered that the present disclosure is applicable to any structurally similar moieties for the purpose of producing fusion protein structures according to the invention. Furthermore, although the B moiety which provides the selective interaction activity of the fusion proteins in the examples by necessity relate to specific protein moieties, e.g. moieties derived from protein A, protein G and streptavidin, it is considered that the present disclosure is applicable to any structurally and/or functionally similar B moiety for the purpose of producing fusion protein structures according to the invention, capable of selective interaction with an organic target.

Specific fusion proteins according to the invention are defined by the formulas $B_x$—REP-$B_y$-CT-$B_z$ and $B_z$—CT-$B_y$-REP-$B_z$, wherein x, y and z are integers from 0 to 5; and x+y+z 1, optionally further containing one NT moiety at either end of the fusion protein or between any two protein moieties in the fusion protein. If x+y+z>1, i.e. if there are two or more B moieties, they may be identical or different. The two or more B moieties may have capacity of selective interaction with the same organic target or with different organic targets. It is preferred that the two or more B moieties are substantially identical, each having capacity of selective interaction with the same organic target.

In preferred fusion proteins according to the invention, x, y and z are integers from 0 to 2, preferably from 0 to 1. In certain preferred fusion proteins according to the invention, y=0. In more preferred specific fusion proteins according to the invention, y=0 and either x or z are 0, i.e. the fusion proteins are defined by the formulas $B_z$—REP-CT, $B_z$-CT-REP, REP-CT-$B_Z$ and CT-REP-$B_Z$, wherein x and z are integers from 1 to 5. In preferred fusion proteins according to the invention, y=0, x and z are integers from 0 to 1; and x+z=1. Thus, certain preferred fusion proteins according to the invention are defined by the formulas B-REP-CT, B-CT-REP, REP-CT-B and CT-REP-B. In preferred fusion proteins according to the invention, the optional NT moiety is missing.

The term "fusion protein" implies here a protein that is made by expression from a recombinant nucleic acid, i.e. DNA or RNA that is created artificially by combining two or more nucleic acid sequences that would not normally occur together (genetic engineering). The fusion proteins according to the invention are recombinant proteins, and they are therefore not identical to naturally occurring proteins. In particular, wildtype spidroins are not fusion proteins according to the invention, because they are not expressed from a recombinant nucleic acid as set out above. The combined nucleic acid sequences encode different proteins, partial proteins or polypeptides with certain functional properties. The resulting fusion protein, or recombinant fusion protein, is a single protein with functional properties derived from each of the original proteins, partial proteins or polypeptides. Furthermore, the fusion protein according to the invention and the corresponding genes are chimeric, i.e. the protein/gene moieties are derived from at least two different species. The REP and the CT moieties, as well as the optional NT moiety, are all derived from a spider silk protein. For avoidance of doubt, the B moiety according to the invention is a non-spidroin protein or polypeptide, i.e. it is not derived from a spider silk protein. In particular, the B moiety according to the invention is not derived from the C-terminal, repetitive or N-terminal fragments of a spider silk protein.

The fusion protein typically consists of from 170 to 2000 amino acid residues, such as from 170 to 1000 amino acid residues, such as from 170 to 600 amino acid residues, preferably from 170 to 500 amino acid residues, such as from 170 to 400 amino acid residues. The small size is advantageous because longer proteins containing spider silk protein fragments may form amorphous aggregates, which require use of harsh solvents for solubilisation and polymerisation. The recombinant fusion protein may contain more than 2000 residues, in particular in cases where the spider silk protein more than one B moiety and/or when it contains a NT moiety.

The terms "spidroins" and "spider silk proteins" are used interchangeably throughout the description and encompass all known spider silk proteins, including major ampullate spider silk proteins which typically are abbreviated "MaSp", or "ADF" in the case of *Araneus diadematus*. These major ampullate spider silk proteins are generally of two types, 1 and 2. These terms furthermore include non-natural proteins with a high degree of identity and/or similarity to the known spider silk proteins.

Consequently, the term "non-spidroin" implies proteins that are not derived from a spider silk protein, i.e. with a low (or no) degree of identity and/or similarity to spider silk proteins.

The protein structure according to the invention is capable of selective interaction with an organic target. This capacity resides in the fusion protein according to the invention, and more specifically in the B moiety of the fusion protein. Any interactions of the REP and the CT moieties, as well as the optional NT moiety, with organic molecules are not encompassed by the term "capable of selective interaction with an organic target". For avoidance of doubt, the term "capable of selective interaction with an organic target" does not encompass dimerization, oligomerization or polymerization of the fusion proteins according to the invention that rely on interactions involving the REP and the CT moieties, as well as the optional NT moiety.

The term "organic target" encompasses all chemical molecules containing carbon with the exception of what is traditionally considered inorganic molecules by the skilled person, e.g. carbonates, simple oxides of carbon, cyanides, diamond and graphite. For avoidance of doubt, inorganic molecules, salts and ions, such as silica and calcium chloride, are not organic. The organic target may be a complex containing or consisting of organic molecules, e.g. a receptor complex on a cell surface. The organic target may be a monomer, dimer, oligomer or polymer of one or more organic molecule types, which may be held together by covalent bonds or other types of association. It may of course also simply be a single organic molecule. Preferred organic targets according to the invention include, but are not limited to, nucleic acids, proteins and polypeptides, lipids and carbohydrates, as well as combinations thereof. Further preferred organic targets according to the invention include, but are not limited to, immunoglobulins, molecules comprising immunoglobulin or derivatives thereof, albumin, molecules comprising albumin or derivatives thereof, biotin, and molecules comprising biotin or derivatives or analogues thereof.

In the context of the present invention, "specific" or "selective" interaction of a ligand, e.g. a B moiety of the fusion protein according to the invention with its target means that the interaction is such that a distinction between specific and non-specific, or between selective and non-selective, interaction becomes meaningful. The interaction between two proteins is sometimes measured by the dissociation constant. The dissociation constant describes the strength of binding (or affinity) between two molecules. Typically the dissociation constant between an antibody and its antigen is from $10^{-7}$ to $10^{-11}$ M. However, high specificity does not necessarily require high affinity. Molecules with low affinity (in the molar range) for its counterpart have been shown to be as specific as molecules with much higher affinity. In the case of the present invention, a specific or selective interaction refers to the extent to which a particular method can be used to determine the presence and/or amount of a specific protein, the target protein or a fragment thereof, under given conditions in the presence of other proteins in a sample of a naturally occurring or processed biological or biochemical fluid. In other words, specificity or selectivity is the capacity to distinguish between related proteins. Specific and selective are sometimes used interchangeably in the present description.

The fusion protein according to the invention may also contain one or more linker peptides. The linker peptide(s) may be arranged between any moieties of the fusion protein, e.g. between the CT and REP moieties, between two B moieties, between B and CT moieties, and between B and REP moieties, or may be arranged at either terminal end of the fusion protein. If the fusion protein contains two or more B moieties, the linker peptide(s) may also be arranged in between two B moieties. The linker(s) may provide a spacer between the functional units of the fusion protein, but may also constitute a handle for identification and purification of the fusion protein, e.g. a His and/or a Trx tag. If the fusion protein contains two or more linker peptides for identification and purification of the fusion protein, it is preferred that they are separated by a spacer sequence, e.g. $His_6$-spacer-$His_6$-. The linker may also constitute a signal peptide, such as a signal recognition particle, which directs the fusion protein to the membrane and/or causes secretion of the fusion protein from the host cell into the surrounding medium. The fusion protein may also include a cleavage site in its amino acid sequence, which allows for cleavage and removal of the linker(s) and/or other relevant moieties, typically the B moiety or moieties. Various cleavage sites are known to the person skilled in the art, e.g. cleavage sites for chemical agents, such as CNBr after Met residues and hydroxylamine between Asn-Gly residues, cleavage sites for proteases, such as thrombin or protease 3C, and self-splicing sequences, such as intein self-splicing sequences.

The REP, CT and B moieties are linked directly or indirectly to one another. A direct linkage implies a direct covalent binding between the moieties without intervening sequences, such as linkers. An indirect linkage also implies that the moieties are linked by covalent bonds, but that there are intervening sequences, such as linkers and/or one or more further moieties, e.g. a NT moiety.

The B moiety or moieties may be arranged internally or at either end of the fusion protein, i.e. C-terminally arranged or N-terminally arranged. It is preferred that the B moiety or moieties are arranged at the N-terminal end of the fusion protein. If the fusion protein contains one or more linker peptide(s) for identification and purification of the fusion protein, e.g. a His or Trx tag(s), it is preferred that it is arranged at the N-terminal end of the fusion protein.

A preferred fusion protein has the form of an N-terminally arranged B moiety, coupled by a linker peptide of 1-30 amino acid residues, such as 1-10 amino acid residues, to C-terminally arranged REP and CT moieties. The linker peptide may contain a cleavage site. Optionally, the fusion protein has an N-terminal or C-terminal linker peptide, which may contain a purification tag, such as a His tag, and a cleavage site.

Another preferred fusion protein has the form of an N-terminally arranged B moiety coupled directly to C-terminally arranged REP and CT moieties. Optionally, the fusion protein has an N-terminal or C-terminal linker peptide, which may contain a purification tag, such as a His tag, and a cleavage site.

The protein structure according to the invention is a polymer comprising as a repeating structural unit recombinant fusion proteins according to the invention, which implies that it contains an ordered plurality of fusion proteins according to the invention, typically well above 100 fusion protein units, e.g. 1000 fusion protein units or more. Optionally, the polymer may comprise as a further repeating structural unit complementary proteins without a B moiety, preferably proteins derived from spider silk. This may be advantageous if the B moiety of the fusion protein is large and/or bulky. These complementary proteins typically comprise a REP moiety and a CT moiety, and optionally an NT moiety. Preferred complementary proteins according to the invention can have any of the structures set out herein with a deleted B moiety. It is preferred that the complementary fusion protein in is substantially identical to the fusion protein with a deleted B moiety. However, it is preferred that the protein structure according to the invention is a polymer consisting of recombinant fusion proteins according to the invention as a repeating structural unit, i.e. that the protein structure according to the invention is a polymer of the recombinant fusion protein according to the invention.

The magnitude of fusion units in the polymer implies that the protein structure obtains a significant size. In a preferred embodiment, the protein structure has a size of at least 0.1 µm in at least two dimensions. Thus, the term "protein structure" as used herein relates to fusion protein polymers having a thickness of at least 0.1 µm, preferably macroscopic polymers that are visible to the human eye, i.e. having a thickness of at least 1 µm. The term "protein structure" does not encompass unstructured aggregates or precipitates. While monomers of the fusion protein are water soluble, it is understood that the protein structures according to the invention are solid structures, i.e. not soluble in water. The protein structures are polymers comprising as a repeating structural unit monomers of the recombinant fusion proteins according to the invention.

It is preferable that the protein structure according to the invention is in a physical form selected from the group consisting of fiber, film, foam, net, mesh, sphere and capsule.

It is preferable that the protein structure according to the invention is a fiber or film with a thickness of at least 0.1 µm, preferably at least 1 µm. It is preferred that the fiber or film has a thickness in the range of 1-400 µm, preferably 60-120 µm. It is preferred that fibers have a length in the range of 0.5-300 cm, preferably 1-100 cm. Other preferred ranges are 0.5-30 cm and 1-20 cm. The fiber has the capacity to remain intact during physical manipulation, i.e. can be used for spinning, weaving, twisting, crocheting and similar procedures. The film is advantageous in that it is coherent and adheres to solid structures, e.g. the plastics in microtiter plates. This property of the film facilitates washing and regeneration procedures and is very useful for separation purposes. A particularly useful protein structure is a film or a fiber wherein the B moiety is the Z domain derived from staphylococcal protein A or a protein fragment having at least 70% identity thereto, see e.g. Examples 1-6.

It is also preferred that the protein structure according to the invention has a tensile strength above 1 MPa, preferably above 2 MPa, more preferably 10 MPa or higher. It is preferred that the protein structure according to the invention has a tensile strength above 100 MPa, more preferably 200 MPa or higher.

The REP moiety is a protein fragment containing from 70 to 300 amino acid residues and is derived from the repetitive fragment of a spider silk protein. This implies that the REP moiety has a repetitive character, alternating between alanine-rich stretches and glycine-rich stretches. The REP moiety generally contains more than 70, such as more than 140, and less than 300, preferably less than 240, such as less than 200, amino acid residues, and can itself be divided into several L (linker) segments, A (alanine-rich) segments and G (glycine-rich) segments, as will be explained in more detail below. Typically, said linker segments, which are optional, are located at the REP moiety terminals, while the remaining segments are in turn alanine-rich and glycine-rich. Thus, the REP moiety can generally have either of the following structures, wherein n is an integer:

$L(AG)_nL$, such as $LA_1G_1A_2G_2A_3G_3A_4G_4A_5G_5L$;
$L(AG)_nAL$, such as $LA_1G_1A_2G_2A_3G_3A_4G_4A_5G_5A_6L$;
$L(GA)_nL$, such as $LG_1A_1G_2A_2G_3A_3G_4A_4G_5A_5L$; or
$L(GA)_nGL$, such as $LG_1A_1G_2A_2G_3A_3G_4A_4G_5A_5G_6L$.

It follows that it is not critical whether an alanine-rich or a glycine-rich segment is adjacent to the N-terminal or C-terminal linker segments. It is preferred that n is an integer from 2 to 10, preferably from 2 to 8, preferably from 4 to 8, more preferred from 4 to 6, i.e. n=4, n=5 or n=6.

In preferred embodiments, the alanine content of the REP moiety according to the invention is above 20%, preferably above 25%, more preferably above 30%, and below 50%, preferably below 40%, more preferably below 35%. This is advantageous, since it is contemplated that a higher alanine content provides a stiffer and/or stronger and/or less extendible structure.

In certain embodiments, the REP moiety is void of proline residues, i.e. there are no proline residues in the REP moiety.

Now turning to the segments that constitute the REP moiety according to the invention, it shall be emphasized that each segment is individual, i.e. any two A segments, any two G segments or any two L segments of a specific REP moiety may be identical or may not be identical. Thus, it is not a general feature of the invention that each type of segment is identical within a specific REP moiety. Rather, the following disclosure provides the skilled person with guidelines how to design individual segments and gather them into a REP moiety which is thereby considered to be derived from the repetitive fragment of a spider silk protein, and which constitutes a part of a functional fusion protein according to the invention.

Each individual A segment is an amino acid sequence having from 8 to 18 amino acid residues. It is preferred that each individual A segment contains from 13 to 15 amino acid residues. It is also possible that a majority, or more than two, of the A segments contain from 13 to 15 amino acid residues, and that a minority, such as one or two, of the A segments contain from 8 to 18 amino acid residues, such as 8-12 or 16-18 amino acid residues. A vast majority of these amino acid residues are alanine residues. More specifically, from 0 to 3 of the amino acid residues are not alanine residues, and the remaining amino acid residues are alanine residues. Thus, all amino acid residues in each individual A segment are alanine residues, with no exception or the exception of one, two or three amino acid residues, which can be any amino acid. It is preferred that the alanine-replacing amino acid(s) is (are) natural amino acids, preferably individually selected from the group of serine, glutamic acid, cysteine and glycine, more preferably serine. Of course, it is possible that one or more of the A segments are all-alanine segments, while the remaining A segments contain 1-3 non-alanine residues, such as serine, glutamic acid, cysteine or glycine.

In a preferred embodiment, each A segment contains 13-15 amino acid residues, including 10-15 alanine residues and 0-3 non-alanine residues as described above. In a more preferred embodiment, each A segment contains 13-15 amino acid residues, including 12-15 alanine residues and 0-1 non-alanine residues as described above.

It is preferred that each individual A segment has at least 80%, preferably at least 90%, more preferably 95%, most preferably 100% identity to an amino acid sequence selected from the group of amino acid residues 7-19, 43-56, 71-83, 107-120, 135-147, 171-183, 198-211, 235-248, 266-279, 294-306, 330-342, 357-370, 394-406, 421-434, 458-470, 489-502, 517-529, 553-566, 581-594, 618-630, 648-661, 676-688, 712-725, 740-752, 776-789, 804-816, 840-853, 868-880, 904-917, 932-945, 969-981, 999-1013, 1028-1042 and 1060-1073 of SEQ ID NO: 10. Each sequence of this group corresponds to a segment of the naturally occurring sequence of *Euprosthenops australis* MaSp1 protein, which is deduced from cloning of the corresponding cDNA, see WO 2007/078239. Alternatively, each individual A segment has at least 80%, preferably at least 90%, more preferably 95%, most preferably 100% identity to an amino acid sequence selected from the group of amino acid residues 143-152, 174-186, 204-218, 233-247 and 265-278 of SEQ ID NO: 3. Each sequence of this group corresponds to a segment of expressed, non-natural spider silk proteins, which proteins have capacity to form silk structures under appropriate conditions. Thus, in certain embodiments according to the invention, each individual A segment is identical to an amino acid sequence selected from the above-mentioned amino acid segments. Without wishing to be bound by any particular theory, it is envisaged that A segments according to the invention form helical structures or beta sheets.

The term "% identity", as used throughout the specification and the appended claims, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). A comparison is made over the window corresponding to the shortest of the aligned sequences. The amino acid residues at each position are compared, and the percentage of positions in the query sequence that have identical correspondences in the target sequence is reported as % identity.

The term "% similarity", as used throughout the specification and the appended claims, is calculated as described for "% identity", with the exception that the hydrophobic residues Ala, Val, Phe, Pro, Leu, Ile, Trp, Met and Cys are similar; the basic residues Lys, Arg and His are similar; the acidic residues Glu and Asp are similar; and the hydrophilic, uncharged residues Gln, Asn, Ser, Thr and Tyr are similar. The remaining natural amino acid Gly is not similar to any other amino acid in this context.

Throughout this description, alternative embodiments according to the invention fulfill, instead of the specified percentage of identity, the corresponding percentage of similarity. Other alternative embodiments fulfill the specified percentage of identity as well as another, higher percentage of similarity, selected from the group of preferred percentages of identity for each sequence. For example, a sequence may be 70% similar to another sequence; or it may be 70% identical to another sequence; or it may be 70% identical and 90% similar to another sequence.

Furthermore, it has been concluded from experimental data that each individual G segment is an amino acid sequence of from 12 to 30 amino acid residues. It is preferred that each individual G segment consists of from 14 to 23 amino acid residues. At least 40% of the amino acid residues of each G segment are glycine residues. Typically the glycine content of each individual G segment is in the range of 40-60%.

It is preferred that each individual G segment has at least 80%, preferably at least 90%, more preferably 95%, most preferably 100% identity to an amino acid sequence selected from the group of amino acid residues 20-42, 57-70, 84-106, 121-134, 148-170, 184-197, 212-234, 249-265, 280-293, 307-329, 343-356, 371-393, 407-420, 435-457, 471-488, 503-516, 530-552, 567-580, 595-617, 631-647, 662-675, 689-711, 726-739, 753-775, 790-803, 817-839, 854-867, 881-903, 918-931, 946-968, 982-998, 1014-1027, 1043-1059 and 1074-1092 of SEQ ID NO: 10. Each sequence of this group corresponds to a segment of the naturally occurring sequence of *Euprosthenops australis* MaSp1 protein, which is deduced from cloning of the corresponding cDNA, see WO 2007/078239. Alternatively, each individual G segment has at least 80%, preferably at least 90%, more preferably 95%, most preferably 100% identity to an amino acid sequence selected from the group of amino acid residues 153-173, 187-203, 219-232, 248-264 and 279-296 of SEQ ID NO: 3. Each sequence of this group corresponds to a segment of expressed, non-natural spider silk proteins, which proteins have capacity to form silk structures under appropriate conditions. Thus, in certain embodiments according to the invention, each individual G segment is identical to an amino acid sequence selected from the above-mentioned amino acid segments.

In certain embodiments, the first two amino acid residues of each G segment according to the invention are not -Gln-Gln-.

There are the three subtypes of the G segment according to the invention. This classification is based upon careful analysis of the *Euprosthenops australis* MaSp1 protein sequence (WO 2007/078239), and the information has been employed and verified in the construction of novel, non-natural spider silk proteins.

The first subtype of the G segment according to the invention is represented by the amino acid one letter consensus sequence GQG(G/S)QGG(Q/Y)GG (L/Q)GQGGYGQGA GSS (SEQ ID NO: 11). This first, and generally the longest, G segment subtype typically contains 23 amino acid residues, but may contain as little as 17 amino acid residues, and lacks charged residues or contain one charged residue. Thus, it is preferred that this first G segment subtype contains 17-23 amino acid residues, but it is contemplated that it may contain as few as 12 or as many as 30 amino acid residues. Without wishing to be bound by any particular theory, it is envisaged that this subtype forms coil structures or $3_1$-helix structures. Representative G segments of this first subtype are amino acid residues 20-42, 84-106, 148-170, 212-234, 307-329, 371-393, 435-457, 530-552, 595-617, 689-711, 753-775, 817-839, 881-903, 946-968, 1043-1059 and 1074-1092 of SEQ ID NO: 10. In certain embodiments, the first two amino acid residues of each G segment of this first subtype according to the invention are not -Gln-Gln-.

The second subtype of the G segment according to the invention is represented by the amino acid one letter consensus sequence GQGGQGQG(G/R)Y GQG(A/S)G(S/G)S (SEQ ID NO: 12). This second, generally mid-sized, G segment subtype typically contains 17 amino acid residues and lacks charged residues or contain one charged residue. It is preferred that this second G segment subtype contains 14-20 amino acid residues, but it is contemplated that it may contain as few as 12 or as many as 30 amino acid residues. Without wishing to be bound by any particular theory, it is envisaged that this subtype forms coil structures. Representative G segments of this second subtype are amino acid residues 249-265, 471-488, 631-647 and 982-998 of SEQ ID NO: 10; and amino acid residues 187-203 of SEQ ID NO: 3.

The third subtype of the G segment according to the invention is represented by the amino acid one letter consensus sequence G(R/Q)GQG(G/R)YGQG (A/S/V)GGN (SEQ ID NO: 13). This third G segment subtype typically contains 14 amino acid residues, and is generally the shortest of the G segment subtypes according to the invention. It is preferred that this third G segment subtype contains 12-17 amino acid residues, but it is contemplated that it may contain as many as 23 amino acid residues. Without wishing to be bound by any particular theory, it is envisaged that this subtype forms turn structures. Representative G segments of this third subtype are amino acid residues 57-70, 121-134, 184-197, 280-293, 343-356, 407-420, 503-516, 567-580, 662-675, 726-739, 790-803, 854-867, 918-931, 1014-1027 of SEQ ID NO: 10; and amino acid residues 219-232 of SEQ ID NO: 3.

Thus, in preferred embodiments, each individual G segment has at least 80%, preferably 90%, more preferably 95%, identity to an amino acid sequence selected from SEQ ID NO: 11, SEQ ID NO: 12 and SEQ ID NO: 13.

In a preferred embodiment of the alternating sequence of A and G segments of the REP moiety, every second G segment is of the first subtype, while the remaining G segments are of the third subtype, e.g. . . . $A_1G_{short}A_2G_{long}A_3 G_{short}A_4G_{long}A_5G_{short}$ . . . . In another preferred embodiment of the REP moiety, one G segment of the second subtype interrupts the G segment regularity via an insertion, e.g. . . . $A_1G_{short}A_2G_{long}A_3G_{mid}A_4G_{short}A_5G_{long}$ . . . .

Each individual L segment represents an optional linker amino acid sequence, which may contain from 0 to 20 amino acid residues, such as from 0 to 10 amino acid residues. While this segment is optional and not functionally critical for the spider silk protein, its presence still allows for fully functional spider silk fusion proteins, forming protein structures according to the invention. There are also linker amino acid sequences present in the repetitive part (SEQ ID NO: 10) of the deduced amino acid sequence of the MaSp1 protein from *Euprosthenops australis*. In particular, the amino acid sequence of a linker segment may resemble any of the described A or G segments, but usually not sufficiently to meet their criteria as defined herein.

As shown in WO 2007/078239, a linker segment arranged at the C-terminal part of the REP moiety can be represented by the amino acid one letter consensus sequences ASASAAASAA STVANSVS and ASAASAAA, which are rich in alanine. In fact, the second sequence can be considered to be an A segment according to the invention, while the first sequence has a high degree of similarity to A segments according to the invention. Another example of a linker segment according the invention has the one letter amino acid sequence GSAMGQGS, which is rich in glycine and has a high degree of similarity to G segments according to the invention. Another example of a linker segment is SASAG.

Representative L segments are amino acid residues 1-6 and 1093-1110 of SEQ ID NO: 10; and amino acid residues 138-142 of SEQ ID NO: 3, but the skilled person in the art will readily recognize that there are many suitable alternative amino acid sequences for these segments. In one embodiment of the REP moiety according to the invention, one of the L segments contains 0 amino acids, i.e. one of the L segments is void. In another embodiment of the REP moiety according to the invention, both L segments contain 0 amino acids, i.e. both L segments are void. Thus, these embodiments of the REP moieties according to the invention may be schematically represented as follows: $(AG)_nL$, $(AG)_nAL$, $(GA)_nL$, $(GA)_nGL$; $L(AG)_n$, $L(AG)_nA$, $L(GA)_n$, $L(GA)_nG$; and $(AG)_n$, $(AG)_nA$, $(GA)_n$, $(GA)_nG$. Any of these REP moieties are suitable for use with any CT moiety as defined below.

The CT moiety is a protein fragment containing from 70 to 120 amino acid residues and is derived from the C-terminal fragment of a spider silk protein. The expression "derived from" implies in the context of the CT moiety according to the invention that it has a high degree of similarity to the C-terminal amino acid sequence of spider silk proteins. As shown in FIG. 1, this amino acid sequence is well conserved among various species and spider silk proteins, including MaSp1 and MaSp2. A consensus sequence of the C-terminal regions of MaSp1 and MaSp2 is provided as SEQ ID NO: 9. In FIG. 1, the following MaSp proteins are aligned, denoted with Gen-Bank accession entries where applicable:

TABLE 1

| Spidroin CT moieties | |
|---|---|
| Species and spidroin protein | Entry |
| *Euprosthenops* sp MaSp1 (Pouchkina-Stantcheva, N N & McQueen-Mason, S J, ibid) | Cthyb_Esp |
| *Euprosthenops australis* MaSp1 | CTnat_Eau |
| *Argiope trifasciata* MaSp1 | AF350266_At1 |
| *Cyrtophora moluccensis* Sp1 | AY666062_Cm1 |
| *Latrodectus geometricus* MaSp1 | AF350273_Lg1 |
| *Latrodectus hesperus* MaSp1 | AY953074_Lh1 |
| *Macrothele holsti* Sp1 | AY666068_Mh1 |
| *Nephila clavipes* MaSp1 | U20329_Nc1 |
| *Nephila pilipes* MaSp1 | AY666076_Np1 |
| *Nephila madagascariensis* MaSp1 | AF350277_Nm1 |
| *Nephila senegalensis* MaSp1 | AF350279_Ns1 |
| *Octonoba varians* Sp1 | AY666057_Ov1 |
| *Psechrus sinensis* Sp1 | AY666064_Ps1 |
| *Tetragnatha kauaiensis* MaSp1 | AF350285_Tk1 |
| *Tetragnatha versicolor* MaSp1 | AF350286_Tv1 |
| *Araneus bicentenarius* Sp2 | ABU20328_Ab2 |
| *Argiope amoena* MaSp2 | AY365016_Aam2 |
| *Argiope aurantia* MaSp2 | AF350263_Aau2 |
| *Argiope trifasciata* MaSp2 | AF350267_At2 |
| *Gasteracantha mammosa* MaSp2 | AF350272_Gm2 |
| *Latrodectus geometricus* MaSp2 | AF350275_Lg2 |
| *Latrodectus hesperus* MaSp2 | AY953075_Lh2 |
| *Nephila clavipes* MaSp2 | AY654293_Nc2 |
| *Nephila madagascariensis* MaSp2 | AF350278_Nm2 |
| *Nephila senegalensis* MaSp2 | AF350280_Ns2 |
| *Dolomedes tenebrosus* Fb1 | AF350269_DtFb1 |
| *Dolomedes tenebrosus* Fb2 | AF350270_DtFb2 |
| *Araneus diadematus* ADF-1 | U47853_ADF1 |
| *Araneus diadematus* ADF-2 | U47854_ADF2 |
| *Araneus diadematus* ADF-3 | U47855_ADF3 |
| *Araneus diadematus* ADF-4 | U47856_ADF4 |

It is not critical which specific CT moiety is present in spider silk proteins according to the invention, as long as the CT moiety is not entirely missing. Thus, the CT moiety according to the invention can be selected from any of the amino acid sequences shown in FIG. 1 and Table 1 or sequences with a high degree of similarity. A wide variety of C-terminal sequences can be used in the spider silk protein according to the invention.

The sequence of the CT moiety according to the invention has at least 50% identity, preferably at least 60%, more preferably at least 65% identity, or even at least 70% identity, to the consensus amino acid sequence SEQ ID NO: 9, which is based on the amino acid sequences of FIG. 1.

A representative CT moiety according to the invention is the *Euprosthenops australis* sequence SEQ ID NO: 7, Thus, according to a preferred aspect of the invention, the CT moiety has at least 80%, preferably at least 90%, such as at least 95%, identity to SEQ ID NO: 7 or any individual amino acid sequence of FIG. 1 and Table 1. In preferred aspects of the invention, the CT moiety is identical to SEQ ID NO: 7 or any individual amino acid sequence of FIG. 1 and Table 1.

The CT moiety typically consists of from 70 to 120 amino acid residues. It is preferred that the CT moiety contains at least 70, or more than 80, preferably more than 90, amino acid residues. It is also preferred that the CT moiety contains at most 120, or less than 110 amino acid residues. A typical CT moiety contains approximately 100 amino acid residues.

The optional NT moiety is a protein fragment containing from 100 to 160 amino acid residues and is derived from the N-terminal fragment of a spider silk protein. The expression "derived from" implies in the context of the NT moiety according to the invention that it has a high degree of similarity to the N-terminal amino acid sequence of spider silk proteins. As shown in FIG. 2, this amino acid sequence is well conserved among various species and spider silk proteins, including MaSp1 and MaSp2. In FIG. 2, the following spidroin NT moieties are aligned, denoted with Gen Bank accession entries where applicable:

TABLE 2

Spidroin NT moieties

| Code | Species and spidroin protein | GenBank acc. no. |
|---|---|---|
| Ea MaSp1 | *Euprosthenops australis* MaSp 1 | AM259067 |
| Lg MaSp1 | *Latrodectus geometricus* MaSp 1 | ABY67420 |
| Lh MaSp1 | *Latrodectus hesperus* MaSp 1 | ABY67414 |
| Nc MaSp1 | *Nephila clavipes* MaSp 1 | ACF19411 |
| At MaSp2 | *Argiope trifasciata* MaSp 2 | AAZ15371 |
| Lg MaSp2 | *Latrodectus geometricus* MaSp 2 | ABY67417 |
| Lh MaSp2 | *Latrodectus hesperus* MaSp 2 | ABR68855 |
| Nim MaSp2 | *Nephila inaurata madagascariensis* MaSp 2 | AAZ15322 |
| Nc MaSp2 | *Nephila clavipes* MaSp 2 | ACF19413 |
| Ab CySp1 | *Argiope bruennichi* cylindriform spidroin 1 | BAE86855 |
| Ncl CySp1 | *Nephila clavata* cylindriform spidroin 1 | BAE54451 |
| Lh TuSp1 | *Latrodectus hesperus* tubuliform spidroin | ABD24296 |
| Nc Flag | *Nephila clavipes* flagelliform silk protein | AF027972 |
| Nim Flag | *Nephila inaurata madagascariensis* flagelliform silk protein | AF218623 (translated) |

Only the part corresponding to the N-terminal moiety is shown for each sequence, omitting the signal peptide. Nc flag and Nlm flag are translated and edited according to Rising A. et al. Biomacromolecules 7, 3120-3124 (2006)).

It is not critical which specific NT moiety is present in spider silk proteins according to the invention. Thus, the NT moiety according to the invention can be selected from any of the amino acid sequences shown in FIG. 2 or sequences with a high degree of similarity. A wide variety of N-terminal sequences can be used in the spider silk protein according to the invention. Based on the homologous sequences of FIG. 2, the following sequence constitutes a consensus NT amino acid sequence:

(SEQ ID NO: 8)
QANTPWSSPNLADAFINSF(M/L)SA(A/I)SSSGAFSADQLDDMSTIG (D/N/Q)TLMSAMD(N/S/K)MGRSG(K/R)STKSKLQALNMAFASSMA

EIAAAESGG(G/Q)SVGVKTNAISDALSSAFYQTTGSVNPQFV(N/S)E

IRSLI(G/N)M(F/L)(A/S)QASANEV.

The sequence of the NT moiety according to the invention has at least 50% identity, preferably at least 60% identity, to the consensus amino acid sequence SEQ ID NO: 8, which is based on the amino acid sequences of FIG. 2. In a preferred embodiment, the sequence of the NT moiety according to the invention has at least 65% identity, preferably at least 70% identity, to the consensus amino acid sequence SEQ ID NO: 8. In preferred embodiments, the NT moiety according to the invention has furthermore 70%, preferably 80%, similarity to the consensus amino acid sequence SEQ ID NO: 8.

A representative NT moiety according to the invention is the *Euprosthenops australis* sequence SEQ ID NO: 6. According to a preferred embodiment of the invention, the NT moiety has at least 80% identity to SEQ ID NO: 6 or any individual amino acid sequence in FIG. 1. In preferred embodiments of the invention, the NT moiety has at least 90%, such as at least 95% identity, to SEQ ID NO: 6 or any individual amino acid sequence in FIG. 2. In preferred embodiments of the invention, the NT moiety is identical to SEQ ID NO: 6 or any individual amino acid sequence in FIG. 1, in particular to Ea MaSp1.

The NT moiety contains from 100 to 160 amino acid residues. It is preferred that the NT moiety contains at least 100, or more than 110, preferably more than 120, amino acid residues. It is also preferred that the NT moiety contains at most 160, or less than 140 amino acid residues. A typical NT moiety contains approximately 130-140 amino acid residues.

The B moiety is a protein or polypeptide fragment comprising more than 30 amino acid residues. The B moiety is preferably comprising more than 40 amino acid residues, such as more than 50 amino acid residues. The B moiety is preferably comprising less than 500 amino acid residues, such as less than 200 amino acid residues, more preferably less than 100 amino acid residues, such as less than 100 amino acid residues. It is capable of selective interaction with the organic target, and it is the B moiety in the fusion protein which provides the capacity of selective interaction with the organic target.

The B moiety is a non-spidroin moiety. This implies that it is not derived from a spider silk protein, i.e. it has a low (or no) degree of identity and/or similarity to spider silk proteins. The sequence of the B moiety according to the invention preferably has less than 30% identity, such as less than 20% identity, preferably less than 10% identity, to any of the spidroin amino acid sequences disclosed herein, and specifically to any of SEQ ID NO: 6-10.

It is regarded as within the capabilities of those of ordinary skill in the art to select the B moiety. Nevertheless, examples of affinity ligands that may prove useful as B moieties, as well as examples of formats and conditions for detection and/or quantification, are given below for the sake of illustration.

The biomolecular diversity needed for selection of affinity ligands may be generated by combinatorial engineering of one of a plurality of possible scaffold molecules, and specific and/or selective affinity ligands are then selected using a suitable selection platform. Non-limiting examples of such structures, useful for generating affinity ligands against the organic target, are staphylococcal protein A and domains thereof and derivatives of these domains, such as the Z domain (Nord K et al. (1997) Nat. Biotechnol. 15:772-777); lipocalins (Beste G et al. (1999) Proc. Natl. Acad. Sci. U.S.A. 96:1898-1903); ankyrin repeat domains (Binz H K et al. (2003) J. Mol. Biol. 332:489-503); cellulose binding domains (CBD) (Smith G P et al. (1998) J. Mol. Biol. 277:317-332; Lehtiö J et al. (2000) Proteins 41:316-322); γ crystallines (Fiedler U and Rudolph R, WO01/04144); green fluorescent protein (GFP) (Peelle B et al. (2001) Chem. Biol. 8:521-534); human cytotoxic T lymphocyte-associated antigen 4 (CTLA-4) (Hufton S E et al. (2000) FEBS Lett. 475:225-231; Irving R A et al. (2001) J. Immunol. Meth. 248:31-45); protease inhibitors, such as Knottin proteins (Wentzel A et al. (2001) J. Bacteriol. 183:7273-7284; Baggio R et al. (2002) J. Mol. Recognit. 15:126-134) and Kunitz domains (Roberts B L et al. (1992) Gene 121:9-15; Dennis M S and Lazarus R A (1994) J. Biol. Chem. 269:22137-22144); PDZ domains (Schneider S et al. (1999) Nat. Biotechnol. 17:170-175); peptide aptamers, such as thioredoxin (Lu Z et al. (1995) Biotechnology 13:366-372; Klevenz B et al. (2002) Cell. Mol. Life Sci. 59:1993-1998); staphylococcal nuclease (Norman T C et al. (1999) Science 285:591-595); tendamistats (McConell S J and Hoess R H (1995) J. Mol. Biol. 250:460-479; Li R et al. (2003) Protein Eng. 16:65-72); trinectins based on the fibronectin type III domain (Koide A et al. (1998) J. Mol. Biol. 284:1141-1151; Xu L et al. (2002) Chem. Biol. 9:933-942); and zinc fingers (Bianchi E et al. (1995) J. Mol. Biol. 247: 154-160; Klug A (1999) J. Mol. Biol. 293:215-218; Segal D J et al. (2003) Biochemistry 42:2137-2148).

The above-mentioned examples include scaffold proteins presenting a single randomized loop used for the generation of novel binding specificities, protein scaffolds with a rigid secondary structure where side chains protruding from the protein surface are randomized for the generation of novel binding specificities, and scaffolds exhibiting a non-contiguous hyper-variable loop region used for the generation of novel binding specificities.

Oligonucleotides may also be used as affinity ligands. Single stranded nucleic acids, called aptamers or decoys, fold into well-defined three-dimensional structures and bind to their target with high affinity and specificity. (Ellington A D and Szostak J W (1990) Nature 346:818-822; Brody E N and Gold L (2000) J. Biotechnol. 74:5-13; Mayer G and Jenne A (2004) BioDrugs 18:351-359). The oligonucleotide ligands can be either RNA or DNA and can bind to a wide range of target molecule classes.

For selection of the desired affinity ligand from a pool of variants of any of the scaffold structures mentioned above, a number of selection platforms are available for the isolation of a specific novel ligand against a target protein of choice. Selection platforms include, but are not limited to, phage display (Smith G P (1985) Science 228:1315-1317), ribosome display (Hanes J and Plückthun A (1997) Proc. Natl. Acad. Sci. U.S.A. 94:4937-4942), yeast two-hybrid system (Fields S and Song 0 (1989) Nature 340:245-246), yeast display (Gai S A and Wittrup K D (2007) Curr Opin Struct Biol 17:467-473), mRNA display (Roberts R W and Szostak J W (1997) Proc. Natl. Acad. Sci. U.S.A. 94:12297-12302), bacterial display (Daugherty P S (2007) Curr Opin Struct Biol 17:474-480, Kronqvist N et al. (2008) Protein Eng Des Sel 1-9, Harvey B R et al. (2004) PNAS 101(25):913-9198), microbead display (Nord O et al. (2003) J Biotechnol 106:1-13, WO01/05808), SELEX (System Evolution of Ligands by Exponential Enrichment) (Tuerk C and Gold L (1990) Science 249:505-510) and protein fragment complementation assays (PCA) (Remy I and Michnick S W (1999) Proc. Natl. Acad. Sci. U.S.A. 96:5394-5399). A preferred group of B moieties with affinity for immunoglobulins, albumin or other organic targets are bacterial receptin domains or derivatives thereof.

A group of preferred B moieties are capable of selective interaction with immunoglobulins and molecules comprising immunoglobulin or derivatives thereof. A preferred group of immunoglobulin subclasses are the subclasses that are recognized by the Z domain derived from staphylococcal protein A, i.e. IgG1, IgG2, IgG4, IgA and IgM from human, all Ig subclasess from rabbit and cow, IgG1 and IgG2 from guinea pig, and IgG1, IgG2a, IgG2b, IgG3 and IgM from mouse (see Hober, S. et al., J. Chromatogr B. 848:40-47 (2007)), more preferably the immunoglobulin subclasses IgG1, IgG2, IgG4, IgA and IgM from human. Another preferred group of immunoglobulin subclasses are the subclasses that are recognized by the C2 domain streptococcal protein G; i.e. all human subclasses of IgG, including IgG3, and IgG from several animals, including mouse, rabbit and sheep.

One group of preferred B moieties are selected from the group consisting of the Z domain derived from staphylococcal protein A, staphylococcal protein A and domains thereof, preferably the E, D, A, B and C domains, streptococcal protein G and domains thereof, preferably the C1, C2 and C3 domains; and protein fragments having at least 70% identity, such as at least 80% identity, or at least 90% identity, to any of these amino acid sequences. Preferably, the B moiety is selected from the group consisting of the Z domain derived from staphylococcal protein A, the B domain of staphylococcal protein A, and the C2 domain of streptococcal protein G; and protein fragments having at least 70% identity, such as at least 80% identity, or at least 90% identity, to any of these amino acid sequences. Preferably, the B moiety is selected from the group consisting of the Z domain derived from staphylococcal protein A and protein fragments having at least 70% identity, such as at least 80% identity, or at least 90% identity, to this amino acid sequence. It is preferred that the B moiety is selected from the group consisting of the Z domain derived from staphylococcal protein A and the C2 domain of streptococcal protein G, see e.g. Examples 1-6 and 8. A preferred group of B moieties with affinity for immunoglobulins are bacterial receptin domains or derivatives thereof.

Another group of preferred B moieties are capable of selective interaction with albumin and molecules comprising albumin or derivatives thereof. A preferred group of B moieties with affinity for albumin are bacterial receptin domains or derivatives thereof. Preferred B moieties are selected from streptococcal protein G, the albumin-binding domain of streptococcal protein G, GA modules from *Finegoldia magna*; and protein fragments having at least 70% identity, such as at least 80% identity, or at least 90% identity, to any of these amino acid sequences. Preferably, the B moiety is selected from the albumin-binding domain of streptococcal protein G and protein fragments having at least 70% identity, such as at least 80% identity, or at least 90% identity, thereto. It is preferred that the B moiety is the albumin-binding domain of streptococcal protein G see e.g. Example 7.

A further group of preferred B moieties are capable of selective interaction with biotin and molecules comprising biotin or derivatives or analogues thereof. Preferred B moieties are selected from the group consisting of streptavidin, monomeric streptavidin (M4); and protein fragments having at least 70% identity, such as at least 80% identity, or at least 90% identity to any of these amino acid sequences. It is preferred that the B moiety is monomeric streptavidin (M4) see e.g. Examples 10-12.

Specific fusion proteins and protein structures according to the invention are provided in the Examples. These preferred fusion proteins form the group consisting of SEQ ID NOS 14, 16, 18, 22, 24 and 26. Further preferred fusion proteins are having at least 80%, preferably at least 90%, more preferably at least 95%, identity to any of these sequences.

The present invention further provides isolated polynucleic acids encoding a fusion protein according to the invention. In particular, specific polynucleic acids are provided in the Examples and the appended sequence listing, e.g. SEQ ID NOS 15, 17, 19, 23, 25 and 27. Further preferred polynucleic acids encode fusion proteins having at least 80%, preferably at least 90%, more preferably at least 95%, identity to any of SEQ ID NOS 14, 16, 18, 22, 24 and 26.

The polynucleic acids according to the invention are useful for producing the fusion proteins according to the invention. The present invention provides a method of producing a fusion protein. The first step involves expressing in a suitable host a fusion protein according to the invention. Suitable hosts are well known to a person skilled in the art and include e.g. bacteria and eukaryotic cells, such as yeast, insect cell lines and mammalian cell lines. Typically, this step involves expression of a polynucleic acid molecule which encodes the fusion protein in *E. coli*.

The second method step involves obtaining a mixture containing the fusion protein. The mixture may for instance be obtained by lysing or mechanically disrupting the host cells. The mixture may also be obtained by collecting the cell culture medium, if the fusion protein is secreted by the host cell. The thus obtained protein can be isolated using standard procedures. If desired, this mixture can be subjected to centrifugation, and the appropriate fraction (precipitate or supernatant) be collected. The mixture containing the fusion protein can also be subjected to gel filtration, chromatography, e.g. anion exchange chromatography, dialysis, phase separation or filtration to cause separation. Optionally, lipopolysaccharides and other pyrogens are actively removed at this stage. If desired, linker peptides may be removed by cleavage in this step.

Proteins structures according to the invention are assembled spontaneously from the fusion proteins according to the invention under suitable conditions, and the assembly into polymers is promoted by the presence of shearing forces and/or an interface between two different phases e.g. between a solid and a liquid phase, between air and a liquid phase or at a hydrophobic/hydrophilic interface, e.g. a mineral oil-water interface. The presence of the resulting interface stimulates polymerization at the interface or in the region surrounding the interface, which region extends into the liquid medium, such that said polymerizing initiates at said interface or in said interface region. Various protein structures can be produced by adapting the conditions during the assembly. For instance, if the assembly is allowed to occur in a container that is gently wagged from side to side, a fiber is formed at the air-water interface. If the mixture is allowed to stand still, a film is formed at the air-water interface. If the mixture is evaporated, a film is formed at the bottom of the container. If oil is added on top of the aqueous mixture, a film is formed at the oil-water interface, either if allowed to stand still or if wagged. If the mixture is foamed, e.g. by bubbling of air or whipping, the foam is stable and solidifies if allowed to dry.

The present invention thus provides a method for providing a protein structure displaying a binding activity towards an organic target. In the first method step, there is provided a recombinant fusion protein according to the invention. The fusion protein may e.g. be provided by expressing it in a suitable host from a polynucleic acid according to the invention. In the second method step, the fusion protein is subjected to conditions to achieve formation of a polymer comprising the recombinant fusion protein. Notably, although the spontaneously assembled protein structures can be solubilized in hexafluoroisopropanol, the solubilized fusion proteins are then not able to spontaneously reassemble into e.g. fibers.

The protein structure is useful as part of an affinity medium for immobilization of an organic target, wherein the B moiety is capable of selective interaction with the organic target. A sample, e.g. a biological sample, may be applied to a fusion protein or a protein structure according to the invention which is capable of binding to an organic target present in the biological sample, and the fusion protein or protein structure is then useful in separation of the organic target from the sample. A biological sample, such as blood, serum or plasma which has been removed from a subject may be subjected to detection, separation and/or quantification of the organic target.

The present invention thus provides a method for separation of an organic target from a sample. A sample, e.g. a biological sample such as blood, serum or plasma, containing the organic target is provided. The biological sample may be an earlier obtained sample. If using an earlier obtained sample in a method, no steps of the method are practiced on the human or animal body.

An affinity medium according to the invention is provided, comprising a fusion protein or a protein structure according to the invention. In certain embodiments, the affinity medium is consisting of the fusion protein or protein structure according to the invention. The affinity medium is capable of selective interaction with the organic target by means of the B moiety in the fusion protein according to the invention. The affinity medium is contacted with the sample under suitable conditions to achieve binding between the affinity medium and the organic target. Non-bound sample is removed under suitable conditions to maintain selective binding between the affinity medium and the organic target. This method results in an organic target immobilized to the affinity medium, and specifically to the fusion protein, according to the invention.

In a preferred method according to the invention, the fusion protein in the affinity medium is present as a protein structure according to the invention when contacting the affinity medium with the sample to achieve binding between the affinity medium and the organic target.

A particularly useful protein structure in this respect is a film or a fiber wherein the B moiety is the Z domain derived from staphylococcal protein A or a protein fragment having at least 70% identity, such as at least 80% identity, or at least 90% identity, thereto, see e.g. Example 1-6. The film is advantageous in that it adheres to solid structures, e.g. the plastics in microtiter plates. This property of the film facilitates washing and regeneration procedures and is very useful for separation purposes.

It has surprisingly been observed that the alkali stability of the Z domain may even be enhanced when being part of a fusion protein according to the invention in a protein structure according to the invention. This property may be very useful for washing and regeneration purposes, e.g. allowing for high concentrations of NaOH, such as 0.1 M, 0.5 M, 1 M or even above 1 M, e.g. 2 M, and/or for high concentrations of urea, e.g. 6-8 M. The chemical stability may also be useful to allow for repeated cycles of use of the Z domain for affinity purification. This alkali stability may be further increased by utilizing a stabilized mutant of the Z domain. Furthermore, it has advantageously been shown that the fusion proteins according to the invention, including the Z domain, are heat stable. This allows for sterilization by heat with maintained binding ability.

A known problem with traditional affinity matrices with Z domains is leakage of the Z domain from the affinity matrix. Due to the stable incorporation of the Z domain by a peptide bond into the fusion protein of the invention, it is contemplated that the undesirable leakage of the Z domain from the protein structures according to the invention is low or absent. Another advantage of the fusion proteins according to the invention is that the resulting protein structure has a high density of Z domains (or other B moieties). It is contemplated that this high density provides a high binding capacity. Altogether, these properties of the fusions proteins are very attractive for various B moieties, and in particular for affinity purification using protein Z with good production economy. These properties are also useful in other formats than in traditional gel bead affinity columns, e.g. in filter-like formats.

The immobilized organic target is capable of selective interaction with a second organic target. The method is then further comprising the step of contacting said affinity medium and the immobilized organic target with a second organic target, which is capable of selective interaction with the first organic target, under suitable conditions to achieve binding between the first and second organic targets.

The immobilized organic target is detectable and/or quantifiable. The detection and/or quantification of the organic target may be accomplished in any way known to the skilled person for detection and/or quantification of binding reagents in assays based on various biological or non-biological interactions. The organic targets may be labeled themselves with various markers or may in turn be detected by secondary, labeled affinity ligands to allow detection, visualization and/or quantification. This can be accomplished using any one or more of a multitude of labels, which can be conjugated to the organic target or to any secondary affinity ligand, using any one or more of a multitude of techniques known to the skilled person, and not as such involving any undue experimentation. Non-limiting examples of labels that can be conjugated to organic targets and/or secondary affinity ligands include fluorescent dyes or metals (e.g., fluorescein, rhodamine, phycoerythrin, fluorescamine), chromophoric dyes (e.g., rhodopsin), chemiluminescent compounds (e.g., luminal, imidazole) and bioluminescent proteins (e.g., luciferin, luciferase), haptens (e.g., biotin). A variety of other useful fluorescers and chromophores are described in Stryer L (1968) Science 162: 526-533 and Brand L and Gohlke J R (1972) Annu. Rev. Biochem. 41:843-868. Organic targets and/or secondary affinity ligands can also be labeled with enzymes (e.g., horseradish peroxidase, alkaline phosphatase, beta-lactamase), radioisotopes (e.g., $^3H$, $^{14}C$, $^{32}P$, $^{35}S$ or $^{125}I$) and particles (e.g., gold). In the context of the present disclosure, "particles" refer to particles, such as metal particles, suitable for labeling of molecules. Further, the affinity ligands may also be labeled with fluorescent semiconductor nanocrystals (quantum dots). Quantum dots have superior quantum yield and are more photostable compared to organic fluorophores and are therefore more easily detected (Chan et al. (2002) *Curr Opi Biotech.* 13: 40-46). The different types of labels can be conjugated to an organic target or a secondary affinity ligand using various chemistries, e.g., the amine reaction or the thiol reaction. However, other reactive groups than amines and thiols can be used, e.g., aldehydes, carboxylic acids and glutamine.

If the detection and/or quantification involves exposure to a second organic target or secondary affinity ligand, the affinity medium is washed once again with buffers to remove unbound secondary affinity ligands. As an example, the secondary affinity ligand may be an antibody or a fragment or a derivative thereof. Thereafter, organic targets may be detected and/or quantified with conventional methods. The binding properties for a secondary affinity ligand may vary, but those skilled in the art should be able to determine operative and optimal assay conditions for each determination by routine experimentation.

The detection, localization and/or quantification of a labeled molecule may involve visualizing techniques, such as light microscopy or immunofluoresence microscopy. Other methods may involve the detection via flow cytometry or luminometry. The method of visualization of labels may include, but is not restricted to, fluorometric, luminometric and/or enzymatic techniques. Fluorescence is detected and/or quantified by exposing fluorescent labels to light of a specific wavelength and thereafter detecting and/or quantifying the emitted light in a specific wavelength region. The presence of a luminescently tagged molecule may be detected and/or quantified by luminescence developed during a chemical reaction. Detection of an enzymatic reaction is due to a color shift in the sample arising from chemical reaction. Those of skill in the art are aware that a variety of different protocols can be modified in order for proper detection and/or quantification.

One available method for detection and/or quantification of the organic target is by linking it or the secondary affinity ligand to an enzyme that can then later be detected and/or quantified in an enzyme immunoassay (such as an EIA or ELISA). Such techniques are well established, and their realization does not present any undue difficulties to the skilled person. In such methods, the biological sample is brought into contact with a protein structure according to the invention which binds to the organic target, which is then detected and/or quantified with an enzymatically labeled secondary affinity ligand. Following this, an appropriate substrate is brought to react in appropriate buffers with the enzymatic label to produce a chemical moiety, which for example is detected and/or quantified using a spectrophotometer, fluorometer, luminometer or by visual means.

The organic target or the secondary affinity ligands can be labeled with radioisotopes to enable detection and/or quantification. Non-limiting examples of appropriate radiolabels in the present disclosure are $^3H$, $^{14}C$, $^{32}P$, $^{35}S$ or $^{125}I$. The specific activity of the labeled affinity ligand is dependent upon the half-life of the radiolabel, isotopic purity, and how the label has been incorporated into the affinity ligand. Affinity ligands are preferably labeled using well-known techniques (Wensel T G and Meares C F (1983) in: *Radioimmunoimaging and Radioimmunotherapy* (Burchiel S W and Rhodes B A eds.) Elsevier, New York, pp 185-196). A thus radiolabeled affinity ligand can be used to visualize the organic target by detection of radioactivity. Radionuclear scanning can be performed with e.g. a gamma camera, magnetic resonance spectroscopy, emission tomography, gamma/beta counters, scintillation counters and radiographies.

Thus, the sample may be applied to the protein structure for detection, separation and/or quantification of the organic target. This procedure enables not only detection of the organic target, but may in addition show the distribution and relative level of expression thereof. Optionally, the organic target may be released from the affinity medium and collected. Thus, the use may comprise affinity purification on an affinity medium onto which the organic target has been immobilized. The protein structure may for example be arranged in a column or in well plates (such as 96 well plates), or on magnetic beads, agarose beads or sepharose beads. Further, the use may comprise use of the protein structures on a soluble matrix, for example using a dextran matrix, or use in a surface plasmon resonance instrument, such as a Biacore™ instrument, wherein the analysis may for example comprise monitoring the affinity for the immobilized organic target or a number of potential affinity ligands.

The protein structures according to the invention can be washed and regenerated with various cleaning agents, including acid, base and chaotropic agents. Particularly useful cleaning agents include NaOH, such as 0.1, 0.5 or 1 M NaOH, and urea, such as 6-8 M urea, Since the protein structures according to the invention are surprisingly resistant to chemical treatment and/or sterilizing heat treatment, the methods according to the invention involving use of the protein structures may comprise a final step of regenerating the protein structure. The methods preferably comprise a final step of regenerating the affinity medium by chemical treatment and/or sterilizing heat treatment. It is preferred that the chemical treatment comprises treatment with NaOH, such as 0.1, 0.5 or 1 M NaOH, and/or urea, such as 6-8 M urea, Fusion proteins according to the invention can be also be allowed to bind to an organic target in solution, i.e. prior to allowing the fusion protein to polymerize and form a protein structure, such as a film, a foam or a fibre. Both the spidroin-derived moieties (e.g. REP-CT) as such and the corresponding fusion proteins incorporating a B moiety polymerise into solid structures even in the presence of contaminating proteins, without appreciable incorporation of contaminants into the material, and the functional (B) moieties retain their expected binding properties. It is therefore contemplated that the binding properties of the B moiety can be used to capture compounds or cells from the surrounding solution and incorporate the captured compounds or cells into or on a protein structure according to the invention.

Thus, in another preferred method according to the invention, the fusion protein in the affinity medium is present in solution when contacting the affinity medium with the sample to achieve binding between the affinity medium and the organic target. The complex of fusion protein bound to the organic target is then allowed to form a fusion protein structure according to the invention.

This method may be particularly useful when the purpose is to "fish out" specific molecules or cells from a solution, e.g. to obtain target molecules from the media in large scale eukaryotic cell production systems when the target proteins are secreted. Since the binding of target molecules and formation of solid structures by the spidroin-derived moieties can take place at physiological conditions and since the spidroin-derived moieties are cytocompatible, the method can be applied repeatedly to an ongoing production process.

The protein structure according to the invention is also useful in separation, immobilization and/or cultivation of cells. A particularly useful protein structure in this respect is a film, a fiber or a foam, see e.g. Example 14 and 23. The film is advantageous in that it adheres to solid structures, e.g. the plastics in microtiter plates. This property of the film facilitates washing and regeneration procedures and is very useful for separation purposes.

The present invention thus provides a cell scaffold material for cultivation of cells having an organic target that is present on the cell surface. The cell scaffold material is comprising a protein structure according to the invention. In certain embodiments, the cell scaffold material is consisting of the protein structure according to the invention.

It has been found by the present inventors that a cell scaffold material comprising a polymer comprising, and optionally consisting of, the fusion protein according to the invention provides a beneficial environment for the cultivation of cells, and preferably eukaryotic cells, in a variety of different settings. Furthermore, this environment enables the establishment of cultures of cells that are otherwise very difficult, very costly or even impossible to culture in a laboratory, and for the establishment of cell-containing materials useful for tissue engineering and/or transplantation.

The invention also provides a combination of cells, preferably eukaryotic cells, and the cell scaffold material according to the invention. Such a combination according to the invention may be presented in a variety of different formats, and tailored to suit the needs of a specific situation. It is contemplated, for example, that the inventive combination may be useful as a cell-containing implant for the replacement of cells in damaged or diseased tissue.

The cell scaffold material can be utilized to capture cells either directly or indirectly. In direct capture, the B moiety is capable of selective interaction with an organic target that is present on the cell surface. Alternatively, the B moiety is capable of selective interaction with and is bound to an intermediate organic target, and that intermediate organic target is capable of selective interaction with an organic target that is present on the cell surface. Thus, in indirect capture, the cell scaffold material is further comprising an intermediate organic target, and the B moiety is capable of selective interaction with and is bound to said intermediate organic target. The intermediate organic target, in turn, is capable of selective interaction with the organic target that is present on the cell surface.

In one embodiment of the cell scaffold materials as disclosed herein, the fusion protein is further comprises an oligopeptide cell-binding motif. In connection with the cultivation of certain cells in certain situations, the presence of oligopeptide cell-binding motifs has been observed to improve or maintain cell viability, and the inclusion of such a motif into the cell scaffold material as a part of the spider silk protein is thought to provide additional benefits. The cell-binding motif is an oligopeptide coupled to the rest of the fusion protein via at least one peptide bond. For example, it may be coupled to the N-terminal or the C-terminal of the rest of the fusion protein, or at any position within the amino acid sequence of the rest of the spider silk protein. With regard to the selection of oligopeptidic cell-binding motifs, the skilled person is aware of several alternatives. Said oligopeptide may for example comprise an amino acid sequence selected from the group consisting of RGD, IKVAV, YIGSR, EPDIM and NKDIL. RGD, IKVAV and YIGSR are general cell-binding motifs, whereas EPDIM and NKDIL are known as keratinocyte-specific motifs that may be particularly useful in the context of cultivation of keratinocytes. Other useful cell-binding motifs include GRKRK from tropoelastin, KYGAASIKVAVSADR (laminin derived), NGEPRGDTYRAY (from bone sialoprotein), PQVTRGDVFTMP (from vitronectin), and AVTGRGDSPASS (from fibronectin). The coupling of an oligopeptide cell-binding motif to the rest of the spider silk protein is readily accomplished by the skilled person using standard genetic engineering or chemical coupling techniques. Thus, in some embodiments, the cell-binding motif is introduced via genetic engineering, i.e. forming part of a genetic fusion between a nucleic acid encoding a fusion protein and the cell-binding motif. As an additional beneficial characteristic of such embodiments, the cell-binding motif will be present in a 1:1 ratio to the monomers of fusion protein in the polymer making up the cell scaffold material.

The polymer in the cell scaffold material used in the methods or combination described herein may adopt a variety of physical forms, and use of a specific physical form may offer additional advantages in different specific situations. For example, in an embodiment of the methods or combination, said cell scaffold material is in a physical form selected from the group consisting of film, foam, fiber and fiber-mesh.

The present invention accordingly provides a method for immobilization of cells. A sample e.g. a biological sample such as blood, comprising cells of interest is provided. The biological sample may be an earlier obtained sample. If using an earlier obtained sample in a method, no steps of the method are practiced on the human or animal body.

The sample is applied to a cell scaffold material according to the invention under suitable conditions to allow selective interaction between the cell scaffold material and an organic target that is present on the surface of the cells of interest. The cells are allowed to immobilize to said cell scaffold material by binding between the organic target on the cell surface and said cell scaffold material. Non-bound sample is removed under suitable conditions to maintain selective binding between the cell scaffold material and the organic target. This method results in cells exhibiting the organic target being immobilized to the cell scaffold material, and specifically to the protein structure, according to the invention.

As set out above, the cell scaffold material can be utilized to capture cells either directly or indirectly. In direct capture, the B moiety is capable of selective interaction with an organic target that is present on the cell surface. Alternatively, the B moiety is capable of selective interaction with and is bound to an intermediate organic target, and that intermediate organic target is capable of selective interaction with an organic target that is present on the cell surface. Thus, in indirect capture, the cell scaffold material is further comprising an intermediate organic target, and the B moiety is capable of selective interaction with and is bound to said intermediate organic target. The intermediate organic target, in turn, is capable of selective interaction with the organic target that is present on the cell surface.

Regardless of capture method, the captured cells may be released from the fusion protein by cleavage of the fusion protein to release the moiety involved in cell capture from the cell scaffold material. As mentioned hereinabove, the fusion protein may include a cleavage site in its amino acid sequence, which allows for cleavage and removal of the relevant moiety, typically the B moiety or a cell-binding motif. Various cleavage sites are known to the person skilled in the art, e.g. cleavage sites for chemical agents, such as CNBr after Met residues and hydroxylamine between Asn-Gly residues, cleavage sites for proteases, such as thrombin or protease 3C, and self-splicing sequences, such as intein self-splicing sequences.

The present invention also provides a method for cultivation of cells. Cells of interest are immobilized to the cell scaffold material using the method disclosed hereinabove. The combination of the cell scaffold material and the immobilized cells are maintained under conditions suitable for cell culture.

In the context of the present invention, the terms "cultivation" of cells, "cell culture" etc are to be interpreted broadly, such that they encompass for example situations in which cells divide and/or proliferate, situations in which cells are maintained in a differentiated state with retention of at least one functional characteristic exhibited by the cell type when present in its natural environment, and situations in which stem cells are maintained in an undifferentiated state.

The present invention will in the following be further illustrated by the following non-limiting examples.

EXAMPLES

Example 1

Cloning, Expression and Fiber Formation of an IgG-Binding Fusion Protein

To prove the fusion protein concept, a Rep$_4$CT protein (a REP moiety with 4 internal repeats and a CT moiety) was produced in fusion with the Z protein domain (a B moiety). The Z domain is an engineered version of the immunoglobulin G (IgG) binding domain B of staphylococcal protein A, and is a 58 amino acid long triple-helix motif that binds the fragment crystallisable (F$_c$) region of IgG. Our aim was to investigate whether it is possible to produce structures, such as fibers, films and membranes, from a fusion protein consisting of the Z domain fused to Rep$_4$CT (denoted His$_6$ZQGRep$_4$CT, SEQ ID NO: 14) and still retain the IgG-binding ability of domain Z, as well as the structure forming properties of Rep$_4$CT. In order to do so a fusion protein consisting of the Z domain N-terminally to Rep$_4$CT was cloned.

Cloning

A gene encoding the His$_6$ZQGRep$_4$CT fusion protein (SEQ ID NOS: 14-15) was constructed as follows. Primers were designed in order to generate PCR fragments of domain Z from a vector containing such a Z sequence. Also, the primers contained a recognition site for Protease 3C cleavage (LEALFQGP, denoted QG) between Z and Rep$_4$CT. The resulting PCR products were then treated with the restriction endonucleases NdeI and EcoRI, as was the target vector (denoted pT7His$_6$TrxHis$_6$QGRep$_4$CT, harbouring a kanamycin resistance gene). Upon restriction cleavage of the target vector, the TrxHis$_6$QG part was cleaved off. Cleaved PCR fragments and target vector were joined together with the aid of a T4 DNA Ligase, whereupon the resulting, correctly ligated vector (pT7His$_6$ZQGRep$_4$CT) was transformed into chemocompetent Escherichia coli (E. coli) BL21 (DE3) cells that were allowed to grow onto agar plates supplemented with kanamycin (70 µg/ml). Colonies were thereafter picked and PCR screened for correct insert and subsequently also sequenced to confirm the DNA sequence inserted of ZQG into the target vector.

Production

E. coli BL21 (DE3) cells possessing the pT7His$_6$ZQGRep$_4$CT vector were grown in Luria-Bertani medium (6 liter in total) supplemented with kanamycin (70 µg/ml) to an OD$_{600}$ value of 1-1.5 in 30° C., followed by induction of His$_6$ZQGRep$_4$CT expression with 300 µM IPTG (isopropyl β-D-1-thiogalactopyranoside) and further incubation in 20° C. for approximately 2 h. Next, the cells were harvested by a 20 min centrifugation at 4 700 rpm, and the resulting cell pellets were dissolved in 20 mM Tris (pH 8.0).

Purification

Cell pellets dissolved in 20 mM Tris (pH 8.0) were supplemented with lysozyme and DNase I in order to lyse the bacterial cells, whereupon the cell lysates were recovered after 15 000 rpm of centrifugation for 30 min. Next, the recovered cell lysates were divided and loaded onto a total of four Chelating Sepharose Fast Flow Zn$^{2+}$ columns, keeping the His$_6$ZQGRep$_4$CT protein bound to the column matrix via the His$_6$ tag. After washing, bound proteins were eluted with 20 mM Tris/300 mM imidazole (pH 8.0). The pooled eluate fractions contained 27 mg of His$_6$ZQGRep$_4$CT protein according to an A$_{280}$ measurement. Next, the pooled eluate liquid was divided into two equal halves (13.5 mg of His$_6$ZQGRep$_4$CT in each), where the first half was dialysed against 5 liters of 20 mM Tris (pH 8.0) over night, concentrated to 1.07 mg/ml and finally allowed to form fibers. FIG. 3 shows a macroscopic His$_6$ZQGRep$_4$CT fiber. The formation of fibers from this fusion protein (SEQ ID NO: 14) illustrates that the Z domain (B moiety) does not interfere with the fiber forming properties of Rep$_4$CT (REP and CT moieties). The amount of His$_6$ZQGRep$_4$CT protein prior to cleavage with Protease 3C was 10 mg after dialysis and concentration (FIG. 4).

The second half of the eluate pool was cleaved with 1.34 mg of Protease 3C, supplemented with 1 mM dithiothreitol (DTT), separating His$_6$Z from Rep$_4$CT. The cleavage was performed over night under dialysis against 20 mM Tris (pH 8.0), after which the protein solution was allowed to pass a Ni-NTA Agarose column, and the flow through fraction, containing Rep$_4$CT, was collected, concentrated to 0.79 mg/ml and allowed to form fibers. The final amount of Rep$_4$CT after cleavage was 6 mg (FIG. 4).

Figure 4:
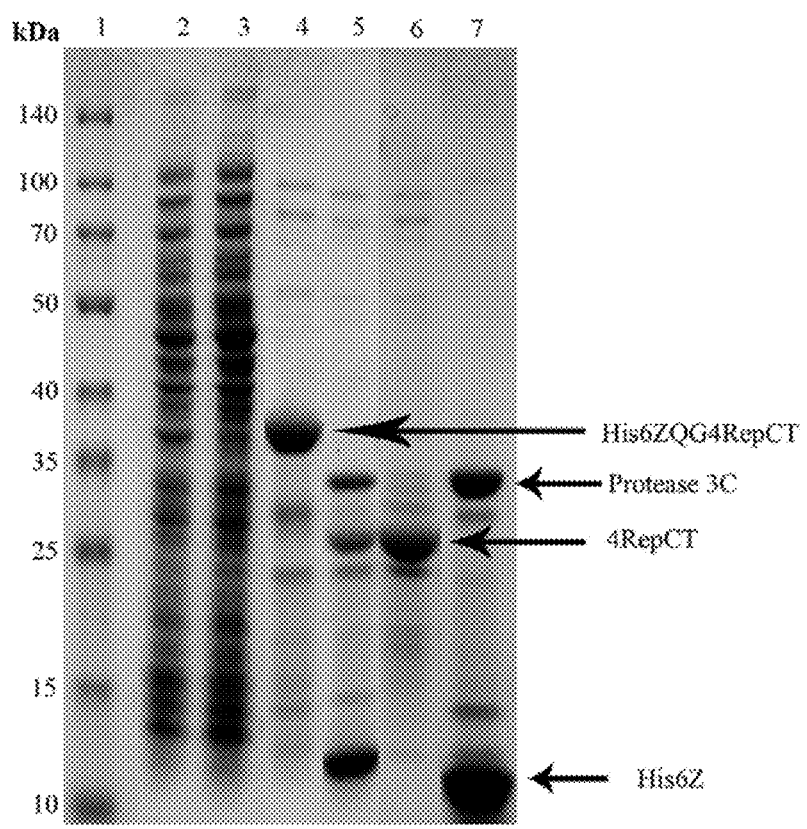
FIG. 4 shows a SDS-PAGE gel from purification and analysis of a fusion protein comprising a Z domain.

FIG. 4 shows an SDS-PAGE gel from the purification of the fusion protein His$_6$ZQGRep$_4$CT (SEQ ID NO: 14) and its subsequent Protease 3C cleavage product Rep$_4$CT (residues 81-339 of SEQ ID NO: 14). The gel was loaded in the following order:
(1) Spectra Multicolor Broad Range Protein Ladder, Fermentas
(2) Cell lysate
(3) Flow through from cell lysate loaded onto a Chelating Sepharose Fast Flow Zn$^{2+}$ column
(4) Eluate pool of His$_6$ZQGRep$_4$CT from a Chelating Sepharose Fast Flow Zn$^{2+}$ column
(5) His$_6$ZQGRep$_4$CT cleaved with Protease 3C (6) Flow through of cleaved His$_6$ZQGRep$_4$CT loaded onto a Ni-NTA Agarose column
(7) Regeneration of the Ni-NTA Agarose column with 5 ml of 20 mM Tris/500 mM imidazole (pH 8.0).
The molecular weights of His$_6$ZQGRep$_3$CT, His$_6$Z, Rep$_4$CT and Protease 3C are 32 kDa, 9 kDa, 23 kDa and 30 kDa, respectively.

The fact that macroscopic fibers of His$_6$ZQGRep$_4$CT (SEQ ID NO: 14) could be obtained although Rep$_4$CT has been fused to another protein, i.e. the 58 amino acid long Z domain with binding affinity for IgG, demonstrates that Rep$_4$CT still retains its fiber forming properties despite fused to the Z domain (residues 13-70 of SEQ ID NO: 14). Moreover, the Z domain of the fusion protein seems to confer good solubility to His$_6$ZQGRep$_4$CT.

Example 2

Binding of Biotinylated IgG to Fusion Protein Fibers

To further prove the fusion protein concept, it was studied whether the B moiety in a fusion protein structure retains its capacity of selective interaction with an organic target. In this study, the ability of the Z domain (B moiety) in fibers of the fusion protein His$_6$ZQGRep$_4$CT (SEQ ID NO: 14) to bind IgG was assessed. A solution of biotinylated rabbit IgG was incubated with His$_6$ZQGRep$_4$CT fibers, after which the same fibers were incubated in a solution with streptavidin-functionalized beads, and the fibers were subsequently visualized in a light microscope. The choice of using IgG made in rabbit falls back on the fact that IgG from rabbit bind with strong affinity to the Z domain.

An approximately 50 mm long His$_6$ZQGRep$_4$CT fiber, prepared as described in Example 1, was immersed in a binding solution containing 50 µl of 1×PBS/0.5% bovine serum albumin and 10 µl of 0.5 mg/ml biotinylated IgG produced in rabbit (anti-rat IgG (H+L), mouse adsorbed, Vector Laboratories, Inc.), and incubated for 75 min in room temperature with light shaking. The supernatant was discarded, and the fiber was washed three times in 60 µl 1×PBS/0.07% Tween 20. Next, the fiber was immersed in a solution containing 40 µl of 1×PBS/0.5% bovine serum albumin and 20 µl of 10 mg/ml Dynabeads M-280 Streptavidin (Dynal AS), and again incubated for 75 min in room temperature with light shaking. The supernatant was discarded and the fiber washed three times in 60 µl 1×PBS/0.07% Tween 20.

To get an indication of nonspecific binding of Dynabeads to the fiber, another His$_6$ZQGRep$_4$CT fiber was immersed in only a Dynabeads solution, as described above, without the preceding incubation with biotinylated IgG. The same procedure as described above for His$_6$ZQGRep$_4$CT was performed with fibers of Rep$_4$CT type, and all fibers were visualized in a USB microscope with a fixed 500× magnification.

Figure 5:
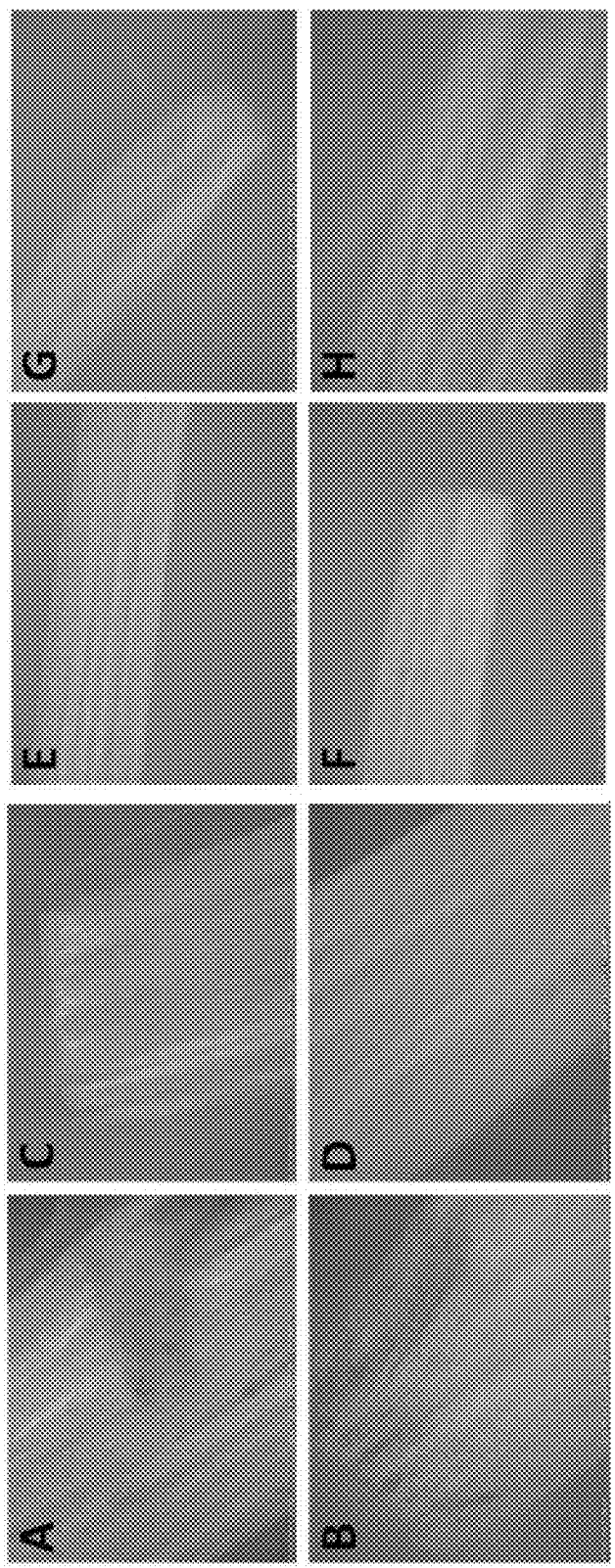
FIG. 5 shows fibers made of fusion proteins and control fibers that illustrate functionality of the Z domain in a fusion protein.

FIG. 5 is a visualization of His$_6$ZQGRep$_4$CT and Rep$_4$CT fibers after binding of biotinylated rabbit IgG, followed by streptavidin-functionalised Dynabeads. Panels (A, B) show two representative pictures of the His$_6$ZQGRep$_4$CT fiber, taken at different positions along the fiber, that first was incubated with biotinylated IgG (produced in rabbit), followed by incubation with Dynabeads M-280 Streptavidin (Ø 2.8 µm). Panels (C, D) show two representative pictures of another His$_6$ZQGRep$_4$CT fiber that was only immersed in a Dynabeads Streptavidin solution, without the preceding incubation with IgG. The corresponding pictures of Rep$_4$CT fibers are shown in panels (E, F) and (G, H), respectively. All pictures were taken at a fixed 500× magnification with a USB microscope and the Dynabeads appears in the pictures as dark grey dots.

In FIG. 5, it seems like the Dynabeads are almost only seen in panels A and B, both these pictures showing a His$_6$ZQGRep$_4$CT fiber subjected to biotinylated IgG, followed by streptavidin-functionalised Dynabeads. This result implies that a considerable fraction of the Z domains in the fusion protein have retained their IgG-binding ability in His$_6$ZQGRep$_4$CT after fiber formation.

Example 3

Binding of Pure and Serum IgG to Fusion Protein Fibers and Films

To further explore the capacity of the B moiety in a fusion protein structure of selective interaction with an organic target, the ability of domain Z in the fusion protein His$_6$ZQGRep$_4$CT (SEQ ID NO: 14) to bind IgG was studied. Fibers and films of this fusion protein were used for binding of purified IgG and IgG from serum, followed by elution and subsequent analysis on SDS-PAGE, where IgG under non-reducing conditions appears as a ~146 kDa band. Serum is the remaining fluid phase after blood clotting, and the two main constituents of serum are albumin and IgG. In rabbit serum, for example, the concentration of IgG is 5-10 mg/ml and that of albumin even higher. Purified IgG and serum were both of rabbit source.

Figure 6:
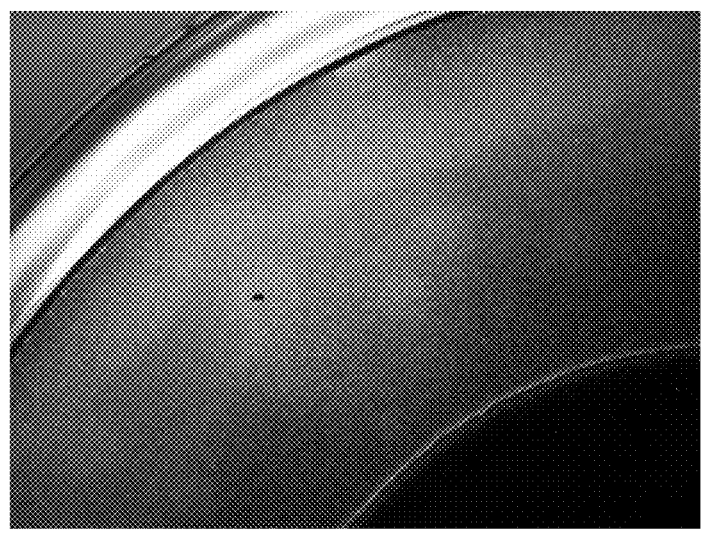
FIG. 6 shows part of a casted film made of fusion proteins at the bottom of a tissue culture plate.

Films of His6ZQGRep$_4$CT were prepared by air-drying 100 µl of protein solution (0.96 mg/ml) over night at room temperature at the bottom of individual wells of a 24-well tissue culture plate. The casted films were then stored at +4° C. for 18 days, either immersed in 20 mM Tris (pH 8.0), denoted "T films", or without immersed in any liquid, denoted "A films". FIG. 6 shows part of a casted His$_6$ZQGRep$_4$CT film made at the bottom of a well from a hydrophilic, 24-well tissue culture plate. To capture the picture, an inverted light microscope at 2× magnification was used. Fibers of the fusion protein were prepared as described in Example 1 and stored at +4° C. in 20 mM Tris (pH 8.0) until used.

Two parallel experiment setups were conducted. In the first setup, triplicates of T films, A films and fibers made of His$_6$ZQGRep$_4$CT were immersed in 500 µl of 50 µg/ml purified rabbit IgG (purified from pooled rabbit sera, Vector Laboratories, Inc.) for 1 h at room temperature with mild shaking. In the other setup, triplicates of the same type of His6ZQGRep$_4$CT films and fibers were instead immersed in 500 µl of a five times dilution of heat-inactivated, centrifuged rabbit serum (National Veterinary Institute, Uppsala, Sweden), also for 1 h at room temperature with mild shaking. The supernatant was discarded from all fibers and films, followed by washing three times in 500 µl 20 mM Tris (pH 8.0). Bound IgG, from purified IgG or from serum, was eluted by 30 min of incubation in 500 µl of 0.5 M acetic acid/1 M urea/100 mM NaCl (pH 2.7). The same procedure as described above for His$_6$ZQGRep$_4$CT fibers and A films was also conducted for films and fibers of His$_6$TrxHis$_6$QGRep$_4$CT and Rep$_4$CT as controls. Eluted fractions were analysed with SDS-PAGE under non-reducing conditions (FIG. 7-9).

Figure 7:
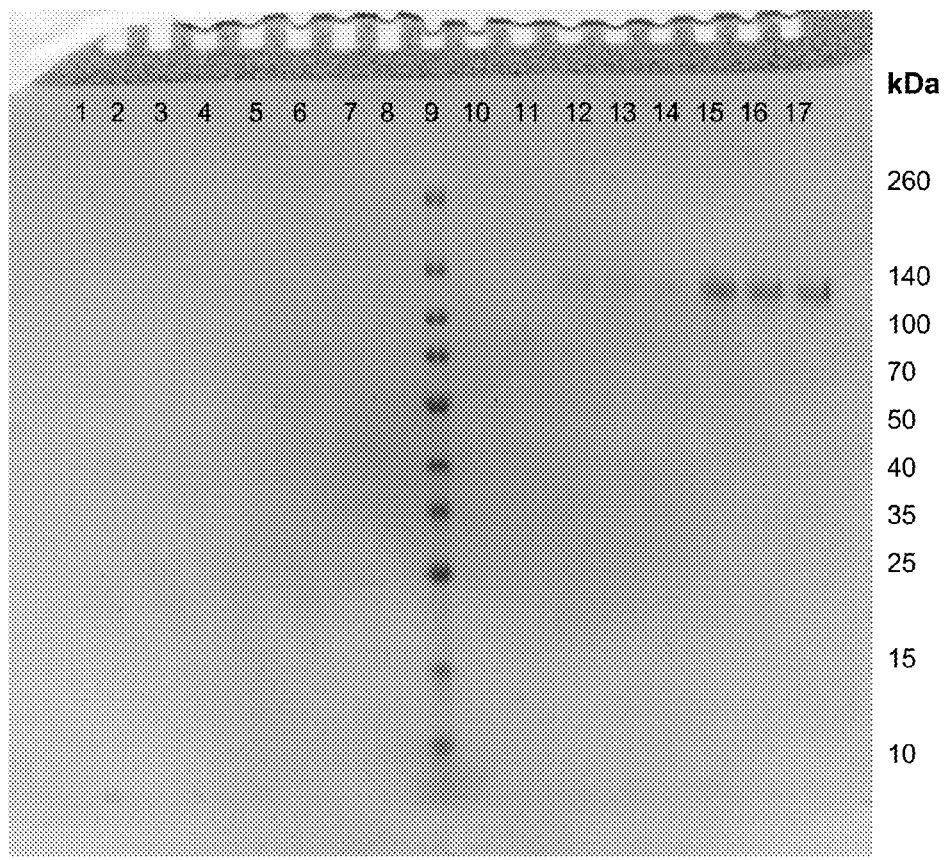
FIGS. 7-12 show non-reducing SDS-PAGE gels illustrating the functionality of the Z domain in fusion protein structures.

FIG. 7 shows a non-reducing SDS-PAGE gel. Eluted fractions were loaded in lanes as follows:
(1-3) His$_6$TrxHis$_6$QGRep$_4$CT, A film, incubated with rabbit IgG
(4-6) His$_6$TrxHis$_6$QGRep$_4$CT, A film, incubated with rabbit serum (7-8) His$_6$TrxHis$_6$QGRep$_4$CT, fiber, incubated with rabbit IgG
(9) Spectra Multicolor Broad Range Protein Ladder, Fermentas
(10-11) His$_6$TrxHis$_6$QGRep$_4$CT, fiber, incubated with rabbit serum
(12-14) His$_6$ZQGRep$_4$CT, T film, incubated with rabbit IgG
(15-17) His$_6$ZQGRep$_4$CT, T film, incubated with rabbit serum.

Figure 8:
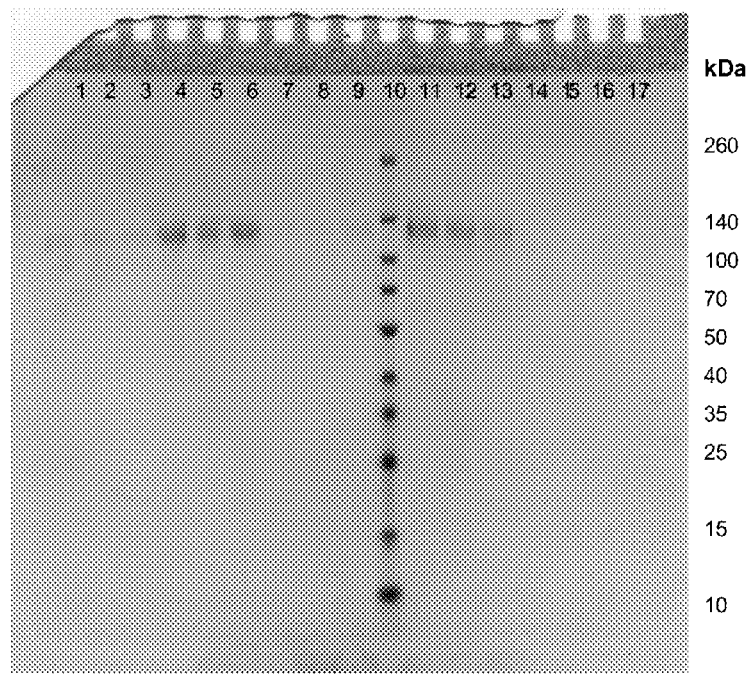

FIG. 8 shows another non-reducing SDS-PAGE gel. Eluted fractions were loaded according to:
(1-3) His$_6$ZQGRep$_4$CT, A film, incubated with rabbit IgG
(4-6) His$_6$ZQGRep$_4$CT, A film, incubated with rabbit serum
(7-9) His$_6$ZQGRep$_4$CT, fiber, incubated with rabbit IgG
(10) Spectra Multicolor Broad Range Protein Ladder, Fermentas
(11-13) His$_6$ZQGRep$_4$CT, fiber, incubated with rabbit serum
(14-16) Rep$_4$CT, A film, incubated with rabbit IgG.

Figure 9:
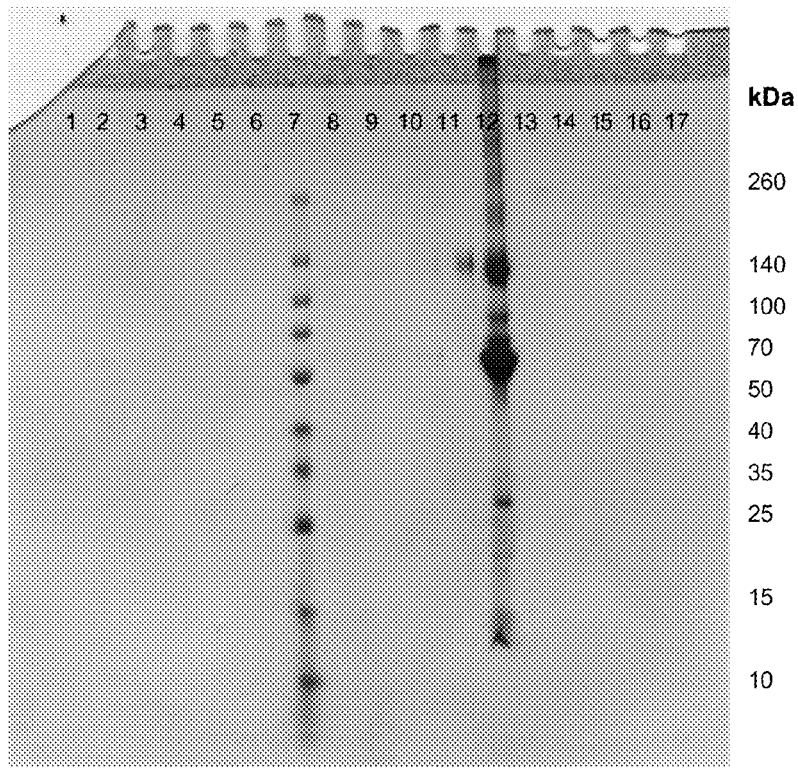

FIG. 9 shows a further non-reducing SDS-PAGE gel. Eluted fractions were loaded according to:
(1-3) Rep$_4$CT, A film, incubated with rabbit serum
(4-6) Rep$_4$CT, fiber, incubated with rabbit IgG
(7) Spectra Multicolor Broad Range Protein Ladder, Fermentas
(8-10) Rep$_4$CT, fiber, incubated with rabbit serum
(11) Purified rabbit IgG (50 µg/ml), used in incubation
(12) Rabbit serum (1:50 dilution), used in incubation.

The results in FIG. 7-9 show that all types of His$_6$ZQGRep$_4$CT matrices, i.e. films (both A and T type) and fibers have the ability to bind IgG (either purified or from serum) via the Z domain. Moreover, the His$_6$ZQGRep$_4$CT matrices exposed to rabbit serum do not seem to bind anything else of the serum fraction but IgG. Matrices of the other two protein variants used (i.e. His$_6$TrxHis$_6$QGRep$_4$CT and Rep$_4$CT) do not seem to bind anything at all, except from fibers of Rep$_4$CT exposed to serum, and that show weak bands within the IgG (~146 kDa) and albumin (~70 kDa) region. This approach to evaluate the IgG-binding ability of the Z domain within the fusion protein His$_6$ZQGRep$_4$CT (SEQ ID NO: 14) is a strong indication that the Z domain is active in both fiber and film versions of the fusion protein. No other fraction of rabbit serum than IgG is observed to bind to His$_6$ZQGRep$_4$CT.

Example 4

Binding Reproducibility of Pure and Serum IgG to Fusion Protein Fibers and Films To explore the reproducibility of the IgG binding to films and fibers of the fusion protein His$_6$ZQGRep$_4$CT (SEQ ID NO: 14), the experiments in Example 3 were performed again. The same fibers and films of His$_6$ZQGRep$_4$CT, His$_6$TrxHis$_6$QGRep$_4$CT and Rep$_4$CT that were used in Example 3 were used again. All fiber and film materials had been immersed for 70 days in 20 mM Tris (pH 8.0) at +4° C. after the previous experiments had been performed. The experiments were carried out as described in Example 3. Eluted fractions were analysed with SDS-PAGE under non-reducing conditions (FIGS. 10-12).

Figure 10:
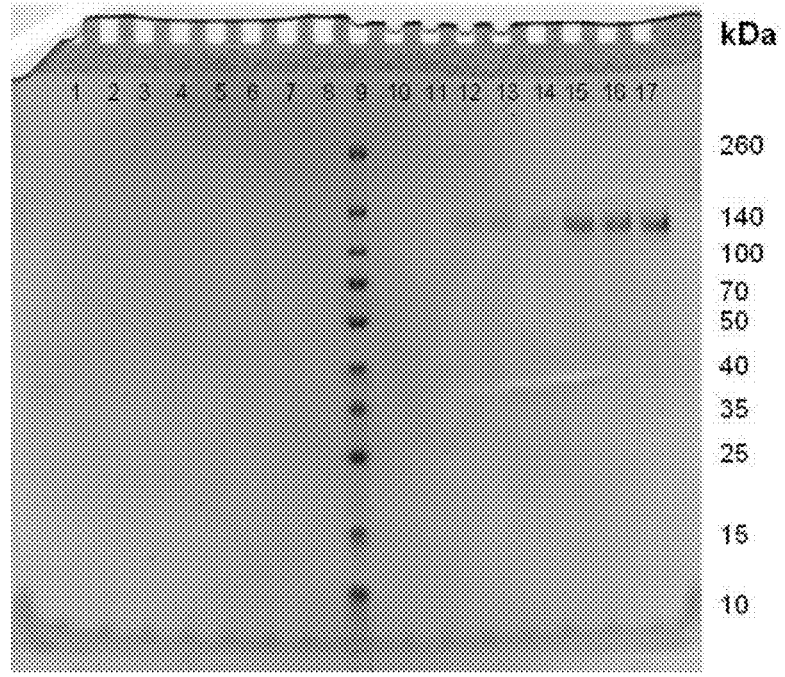

FIG. 10 shows a non-reducing SDS-PAGE gel. Eluted fractions were loaded according to:
(1-3) His$_6$TrxHis$_6$QGRep$_4$CT, A film, incubated with rabbit IgG
(4-6) His$_6$TrxHis$_6$QGRep$_4$CT, A film, incubated with rabbit serum
(7-8) His$_6$TrxHis$_6$QGRep$_4$CT, fiber, incubated with rabbit IgG
(9) Spectra Multicolor Broad Range Protein Ladder, Fermentas
(10-11) His$_6$TrxHis$_6$QGRep$_4$CT, fiber, incubated with rabbit serum
(12-14) His$_6$ZQGRep$_4$CT, T film, incubated with rabbit IgG
(15-17) His$_6$ZQGRep$_4$CT, T film, incubated with rabbit serum.

Figure 11:
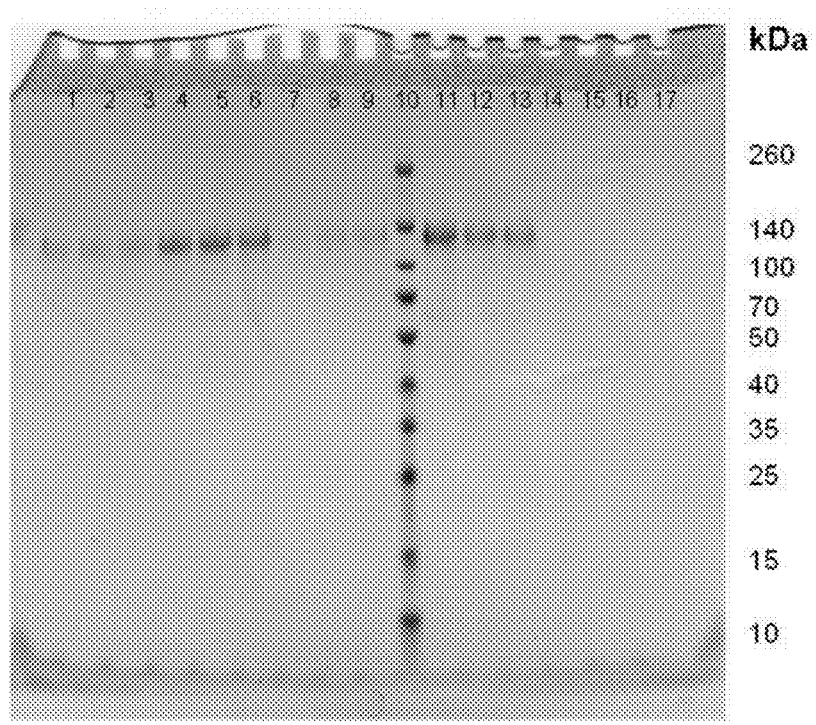

FIG. 11 shows another non-reducing SDS-PAGE gel. Eluted fractions were loaded according to:
(1-3) His$_6$ZQGRep$_4$CT, A film, incubated with rabbit IgG
(4-6) His$_6$ZQGRep$_4$CT, A film, incubated with rabbit serum
(7-9) His$_6$ZQGRep$_4$CT, fiber, incubated with rabbit IgG
(10) Spectra Multicolor Broad Range Protein Ladder, Fermentas
(11-13) His$_6$ZQGRep$_4$CT, fiber, incubated with rabbit serum
(14-16) Rep$_4$CT, A film, incubated with rabbit IgG.

Figure 12:
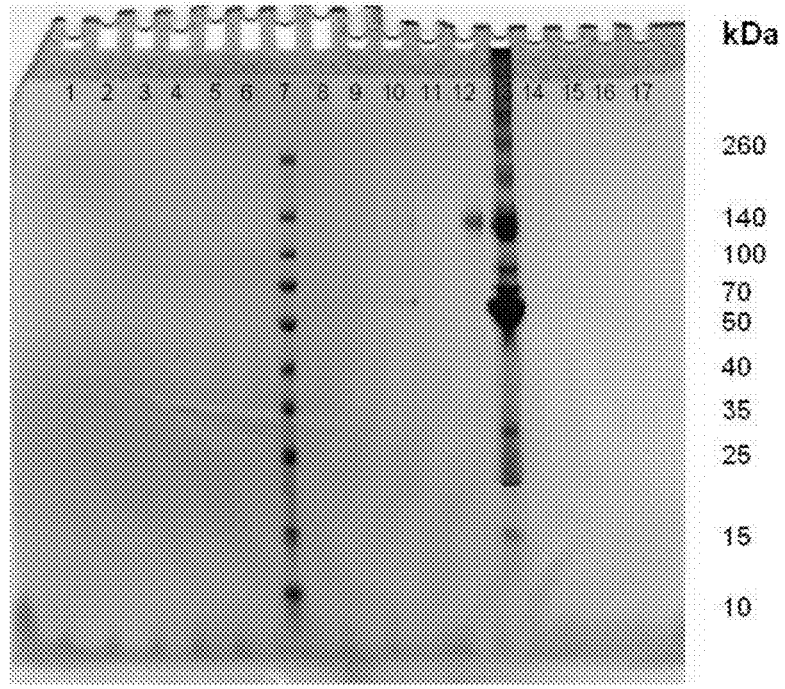

FIG. 12 shows a non-reducing SDS-PAGE gel. Eluted fractions were loaded according to:
(1-3) Rep$_4$CT, type A film, incubated with rabbit serum
(4-6) Rep$_4$CT, fiber, incubated with rabbit IgG
(7) Spectra Multicolor Broad Range Protein Ladder, Fermentas
(8-10) Rep$_4$CT, fiber, incubated with rabbit serum
(11) Empty well
(12) Purified rabbit IgG (50 µg/ml), used in incubation
(13) Rabbit serum (1:50 dilution), used in incubation.

The IgG binding patterns for all three protein matrices (i.e. His$_6$ZQGRep$_4$CT, His$_6$TrxHis$_6$QGRep$_4$CT and Rep$_4$CT) corresponds to what was observed in Example 3, although rather weak bands corresponding to albumin (~70 kDa) is seen for His$_6$ZQGRep$_4$CT fibers incubated with rabbit serum. This initial IgG-binding reproducibility study, show that both fibers and films of His$_6$ZQGRep$_4$CT can be used at least twice for binding and elution of purified and serum IgG. A further study of reproducibility is reported in Example 19.

Example 5

IgG Binding to Fusion Protein Matrices and to a Commercial Protein a Matrix

The IgG-binding capacity of His$_6$ZQGRep$_4$CT fusion protein structures was evaluated by comparison with a commercially available protein A matrix (Protein A Sepharose CL-4B, GE Healthcare). Fibers and films of His$_6$ZQGRep$_4$CT (SEQ ID NO: 14) were prepared inside spin columns. The protein A matrix was also added to spin columns in such a way that the total number of protein A molecules attached to the matrix was equal to the total number of Z molecules within His$_6$ZQGRep$_4$CT films. Binding of purified IgG and IgG from serum to films and fibers of His$_6$ZQGRep$_4$CT, as well as to the protein A matrix was allowed to occur, followed by elution and subsequent analysis on SDS-PAGE.

Films of His$_6$ZQGRep$_4$CT were prepared by air-drying 100 µl of protein solution (1.05 mg/ml) for three days at room temperature at the bottom of the polyethylene frit inside spin columns (SigmaPrep™ Spin Columns, Sigma), giving a total of 3×10$^{-9}$ mole of His$_6$ZQGRep$_4$CT per film. Also, fibers of His$_6$ZQGRep$_4$CT were placed onto frits inside the same type of spin columns.

The same procedure was carried out for films and fibers of Rep$_4$CT, where the films contained a total of 4×10$^{-9}$ mole of Rep$_4$CT per film. For the commercial protein A matrix, a drained matrix volume corresponding to 3×10$^{-9}$ mole of protein A was transferred to the frit per spin column, whereupon the matrix was washed with 1×500 µl plus 2×150 µl of deionized water by centrifugation of the spin columns at 400 rcf for 1.5 min.

Two parallel experiment setups were conducted for fibers and films of His$_6$ZQGRep$_4$CT and Rep$_4$CT, as well as with the protein A matrix. In the first setup, duplicates of all three different matrices were immersed in 500 µl of 50 µg/ml purified rabbit IgG (IgG purified from rabbit serum, Sigma) for 1 h at room temperature. In the other setup, duplicates of the same three types of matrices were instead immersed in 500 µl of a five times dilution of centrifuged rabbit serum (Normal rabbit serum, Invitrogen), also for 1 h at room temperature.

The supernatant was discarded from all fibers and films by simple pipetting and for the protein A matrix by centrifugation (400 rcf, 1.5 min), followed by washing three times in 500 µl 20 mM Tris (pH 8.0). Bound IgG, from purified IgG or from serum, was eluted by 30 min of incubation in 500 µl of 0.5 M acetic acid/1 M urea/100 mM NaCl (pH 2.7). Eluted fractions were analysed on SDS-PAGE under non-reducing conditions (FIGS. 13-15), and are denoted as coming from run 1. Immediately after the elution, all matrices were washed with 3×500 µl 20 mM Tris (pH 8.0), after which the just described experiment was repeated once more to evaluate the reproducibility of IgG binding. Eluted fractions from the repeated experiment are denoted as coming from run 2. Note: Under non-reducing SDS-PAGE conditions, the molecular weight of IgG is around 146 kDa.

Figure 13:
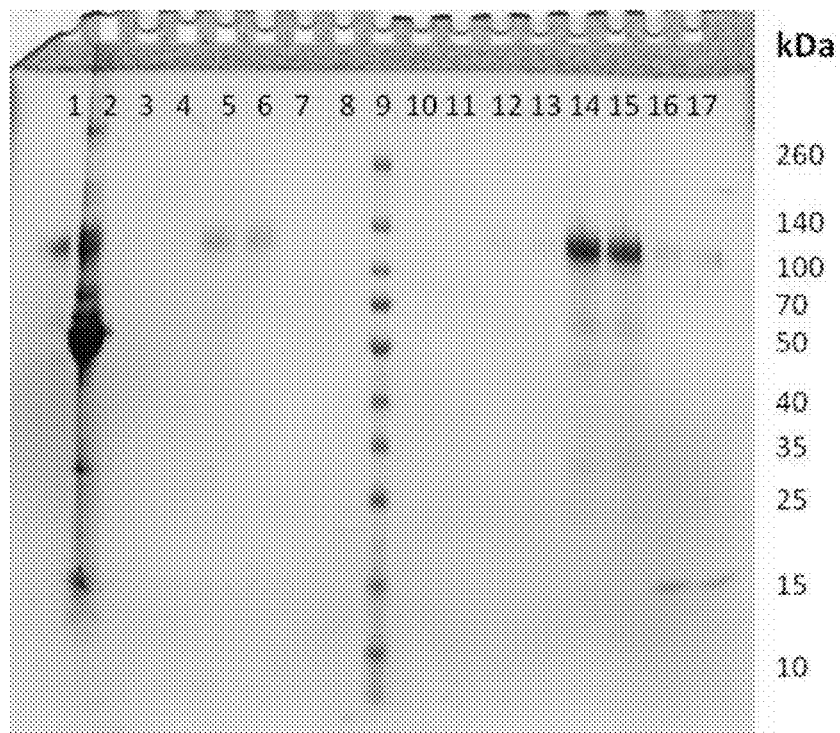
FIGS. 13-15 show non-reducing SDS-PAGE gels illustrating the IgG-binding capacity of the Z domain in a fusion protein structures compared to a commercial protein A matrix.

FIG. 13 shows a non-reducing SDS-PAGE gel of eluted fractions from run 1, loaded according to:
(1) Purified rabbit IgG (50 µg/ml), used in incubation
(2) Rabbit serum (1:50 dilution), used in incubation
(3-4) His$_6$ZQGRep$_4$CT, film, incubated with rabbit IgG
(5-6) His$_6$ZQGRep$_4$CT, film, incubated with rabbit serum
(7-8) Rep$_4$CT, film, incubated with rabbit IgG
(9) Spectra Multicolor Broad Range Protein Ladder, Fermentas
(10-11) Rep$_4$CT, film, incubated with rabbit serum
(12-13) Protein A Sepharose CL-4B matrix, incubated with rabbit IgG
(14-15) Protein A Sepharose CL-4B matrix, incubated with rabbit serum
(16-17) His$_6$ZQGRep$_4$CT, fiber, incubated with rabbit IgG.

Figure 14:
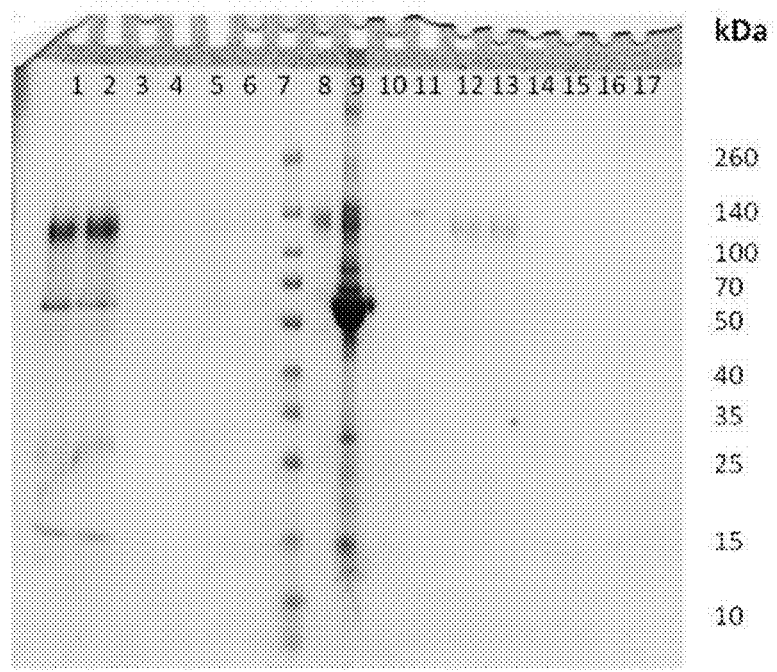

FIG. 14. shows a non-reducing SDS-PAGE gel of eluted fractions coming from both run 1 and run 2, loaded according to:
(1-2) His$_6$ZQGRep$_4$CT, fiber, incubated with rabbit serum, run 1
(3-4) Duplicates of Rep$_4$CT, fiber, incubated with rabbit IgG, run 1
(5-6) Duplicates of Rep$_4$CT, fiber, incubated with rabbit serum, run 1
(7) Spectra Multicolor Broad Range Protein Ladder, Fermentas
(8) Purified rabbit IgG (50 µg/ml), used in incubation
(9) Rabbit serum (1:50 dilution), used in incubation
(10-11) His$_6$ZQGRep$_4$CT, film, incubated with rabbit IgG, run 2
(12-13) His$_6$ZQGRep$_4$CT, film, incubated with rabbit serum, run 2
(14-15) Rep$_4$CT, film, incubated with rabbit IgG, run 2
(16-17) Rep$_4$CT, film, incubated with rabbit serum, run 2.

Figure 15:
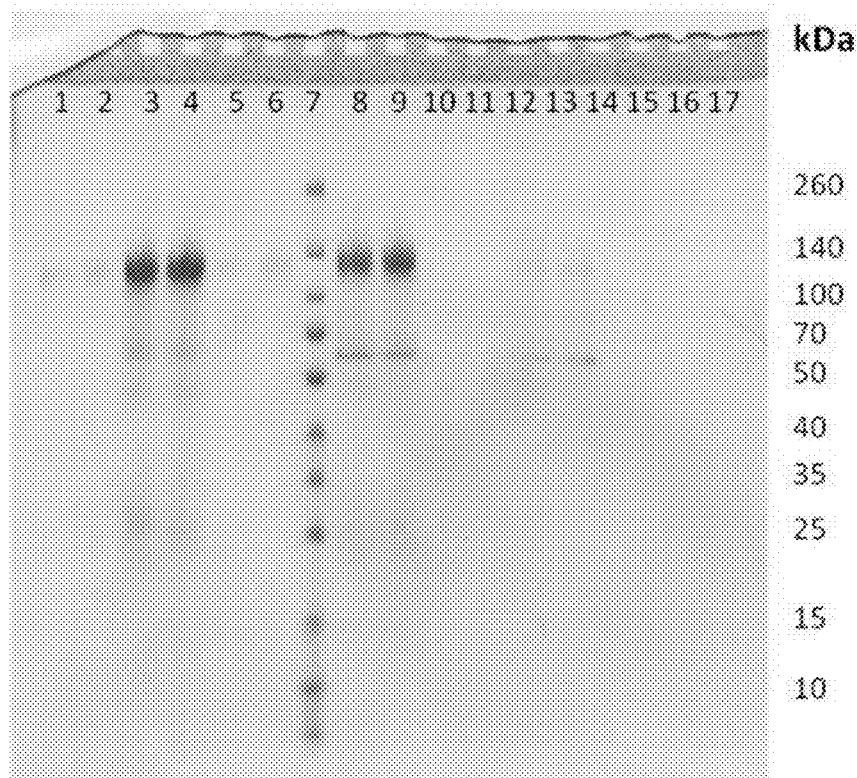

FIG. 15 shows a non-reducing SDS-PAGE gel of eluted fractions, all coming from run 2 and loaded according to:
(1-2) Protein A Sepharose CL-4B matrix, incubated with rabbit IgG
(3-4) Protein A Sepharose CL-4B matrix, incubated with rabbit serum
(5-6) His$_6$ZQGRep$_4$CT, fiber, incubated with rabbit IgG
(7) Spectra Multicolor Broad Range Protein Ladder, Fermentas
(8-9) His$_6$ZQGRep$_4$CT, fiber, incubated with rabbit serum
(10-11) Rep$_4$CT, fiber, incubated with rabbit IgG
(12-13) Rep$_4$CT, fiber, incubated with rabbit serum.

The results in FIG. 13-15 show that the matrices selectively bind IgG from serum. The IgG-binding capacity of all types of His$_6$ZQGRep$_4$CT matrices, i.e. films and fibers, is in the same range as the commercial protein A matrix. Similarly to the commercial protein A matrix, the fusion protein structures can be regenerated with maintained binding capacity.

Example 6

Cleaning-in-Place (CIP) of Fusion Protein Matrices and a Commercial Protein a Matrix To evaluate whether precipitated or denatured substances remain attached to protein structures made of His$_6$ZQGRep$_4$CT (SEQ ID NO: 14) and Rep$_4$CT and to a commercial protein A matrix (Protein A Sepharose CL-4B, GE Healthcare) after elution, a cleaning-in-place (CIP) with 8 M urea was carried out for all the matrices exposed to rabbit serum used in the experiments in Examples 4-5.

Figure 16:
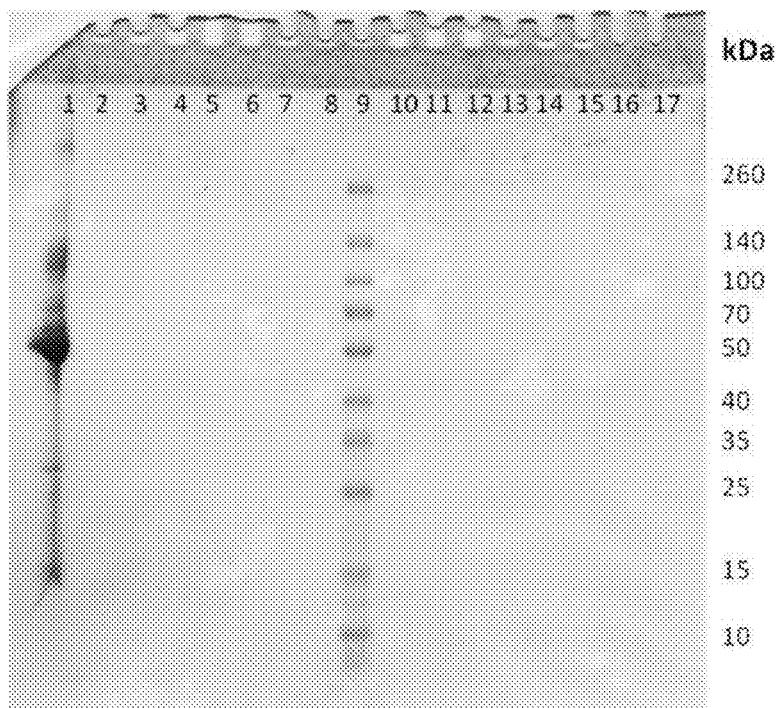
FIGS. 16-17 show non-reducing SDS-PAGE gels of cleaning-in-place (CIP) procedures of fusion protein structures compared to a commercial protein A matrix.
Figure 17:
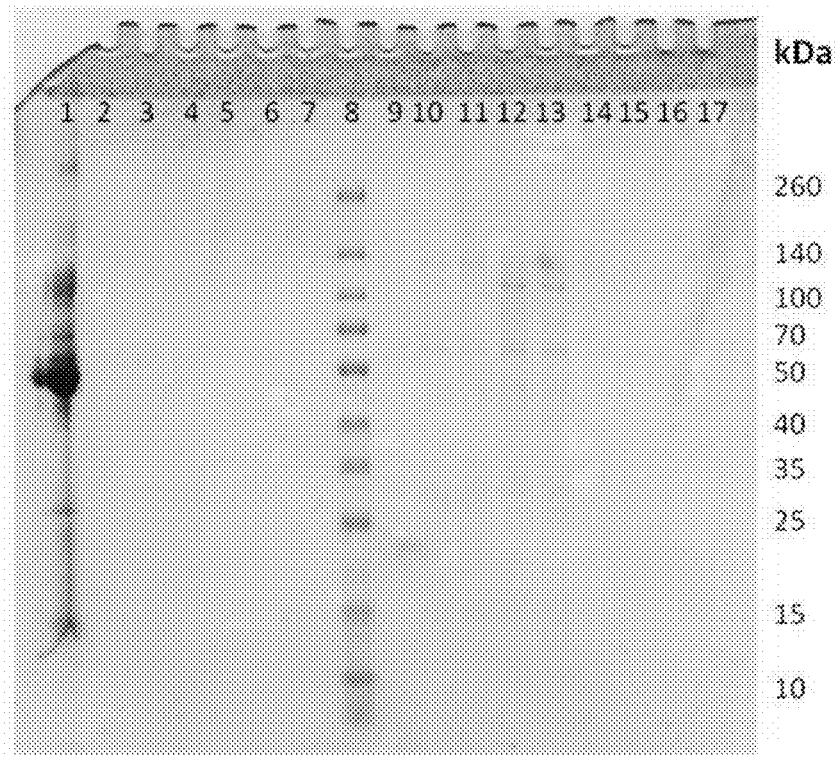

Fibers and films made of His$_6$ZQGRep$_4$CT and Rep$_4$CT from Example 4 and Example 5, and a commercial Protein A matrix from Example 5, all previously exposed to rabbit serum, were immersed in 200 µl of 8 M urea at room temperature for 20 min, prior to supernatant removal, and subsequent analysis of urea fractions on SDS-PAGE under non-reducing conditions (FIG. 16-17).

FIG. 16 shows a non-reducing SDS-PAGE gel from cleaning-in-place with 8 M urea of matrices subjected twice to rabbit serum. The gel was loaded according to:
(1) Rabbit serum (1:50 dilution)
(2) Empty well
(3-5) His$_6$ZQGRep$_4$CT, T film, from Example 4
(6-8) His$_6$ZQGRep$_4$CT, A film, from Example 4
(9) Spectra Multicolor Broad Range Protein Ladder, Fermentas
(10-12) His$_6$ZQGRep$_4$CT, fiber, from Example 4
(13-15) Rep$_4$CT, A film, from Example 4
(16) Rep$_4$CT, fiber, from Example 4
(17) Empty well.

FIG. 17 shows a second non-reducing SDS-PAGE gel from cleaning-in-place with 8 M urea of matrices subjected twice to rabbit serum. The gel was loaded according to:
(1) Rabbit serum (1:50 dilution)
(2) Empty well
(3-4) Rep$_4$CT, fiber, from Example 4
(5-6) His$_6$ZQGRep$_4$CT, film, from Example 5
(7) Rep$_4$CT, film, from Example 5
(8) Spectra Multicolor Broad Range Protein Ladder, Fermentas
(9) Rep$_4$CT, film, from Example 5
(10-11) His$_6$ZQGRep$_4$CT, fiber, from Example 5
(12-13) Rep$_4$CT, fiber, from Example 5
(14-15) Protein A Sepharose CL-4B matrix, from Example 5
(16-17) Empty wells.

The results in FIG. 16-17 indicate that only low amounts of precipitated or denatured substances remain attached to the fusion protein structures after elution and cleaning. In particular, only low amounts of precipitated or denatured substances, in the same range as for the commercial protein A matrix, remain attached to films of the His$_6$ZQGRep$_4$CT fusion protein.

Example 7

Cloning, Expression and Fiber Formation of an Albumin-Binding Fusion Protein

To further prove the fusion protein concept, Rep$_4$CT was produced in fusion with the albumin binding domain (Abd) from streptococcal protein G. Abd is a 5-kDa triple-helix motif that binds albumin. In order to do so a fusion protein consisting of the Abd domain N-terminally to Rep$_4$CT (denoted His$_6$AbdQGRep$_4$CT) was cloned (SEQ ID NOS: 16-17).

Cloning

Primers were designed in order to generate PCR fragments of Abd from a vector containing such a sequence. Also, the primers contained a Protease 3C cleavage site, denoted QG, between Abd and Rep$_4$CT. The resulting PCR products were then treated with the restriction endonucleases NdeI and EcoRI, as was the target vector, denoted pT7His$_6$TrxHis$_6$QGRep$_4$CT (harbouring a kanamycin resistance gene). Upon restriction cleavage of the target vector, the TrxHis$_6$QG part was cleaved off. Cleaved PCR fragments and target vector were joined together with the aid of a T4 DNA Ligase, whereupon the resulting, correctly ligated vector (pT7His$_6$AbdQGRep$_4$CT) was transformed into chemocompetent *E. coli* BL21 (DE3) cells that were allowed to grow onto agar plates supplemented with kanamycin. Colonies were thereafter picked and PCR screened for correct insert and subsequently also sequenced.

Production

*E. coli* BL21 (DE3) cells possessing the pT7His$_6$AbdQGRep$_4$CT vector were grown in Luria-Bertani medium (6 liters in total) supplemented with kanamycin to an OD$_{600}$ of 1-1.5 in 30° C., followed by induction of His$_6$AbdQGRep$_4$CT expression with IPTG and further incubation in 20° C. for approximately 2 h. Next, the cells were harvested by centrifugation, and the resulting cell pellet was dissolved in 20 mM Tris (pH 8.0).

Purification

Cell pellets dissolved in 20 mM Tris (pH 8.0) were supplemented with lysozyme and DNase I in order to completely lyse the bacterial cells, whereupon the supernatants were recovered after 15 000 rpm of centrifugation. Next, the recovered supernatants were loaded onto a Ni IMAC column or a Chelating Sepharose Fast Flow ZN column, keeping the His$_6$AbdQGRep$_4$CT protein bound to the matrix via the His$_6$ tag. After washing, bound proteins were eluted with 20 mM Tris/300 mM imidazole (pH 8.0). The pooled eluate fractions, containing His$_6$AbdQGRep$_4$CT (SEQ ID NO: 16) was dialyzed against 5 liters of 20 mM Tris (pH 8.0), concentrated, and a final amount of 4 mg protein was obtained.

Fiber and Film Formation

From the purified, soluble Abd-Rep$_4$CT protein, both fibers and films were successfully made at a protein concentration of 0.87 mg/ml The fact that macroscopic fibers and films of Abd-Rep$_4$CT were obtained although Rep$_4$CT had been fused to another protein, namely the albumin binding domain (Abd), demonstrates that Rep$_4$CT retains its fiber forming properties despite fused to the Abd domain. Next, the aim was to reveal whether the Abd domain had retained its albumin-binding ability when fused to Rep$_4$CT, see Examples 24 and 25.

Example 8

Cloning, Expression and Fiber Formation of an IgG-Binding Fusion Protein

To further prove the fusion protein concept, Rep$_4$CT was produced in fusion with the IgG binding domain C2 from streptococcal protein G. C2 contains 55 amino acids, and the structure is constituted of two β-hairpins that are associated to form a four stranded mixed antiparallel/parallel β-sheet with a single α-helix lying across one face of the sheet. In order to do so a fusion protein consisting of the C2 domain N-terminally to Rep$_4$CT (denoted His$_6$C2QGRep$_4$CT) was cloned (SEQ ID NOS: 18-19).

Cloning

Primers were designed in order to generate PCR fragments of C2 from a vector containing such a sequence. Also, the primers contained a Protease 3C cleavage site, denoted QG, between C2 and Rep$_4$CT. The resulting PCR products were then treated with the restriction endonucleases NdeI and EcoRI, as was the target vector, denoted pT7His$_6$TrxHis$_6$QGRep$_4$CT (harbouring a kanamycin resistance gene). Upon restriction cleavage of the target vector, the TrxHis$_6$QG part was cleaved off. Cleaved PCR fragments and target vector were joined together with the aid of a T4 DNA Ligase, whereupon the resulting, correctly ligated vector (pT7His$_6$C2QGRep$_4$CT) was transformed into chemocompetent *E. coli* BL21 (DE3) cells that were allowed to grow onto agar plates supplemented with kanamycin. Colonies were thereafter picked and PCR screened for correct insert and subsequently also sequenced.

Production

*E. coli* BL21 (DE3) cells possessing the pT7His$_6$C2QGRep$_4$CT vector were grown in Luria-Bertani medium (6 liters in total) supplemented with kanamycin to an OD600 of 1-1.5 in 30° C., followed by induction of His$_6$C2QGRep$_4$CT expression with IPTG and further incubation in 20° C. for approximately 2 h. Next, the cells were harvested by centrifugation and the resulting cell pellet dissolved in 20 mM Tris (pH 8.0).

Purification

Cell pellets dissolved in 20 mM Tris (pH 8.0) were supplemented with lysozyme and DNase I in order to completely lyse the bacterial cells, whereupon the supernatants were recovered after 15 000 rpm of centrifugation. Next, the recovered supernatants were loaded onto a Ni IMAC column, keeping the His$_6$C2QGRep$_4$CT protein bound to the matrix via the His$_6$ tag. After washing, bound proteins were eluted with 20 mM Tris/300 mM imidazole (pH 8.0). The pooled eluate fractions, containing His$_6$C2QGRep$_4$CT was dialyzed against 5 liters of 20 mM Tris (pH 8.0), concentrated, and a final amount of 6 mg protein was obtained.

Fiber and Film Formation

From the purified, soluble C2-Rep$_4$CT protein, both fibers and films were successfully made at a protein concentration of 0.87 mg/ml. The fact that macroscopic fibers and films of C2-Rep$_4$CT was obtained although Rep$_4$CT had been fused to another protein, namely the IgG binding domain C2, demonstrates that Rep$_4$CT retains its fiber forming properties despite being fused to the C2 domain. Next, the aim was to reveal whether the C2 domain had retained its IgG-binding ability when fused to Rep$_4$CT, see Examples 26 and 27.

Example 9

Cloning, Expression and Formation of Films and Fibers of a Biotin-Binding Fusion Protein Streptavidin is a tetramer of four identical monomers with one binding site per monomer. It shows high affinity towards biotin (vitamin H), reaching a dissociation constant of $K_d \sim 10^{-15}$ M, making this an essentially irreversible binding event. Streptavidin also shows a high stability in presence of proteases, at elevated temperatures and in denaturing agents, and at extreme pH values (Wilchek, M. et al., Anal. Biochem. 171: 1-32 (1988)). Thus, this interaction is attractive in many applications including protein labeling, separation and targeting. In practice, biotinylation is nowadays easily facilitated utilizing biotinylated linker molecules that also houses one out of several reactive organic molecules that attacks and bridge the biotin to different biological molecules, e.g. proteins and DNA. However the production of high density functional surfaces coated with Streptavidin has proven difficult to achieve, see e.g. Table 4. To reduce the binding strengths in applications where reversibility in binding is essential (e.g. during purification) and to be able to successfully express soluble protein in $E.\ coli$, a monomeric variant of streptavidin has been developed, M4 (Wu. S.-C. et al., Protein Expres. Purif. 46, 268-273 (2006)). Compared to the monomers of the wild type tetramer streptavidin, M4 has four amino acid substitutions (V55T, T76R, L109T and V125R), which keep M4 in an active monomeric form.

M4 was N- or C-terminally fused to Rep4CT (SEQ ID NOS: 20-21) by recombinant techniques. The resulting proteins and genes encoding them were named M4Rep4CT (SEQ ID NOS: 22-23), modM4Rep4CT (SEQ ID NOS: 24-25) and Rep4CTM4 (SEQ ID NOS: 26-27), respectively. The difference between M4Rep4CT and modM4Rep4CT is the substitution of a Gly to Arg-Ala-Arg in the linker region between M4 and Rep4CT. All proteins were expressed fused to a His6-Trx-His6 tag that was cleaved off and removed during purification.

Production and purification of all proteins were performed essentially as described in Stark, M. et al., Biomacromolecules 8, 1695-1701 (2007) and Hedhammar M. et al., Biochemistry 47, 3407-3417 (2008). The protein concentration of Rep4CTM4, M4Rep4CT and modM4Rep4CT was measured at 280 nm using a molar extinction coefficient of 53860 $M^{-1}\ cm^{-1}$. The purified protein sample was subjected to reducing SDS-PAGE, and protein purity was determined after staining of the gel with Coomassie Brilliant Blue R-250. The theoretical molecular weights of all the purified proteins and other relevant physical properties are listed in Table 3.

TABLE 3

Physical parameters of the expressed proteins

| Protein | SEQ ID NO | Amino acids (#) | Molecular weight* (g/mol) | Molar extinction coefficient* ($M^{-1}\ cm^{-1}$) |
|---|---|---|---|---|
| Rep4CT | 20 | 263 | 23053 | 11920 |
| Rep4CTM4 | 26 | 428 | 40157 | 53860 |
| M4Rep4CT | 22 | 427 | 40100 | 53860 |
| modM4Rep4CT | 24 | 429 | 40427 | 53860 |

*Theoretical values

From each of the Rep4CTM4, M4Rep4CT and modM4Rep4CT fusion proteins, both film and fibers were formed. These results confirm that Rep4CT retains its ability to self assemble into solid structures although fused to M4. This also confirms that it is possible to obtain fibers and films of proteins where M4 is fused to Rep4CT using linkers of different lengths.

Example 10

Binding of a Biotin-Containing Target to Fusion Protein Fibers and Films (A) Binding of Biotinylated Atto-565 to Rep4CTM4 Films.

Rep4CTM4 (SEQ ID NO: 26) and Rep4CT (SEQ ID NO. 20, control) were allowed to form films by drying 25 µl of protein solution in room temperature in the bottom of wells in clear or black 96 well microtiter plates. The plates were stored at room temperature for one to two weeks before use. The wells were incubated with 100 µl 1% BSA in PBS (pH 7.4) for >1 hour at room temperature in order to avoid non-specific binding. Background values were obtained by measuring fluorescence intensity in the wells with films of the respective protein, Rep4CT or Rep4CTM4, in 50 µl phosphate buffered saline (PBS) prior to addition of biotinylated Atto-565. The wells were further incubated with 50 µl of an 80 µM solution of biotinylated Atto-565 (Sigma Aldrich, Germany) dissolved in 1% BSA in PBS (pH 7.4). The mixture was allowed to stand in room temperature between two to three hours before washing twice with PBS containing 0.05% Tween-20 (PBS-T) and once with PBS. The resulting fluorescence intensity was recorded after adding 50 µl of PBS into the wells in a Tecan Infinite M200 microplate reader ($\lambda_{ex}$=565 nm, $\lambda_{em}$=590 nm).

A dilution series was prepared in PBS, and 50 µl of samples of different concentrations of biotinylated Atto-565 was added to wells with the respective films, in triplicates, whereafter the resulting fluorescence intensity from the wells was recorded.

Figure 18:
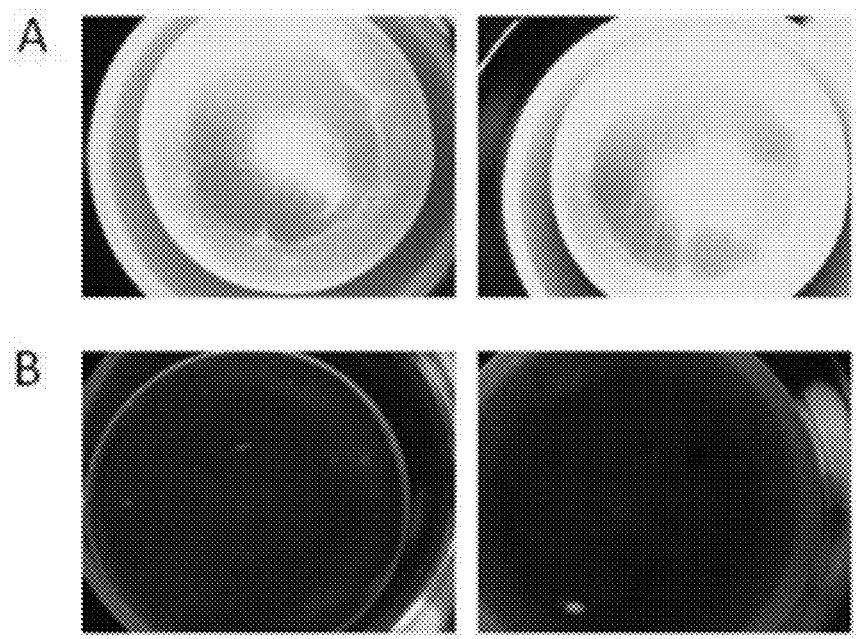
FIG. 18 shows fluorescence intensities from protein films soaked with biotinylated Atto-565.

In FIG. 18, the fluorescence intensities from protein films after soaking with biotinylated Atto-565 and washing are observed in 2× magnification using a Nicon Eclipse Ti—S fluorescence microscope ($\lambda_{ex}$=509-550 nm and $\lambda_{em}$=570-614 nm). The difference in fluorescence intensity between Rep4CTM4 films (panel A) and Rep4CT films (panel B) after addition of biotinylated Atto-565 is evident.

Figure 19:
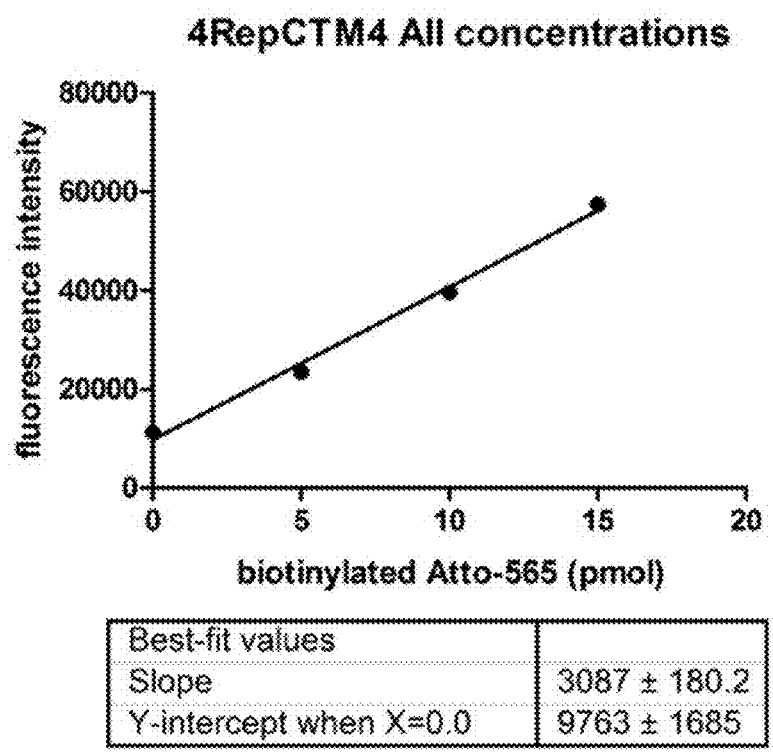
FIG. 19 shows a graph and a linear fit of fluorescence intensity values for different concentrations of biotinylated Atto-565 upon binding to a fusion protein film.

In order to establish the total amount of biotinylated Atto-565 binding to the Rep4CTM4 films, fluorescence intensity was recorded using a dilution series of known amounts of biotinylated Atto-565. In this way, the fluorescence intensities from samples with known amounts (in moles) biotinylated Atto-565 (in triplicates, in wells with Rep4CTM4) were used to obtain a standard curve. The resulting fluorescence intensity values corresponding to background value (Rep4CTM4 films without biotinylated Atto-565) and data points correlating to three concentrations of biotinylated Atto-565 added to the wells are shown in the graph in FIG. 19. The table below the graph in FIG. 19 show the values obtained from a linear regression to the fluorescence intensity values, with standard deviations from measurement in n=3 wells with the same biotinylated Atto-565 concentration.

Figure 20:
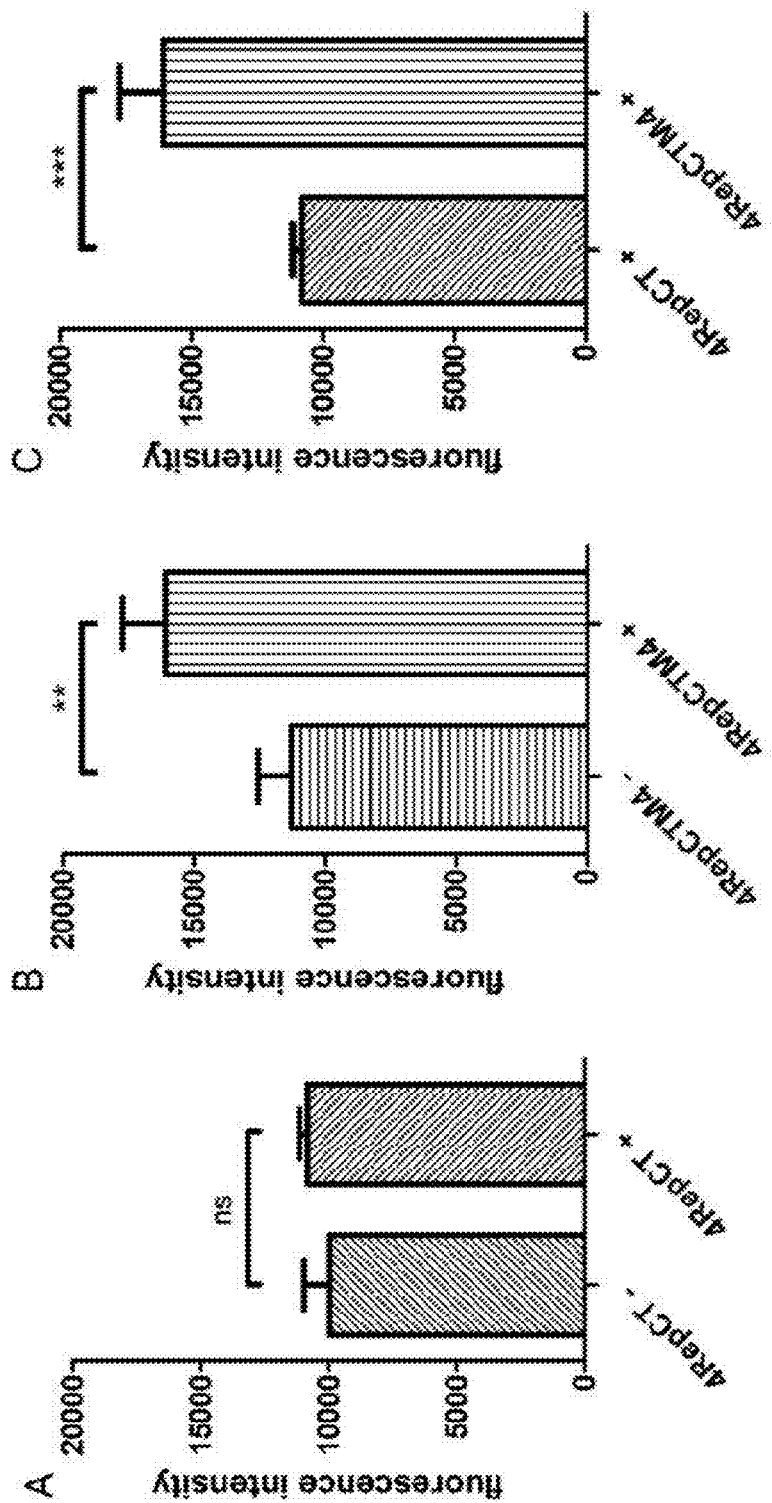
FIG. 20 shows graphs of fluorescence intensity values before (−) and after (+) addition of biotinylated Atto-565 to wells with films made of fusion protein or control.

Starting from the fluorescence intensity values resulting from binding experiments of biotinylated Atto-565 to films of Rep4CTM4 (FIG. 20), these values were used to calculate the amount of moles of biotinylated Atto-565 that correspond to the obtained fluorescence intensity. The resulting fluorescence values are plotted in FIG. 20, with panels A and B displaying values before (−) and after (+) addition of biotinylated Atto-565 to wells with films of Rep4CT (A) and Rep4CTM4 (B). Panel C shows a comparison of the resulting fluorescence intensities after addition of biotinylated Atto- 565 to films of Rep$_4$CT or Rep$_4$CTM4. There was no significant (ns) difference between before and after values for the Rep$_4$CT films (panel A). Significant differences between before and after addition of biotinylated Atto-565 values with Rep$_4$CTM4 (panel B; P<0.01), and between proteins (panel C; P<0.0001), were confirmed by statistical tests. The bars in FIG. 20 indicate standard deviation between fluorescence intensity values of n=10 films.

The biotinylated fluorophore/surface area ratio obtained from the binding experiments was calculated. To surface areas of approximately 28 mm$^2$, 2.1 µmol biotinylated Atto-565 was bound to the Rep$_4$CTM4 films. This results in a bound biotin/surface area of 0.073 µmol/mm$^2$ (Table 5).

(B) Binding of Biotinylated Horse Radish Peroxidase (HRP) to Rep$_4$CTM4 Films

Due to its relatively high stability and the production of chromogenic products in the conversion of a non-chromogenic substrate and peroxide, HRP is commonly used coupled to a secondary antibody or a binder molecule (e.g. biotin) in applications such as ELISAs, Western blots and immuno-histo-chemistry. In order to establish the total amount of biotinylated HRP binding to films made of Rep$_4$CTM4 (SEQ ID NO: 26) and Rep$_4$CT (SEQ ID NO: 20; control), biotinylated HRP was allowed to bind to each respective film. The rate of product formation was recorded at 570 nm using known amounts of substrates. The molar extinction coefficient for the product, resorufin, was obtained from the manufacturer (Invitrogen), stated to be 54000 cm$^{-1}$M$^{-1}$.

Protein solutions (25 µl) of Rep$_4$CTM4 and Rep$_4$CT were allowed to completely dry in the bottom of wells in clear 96 well microtiter plates, thus forming films. The wells were incubated with 100 µl of 1% BSA in PBS (pH 7.4) for >1 hour before incubation with 50 µl of a 0.3 mg/ml biotinylated HRP (Invitrogen, Camarillo, Calif.) in 1% BSA in PBS (pH 7.4) for >1 hour. The wells were subsequently washed twice with PBS-T and once with PBS. Reactions were initiated by addition of 50 µl of a 50 µM Amplex red solution (Invitrogen) with 2 mM hydrogen peroxide dissolved in 0.2% BSA, 28 mM NaCl, 0.54 mM KCl, 0.3 mM KH$_2$PO$_4$, 42 mM Na$_2$HPO$_4$ (pH 7.4) at room temperature. Kinetic measurements were conducted on a Tecan Infinite M200 microplate reader.

Figure 21:
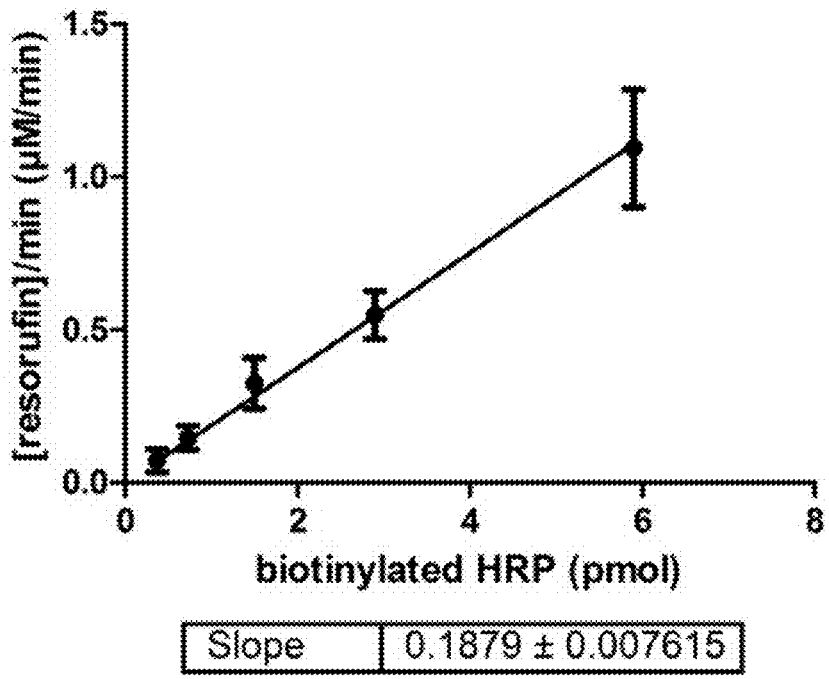
FIG. 21 is a graph showing a standard curve and a linear fit of resulting reaction velocities in catalysis by biotinylated HRP free in solution.

Known amounts of biotinylated HRP (free in solution) were used to establish which amount of HRP that resulted in the same rate of product formation as in measurements with biotinylated HRP on the films. The resulting reaction velocities in catalysis by biotinylated HRP free in solution (pH 7.4) of 50 µM Amplex red and 2 mM hydrogen peroxide to the product, resorufin, are shown in the graph in FIG. 21. Data points correlates to triplicate measurements with the same concentration of biotinylated HRP. The table below the graph in FIG. 21 shows the value obtained from a linear regression to the data. The bars in the graph in FIG. 21 indicate standard deviations from measurements in n=3 wells with the same concentration of biotinylated HRP. The resulting standard curve and slope in FIG. 21 was used for calculation of the amount of biotinylated HRP that was bound to the fusion protein films.

Figure 22:
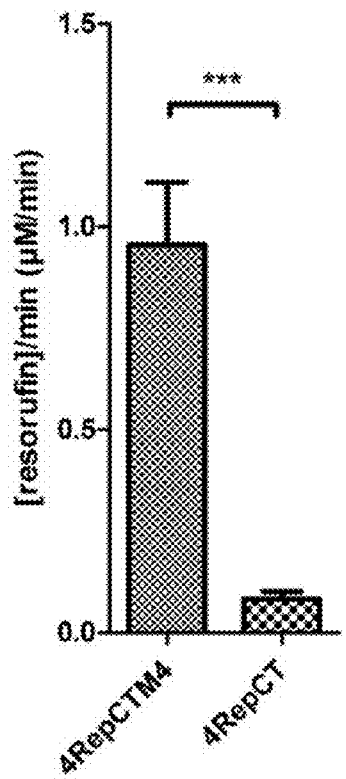
FIG. 22 is a graph showing the reaction velocity in catalysis by biotinylated HRP immobilised to a fusion protein film compared to control.
Figure 23:
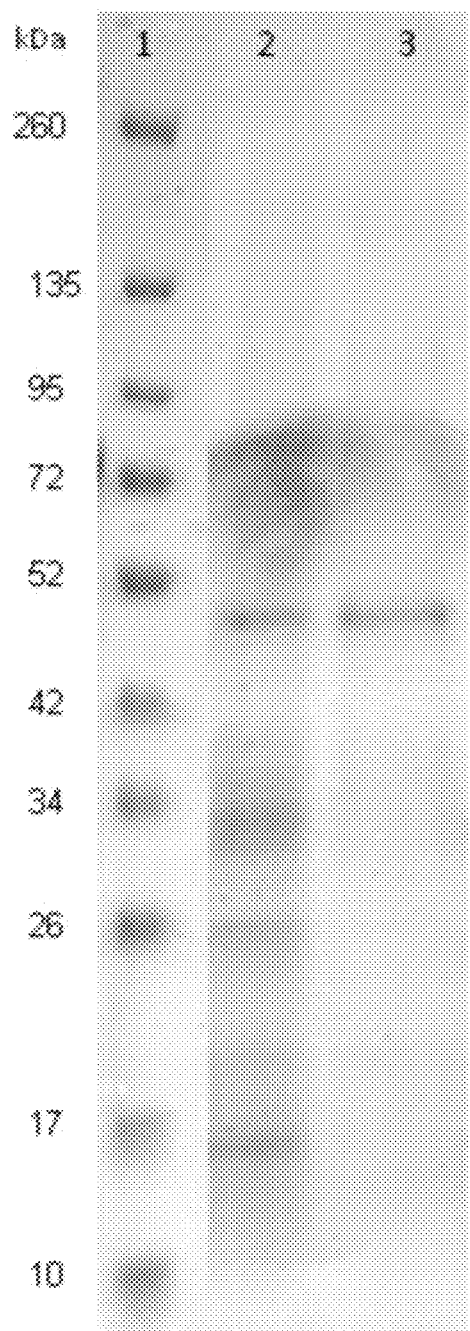
FIG. 23 shows a reducing SDS-PAGE gel of solubilized fusion protein structures.

The reaction velocities in catalysis of 50 µM Amplex red and 2 mM H$_2$O$_2$ in wells where films of the fusion protein and control were incubated with biotinylated HRP is shown in FIG. 22. The reaction velocities in FIGS. 21 and 22 are expressed as the formation of resorufin in µM per minute, calculated using the extinction coefficient provided by Invitrogen (54 000 cm$^{-1}$M$^{-1}$). Bars indicate standard deviation for reactions measured in n=8 wells. FIG. 22 shows a significant difference in rate of product formation (and hence also bound biotinylated HRP) between wells coated with Rep$_4$CTM4 and the controls, Rep$_4$CT-coated wells. It was determined that 0.2 µmol HRP/mm$^2$ was bound to the Rep$_4$CTM4 films, (Table 5).

(C) Comparison with Commercial Products

The production of high density functional surfaces coated with Streptavidin has proven difficult to achieve. The biotin binding capacities of commercially available plates are listed in Table 4.

TABLE 4

Biotin binding capacities of commercially available plates

| Company | Plate | Biotin[a] (pmol) | Coat area[b] (mm$^2$) | Biotin/coat area (pmol/mm$^2$) |
|---|---|---|---|---|
| Nunc/Thermo scientific | Passively Coated plates | 13 | 150 | 0.087 |
| Pierce/Thermo scientific | HBC[c] | 0.78[d]-125 | 90 | 0.008-1.4 |
| Pierce/Thermo scientific | Standard Capacity | 5 | 90 | 0.055 |
| Grenier bio-one | c-bottom | 20 | 210 | 0.096 |
| R&D systems | EvenCoat | 7[e] | 150 | 0.047 |
| Sigma screen/ Sigma Aldrich | S6940 (HBCc) | 300 | 150 | 2.0 |

[a]Biotin-binding capacity as stated by manufacturer
[b]Calculated based on coat volume as stated by manufacturer
[c]HBC = high binding capacity.
[d]The limits were calculated based on stated detection range of a 8 kDa biotinylated molecule.
[e]Calculation based on stated binding of biotinylted antibodies using a MW = 120 kDa.

The biotinylated fluorophore/surface area ratio obtained from the binding experiments with biotinylated Atto-565 in Example 10 A and biotinylated HRP in Example 10 B are summarized in Table 5. The densities of the two different biotinylated molecules on films of Rep$_4$CTM4 (SEQ ID NO: 26) are 0.073-0.2 µmol/mm$^2$.

TABLE 5

Biotin binding capacities of films of M4 fusion protein

| Biotinylated product | Rep$_4$CTM4 (nmol) | Biotinylated molecule (pmol) | Surface area (mm$^2$) | Biotinylated molecule/ surface area (pmol/mm$^2$) | Biotinylated Rep$_4$CTM4 (%) |
|---|---|---|---|---|---|
| Atto-565 | 0.082 | 2.1 | 28 | 0.073 | 2.6 |
| HRP | 0.082 | 5.1 | 28 | 0.2 | 6.2 |

The results in Tables 4-5 indicate that films made of fusion proteins with a M4 moiety provide a biotin binding density in the same ranges as for commercial alternatives, regardless of whether the biotin is coupled to a small (fluorophore) or large (protein) molecule.

Statistics

GraphPad Prism 4.0 (GraphPad Software, San Diego, Calif.) was used for statistical analysis of data. In Example 10 A, a non-parametric paired Wilcoxon test was used in the comparison between fluorescence values before and after addition of biotinylated Atto-565 to films formed from either Rep$_4$CT or Rep$_4$CTM4. Further, a non-parametric, unpaired Mann Whitney U test was used to compare fluorescence intensity in wells after incubation of biotinylated Atto-565 using Rep$_4$CT or Rep$_4$CTM4 film, and also to compare the [resorufin]/min values obtained from measurements on films incubated with biotinylated HRP in Example 10 B. P-values<0.05 were considered significant.

Example 11

Binding of a Biotionylated Antibody and a Secondary Antibody to Fusion Protein Fibers and Films Film and fibers of $Rep_4CT$ (SEQ ID NO: 20, control) and $modM4Rep_4CT$ (SEQ ID NO: 24) are tested for binding capacity to a biotinylated antibody of rabbit origin. The films are formed in 8×1 or 12×1 well strips (wells in equal size to the 96 well microplate formats).

After preincubation of the films and fibers with 1% BSA in PBS (pH 7.4), the biotinylated antibody (rabbit) is incubated with the protein structures (film/fiber) for >1 h, followed by addition of a secondary anti-rabbit antibody, radioactively labeled with $^{125}I$. The films and fibers are washed. Detection of the gamma radiation is carried out on individual films or individual fibers in a gamma counter. A dilution series of known amounts of $^{125}I$-labeled antibody is prepared, and radiation is measured to obtain a standard curve from which the amount of bound biotinylated antibody to the fusion protein films and fibers can be calculated.

Example 12

Preparation of a Pure Film of Fusion Protein

Films were casted using 25 µl of $RepCT_4M4$ (SEQ ID NO: 26) at a concentration of 10-20 µM. 100 μl of PBS (pH 7.4) was allowed to incubate in wells with film for one hour. This solution was removed, and 50 μl hexafluoroisopropanol (HFIP) was added to break the film and solubilize the protein. To additional films, the same amount of HFIP was added without prior washing with PBS. The HFIP was allowed to work on the four films for 3.5 h, and the resulting clear HFIP solution was transferred into Eppendorf tubes containing 50 μl of 20% SDS. The water in the tubes was evaporated, and the remaining content was dissolved in 60 μl 10 mM Tris-HCl (pH 8.0) and subjected to reducing SDS-PAGE.

The results are shown in FIG. 23. Lane 1 corresponds to the proteins in the Spectra™ Multicolor Broad Range Protein Ladder (Fermentas). Numbers correspond to protein sizes. Lane 2 corresponds to purified $Rep_4CTM4$ films that were not soaked with PBS before adding the HFIP. Lane 3 corresponds to a $Rep_4CTM4$ film which has been soaked in PBS for one hour before removing this solution and thereafter adding HFIP.

Although some proteins are co-purified with the $Rep_4CTM4$ protein (lane 2, FIG. 23), incubation with 100 μl PBS for one hour dissolves contaminating proteins leaving a film consisting only of $Rep_4CTM4$ proteins, as judged by reducing SDS-PAGE (lane 3, FIG. 23). Thus, most contaminating proteins are removed by the polymerization process as such, and any remaining impurities in proteins structures made of fusion proteins can easily be removed by gentle washing with aqueous buffers.

Example 13

Capture of Organic Targets in Solution

A $ZRep_4CT$ protein solution (~1 mg/ml) is added to a sample consisting of serum, whereby the IgG molecules in the sample are allowed to bind to the Z moiety of the fusion protein in solution. The mixture is subjected to a hydrophobic/hydrophilic interface which causes the $Rep_4CT$ part of the fusion protein/Ig G complex to form a film or a foam, leaving other serum proteins in solution and capturing the IgG on a solid structure.

Alternatively, the mixture is allowed to dry on a solid support, forming a film with immobilized IgG. This film is washed with a buffer, e.g. PBS, to dissolve and remove contaminating proteins.

Alternatively, fibers are formed by providing a hydrophobic-hydrophilic interface and subjecting the mixture to shear forces. The $Rep_4CT$ part of the fusion protein/IgG complex polymerises into macroscopic fibers, leaving other proteins in the solution.

The solid structures formed (films, foams or fibers) may be collected, and the IgG can be recovered in a suitable elution buffer (e.g. by lowering the pH to 2.7). Eluted proteins are identified on SDS-PAGE. See also Example 22.

Example 14

Fusion Protein Scaffolds for Cell Capture (A) In Vivo Studies of Non Adherent Cells in the Anterior Chamber of the Eye $ZRep_4CT$ fibers/films/foams are allowed to incubate with IgG against CD45 or CD34. Leucocytes are captured to $ZRep_4CT$ scaffolds with IgG against CD45 and mast cells are captured on $ZRep_4CT$ scaffolds with IgG against CD34. The cells are allowed to immobilize onto the scaffold. The cells and the fusion protein scaffolds are transplanted into the anterior chamber of the eye of a naked mice. The cells are inspected in vivo through the eye window.

(B) In Vitro Studies of Non-Adherent Cells

Mast cells and leucocytes are grown on $ZRep_4CT$ scaffolds with IgG against CD34 and CD45 respectively, and then monitored in vitro. Some cells are non adherent in a phase during development, e.g. neural stem cells that can grow in clusters. In the neural clusters the cells stay in a non-differentiated form. Neural stem cells are grown in clusters on $ZRep_4CT$ scaffolds with IgG against a cell receptor on the neural stem cells.

(C) Selection of Specific Cells

A $ZRep_4CT$ scaffold (film/foam/fiber) is used for selection of cells through specific antibodies. Mast cells are selected in a two step procedure. Step 1: Binding of cells onto a $ZRep_4CT$ scaffolds with IgG against CD34. Step 2: Selection of mast cells on $ZRep_4CT$ scaffolds with IgG against the C-kit receptor.

(D) Protein Production in Eukaryotic Cells Grown on $ZRep_4CT$

Many cells used for protein production are derived from non-adherent cell lines. However, large scale production is in many ways facilitated when adherent cells are used, as the physical separation is facilitated. By the use of a $ZRep_4CT$ scaffold with IgG against a cell receptor, growth of non-adherent cells can be done in adherent way.

Example 15

Investigation of the Influence of Urea Treatment on IgG Binding to $Z\text{-}Rep_4CT$ The effect of urea treatment of $Z\text{-}Rep_4CT$ films and fibers on IgG binding was here evaluated. Films and fibers of $Z\text{-}Rep_4CT$ were treated with urea prior to binding of IgG from rabbit serum. Bound IgG was eluted and analyzed by SDS-PAGE.

Fibers and films of Z-Rep$_4$CT, which in Example 6 were observed to bind IgG from rabbit serum and were treated with 8 M urea (200 µl 8 M urea, 20 min, room temperature), were incubated with 500 µl rabbit serum (1:5 dilution) for 1 h at room temperature. Films and fibers of Rep$_4$CT (SEQ ID NO: 20) were used as control material, and were treated in the same way. After washing three times with 600 µl PBS, bound IgG was eluted in 500 µl by lowering the pH to approximately 2.7 with elution buffer (0.5 M acetic acid, 1 M urea, 100 mM NaCl), after which the eluted fractions were analyzed by non-reducing SDS-PAGE (not shown).

It was concluded from the gel that films and fibers of Z-Rep$_4$CT retain their binding capacity for IgG after treatment with 8 M urea. Control films and fibers of Rep$_4$CT did not show any IgG binding.

Example 16

Investigation of the Influence of NaOH Treatment on IgG Binding to Z-Rep$_4$CT

To further evaluate durability to cleaning conditions, the effect of NaOH treatment of Z-Rep$_4$CT (SEQ ID NO: 14) films and fibers on IgG binding was evaluated. Fibers and films of Z-Rep$_4$CT from Example 4 and 5, which in Example 6 were observed to bind IgG from rabbit serum and were treated with 8 M urea (200 µl 8 M urea, 20 min, room temperature), were now further treated with 1 M NaOH (500 µl 1 M NaOH, 20 min, room temperature). Films and fibers of Rep$_4$CT (SEQ ID NO: 20) were used as control material, and were treated in the same way. After NaOH treatment, the films and fibers were incubated with 500 µl rabbit serum (1:5 dilution) for 1 h at room temperature. After washing three times with 600 µl PBS, bound IgG was eluted in 500 µl by lowering the pH to approximately 2.7 with elution buffer (i.e. 0.5 M acetic acid, 1 M urea, 100 mM NaCl), after which the eluted fractions were analyzed by non-reducing SDS-PAGE (not shown).

It was concluded from the gel that films and fibers of Z-Rep$_4$CT retain their binding capacity for IgG after treatment with 1 M NaOH. Control films and fibers of Rep$_4$CT did not show any IgG binding.

Example 17

Quantification of IgG-HRP Binding to Z-Rep$_4$CT Films (A) IgG-HRP Binding to Z-Rep$_4$CT Films In order to quantify the IgG binding to Z-Rep$_4$CT, horseradish peroxidase (HRP) conjugated IgG (IgG-HRP) was bound to Z-Rep$_4$CT films.

Films of Z-Rep$_4$CT (SEQ ID NO: 14) and Rep$_4$CT (control, SEQ ID NO: 20) at different concentrations (0.011-890 pmoles) were casted in 96-well plates). The films were blocked with 100 µl 1% BSA for 1 h at room temperature. The films were then incubated for 1 h at room temperature in 50 µl IgG-HRP (i.e. 34 pmole IgG-HRP, rabbit source IgG), and the films were washed twice with 100 µl 0.05% Tween, followed by a final wash with 100 µl of PBS. To measure bound IgG-HRP to films, 50 µl of 50 µM Amplex Red/2 mM H$_2$O$_2$ was added to one film at a time, followed by monitoring of the absorbance at 570 nm for three minutes at a Tecan Plate Reader. A dilution series of soluble IgG-HRP (0.05-0.5 pmole) was also measured in the same type of plate as for the films, by blocking the wells with 100 µl 1% bovine serum albumin (BSA) for 1 h, prior to addition of 20 µl soluble IgG-HRP, 20 µl 125 µM Amplex Red and 10 µl 9.79 mM H$_2$O$_2$. Triplicate measurements were performed for the films and the dilution series.

A linear regression fit was made using Tecan software for each individual measurement, corresponding to the linear region of the absorbance at 570 nm (Abs570/min) versus time raw data plot. The slope corresponds to the HRP conversion rate of colorless substrate to colored product, and is proportional to the number of bound IgG-HRP molecules.

For each individual triplicate, a mean value and a standard deviation of the amount of bound IgG-HRP (pmole) was calculated. FIG. 24 A shows the amount of IgG-HRP bound to Z-Rep$_4$CT and Rep$_4$CT films of different protein concentrations, and FIG. 24 B shows the fractions of Z-Rep$_4$CT and Rep$_4$CT molecules in films of different protein concentrations that have bound IgG-HRP.

For films containing 1.1 pmole of protein and more, Z-Rep$_4$CT films bind significantly more IgG-HRP than the corresponding Rep$_4$CT control films. The fraction of Z-Rep$_4$CT molecules in these films that have bound IgG-HRP is approximately ~7% or less.

(B) IgG-HRP Binding to Z-Rep$_4$CT Films after NaOH Treatment

To investigate the effect of NaOH treatment on IgG binding to Z-Rep$_4$CT films, IgG-HRP was bound to NaOH treated films and the amount of bound IgG-HRP detected.

Films of Z-Rep$_4$CT (SEQ ID NO: 14; 1.1-890 pmole) and Rep$_4$CT (SEQ ID NO: 20, 108 pmole) with bound IgG-HRP from Example 17 (A) were incubated in 100 µl of elution buffer (pH 2.7) for 1 h at room temperature in order to remove the bound IgG-HRP. Next, the films were incubated in 100 µl of 1 M NaOH for 20-30 min at room temperature, followed by washing twice in 150 µl PBS. The wells containing the films were then blocked with 1% BSA, incubated with IgG-HRP (34 pmole) and washed three times, prior to addition of 50 µM Amplex Red/2 mM H$_2$O$_2$ and subsequent monitoring of the absorbance at 570 nm as set out above in (A). For each individual triplicate, a mean value and a standard deviation of the amount of bound IgG-HRP (pmole) was calculated.

Figure 26:
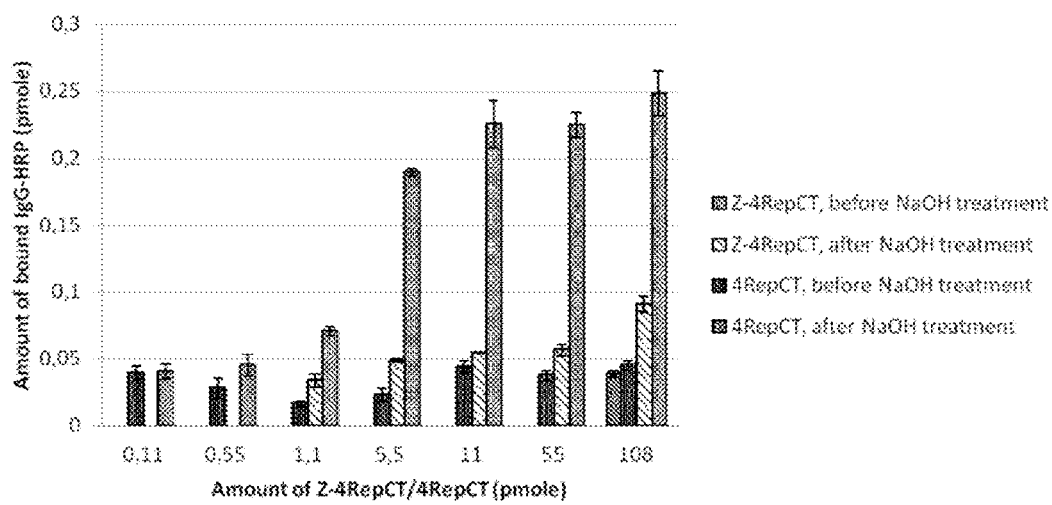

FIG. 25 A shows the amount of IgG-HRP bound to Z-Rep$_4$CT and Rep$_4$CT films of different protein concentrations, and FIG. 25 B shows the fractions of Z-Rep$_4$CT and Rep$_4$CT molecules in films of different protein concentrations that have bound IgG-HRP. FIG. 26 visualizes the amounts of bound IgG-HRP, before and after NaOH treatment, to Z-Rep$_4$CT and Rep$_4$CT films.

The 108 pmole Z-Rep$_4$CT films show significantly more binding than the corresponding Rep$_4$CT films, and the amount of Z-Rep$_4$CT binding of IgG-HRP to NaOH treated films show a trend to increase as the amount of protein in the film increases. It seems that the amount of bound IgG-HRP to Z-Rep$_4$CT films is reduced approximately 2-4-fold by the harsh 1 M NaOH treatment compared to untreated films.

Example 18

Quantification of IgG-Fluorophore Binding to Z-Rep$_4$CT Films

Binding of IgG conjugated to a fluorophore was performed to Z-Rep$_4$CT and Rep$_4$CT films containing different amounts of protein.

Films of Z-Rep$_4$CT (SEQ ID NO: 14) and Rep$_4$CT (control, SEQ ID NO: 20) at different concentrations (0.011-890 pmoles) were prepared and blocked as set out in Example 17. The films were then incubated for 1 h at room temperature in 50 µl IgG-fluorophore (100 pmole IgG-fluorophore, rabbit source IgG, fluorophore: Alexa Fluor 633), after which the films were washed two times with 100 µl 0.05% Tween, followed by a final wash with 100 µl of PBS. Before fluorescence measurements, 100 µl PBS was added to each film.

A dilution series of soluble IgG-fluorophore (0-1 pmole) was also measured in the same type of plate as for the films, by blocking the wells with 100 µl 1% bovine serum albumin (BSA) for 1 h, prior to addition of 100 µl soluble IgG-fluorophore. The fluorescence was measured as triplicates for films and the dilution series on a Tecan Plate Reader instrument (excitation: 632 nm, emission: 660 nm, Gain: 200).

For each individual triplicate, a mean value and a standard deviation of the amount of bound IgG-fluorophore (pmole) were calculated (FIG. 27 A) for films with 0.011-55 pmole protein. The fraction of Z-Rep$_4$CT and Rep$_4$CT molecules binding IgG-fluorophore was also calculated (FIG. 27 B).

It can be concluded that there is significantly more binding of IgG-Alexa Fluor 633 to Z-Rep$_4$CT films than to the corresponding Rep$_4$CT control films. No significant difference in IgG-fluorophore binding between 0.011-11 pmole Z-Rep$_4$CT films is observed, and this does not seem to be due to autofluorescence of Z-Rep$_4$CT films alone at this wavelength (data not shown). The IgG-fluorophore binding to Z-Rep$_4$CT films containing more than 55 pmole of protein could not be calculated in any reliable way, because the fluorescence signals from those were outside the calibration curve.

By comparing the amounts of bound IgG-fluorophore by Z-Rep$_4$CT films with the corresponding binding of IgG-HRP in Example 17, Z-Rep$_4$CT seems to bind more IgG-fluorophore than IgG-HRP (e.g. ~4- and ~6-fold difference for 55 and 1.1 pmole films, respectively), which may be due to the difference in size between the fluorophore and HRP. Furthermore, the fraction of Z-Rep$_4$CT molecules binding IgG-fluorophore also seems to have increased compared to those of IgG-HRP binding.

Example 19

Binding of IgG from Human Blood Plasma to Z-Rep$_4$CT Films

In this experiment, three films of Z-Rep$_4$CT (SEQ ID NO: 14) were prepared as set out in Example 3. All films had been stored, after they were casted, for eight months in +4° C. without being immersed in any liquid during storage. Each Z-Rep$_4$CT film was incubated with 500 µl of human blood plasma (1:5 dilution) for 1 h at room temperature. After washing three times with 600 µl PBS, bound IgG was eluted in 500 µl by lowering the pH to approximately 2.7 with elution buffer (0.5 M acetic acid, 1 M urea, 100 mM NaCl), after which the eluted fractions were analyzed by non-reducing SDS-PAGE (not shown). Films of Rep$_4$CT (SEQ ID NO: 20) were used as control material, and were treated in the same way.

It is evident from the gel that IgG (~146 kDa) appears in the eluted fractions from Z-Rep$_4$CT films, indicating that films of Z-Rep$_4$CT have retained the ability to bind IgG from human blood plasma after eight months of storage in +4° C., without being immersed in any liquid. The control films of Rep$_4$CT do not show any IgG in the eluted fractions. These findings extend the observations of experimental reproducibility reported in Example 4 when using the structures according to the invention, and also show that the protein structures can bind human IgG.

Example 20

Binding of IgG from Human Blood Plasma to an Autoclaved Z-Rep$_4$CT Fiber

The ability of Z-Rep$_4$CT to bind IgG after sterilization by autoclave treatment was investigated. After autoclave treatment of a Z-Rep$_4$CT fiber, the fiber was allowed to bind IgG from human blood plasma. The IgG binding of the autoclaved fiber was compared to that of a non-autoclaved fiber.

Two approximately equally sized Z-Rep$_4$CT (SEQ ID NO: 14) fibers were transferred to two tubes containing 20 mM Tris (pH 8). One of the fibers was then autoclaved for 20 min at 121° C. Two Rep$_4$CT (SEQ ID NO: 20) fibers were used as control material, and were treated in the same way.

The fibers were incubated with 500 µl of human blood plasma (1:5 dilution) for 1 h at room temperature. After washing three times with 600 µl PBS, bound IgG was eluted in 500 µl by lowering the pH to approximately 2.7 with elution buffer (0.5 M acetic acid, 1 M urea, 100 mM NaCl), after which the eluted fractions were analyzed by non-reducing SDS-PAGE (FIG. 28).

The gel shown in FIG. 28 was loaded according to:
(1) Human blood plasma (1:5), 1.4 µl loaded
(2) Z-Rep$_4$CT, non-autoclaved fiber, 14 µl loaded
(3) Z-Rep$_4$CT, autoclaved fiber, 14 µl loaded
(4) Rep$_4$CT, non-autoclaved fiber, 14 µl loaded
(5) Rep$_4$CT, autoclaved fiber, 14 µl loaded
(6) Molecular weight marker.

Both the non-autoclaved and the autoclaved Z-Rep$_4$CT fiber show a clear IgG band around 146 kDa. There is no obvious difference in the strength of these IgG bands, suggesting that autoclave treatment has little effect on IgG binding ability. Neither non-autoclaved nor autoclaved fibers of Rep$_4$CT show any IgG in the eluted fractions. All fibers show an additional, much weaker, albumin band (~50-60 kDa).

Example 21

Protease 3C Cleavage of Z-Rep$_4$CT Fibers

The Z-Rep$_4$CT protein (full protein architecture being His$_6$-Z-LEALFQGP-Rep$_4$CT; SEQ ID NO: 14) contains a Protease 3C recognition site (LEALFQGP, Protease 3C cleaving between the amino acids Q and G) between the Z domain and the Rep$_4$CT segment.

An arbitrary sized Z-Rep$_4$CT fiber was transferred to an Eppendorf tube, and protease cleavage was started by adding 9.6 µg of Protease 3C and 0.35 µl of 1 M DTT (dithiothreitol) to a total volume of 350 µl. The cleavage was allowed to proceed for 24 h at +4° C., after which a sample for SDS-PAGE was withdrawn from the cleavage supernatant. The cleavage was then allowed to proceed for another 24 h (+4° C.) when a second sample for SDS-PAGE was withdrawn from the cleavage supernatant. The two withdrawn samples were then analysed by SDS-PAGE (FIG. 29).

The gel shown in FIG. 29 was loaded according to:
(1), molecular weight marker
(2), supernatant of the Z-Rep$_4$CT fiber cleaved with Protease 3C for 24 h
(3), supernatant of the Z-Rep$_4$CT fiber cleaved with Protease 3C for 48 h.

It can be seen from FIG. 29 that both supernatants after cleavage of a Z-Rep$_4$CT fiber with Protease 3C contained two distinct bands. The first band, slightly below 35 kDa, corresponds to Protease 3C (~31 kDa), while the second band is situated just above 10 kDa. Since cleavage of Z-Rep$_4$CT by Protease 3C would generate two oligopeptide segments corresponding to (i) His$_6$-Z-LEALFQ (~9 kDa) and (ii) GP-Rep$_4$CT (~23 kDa), it is concluded that the second band corresponds to the cleaved-off HZ fragment (9 kDa). It is therefore concluded that the Protease 3C cleavage site is available for cleavage in Z-Rep$_4$CT fibers and therefore, the HZ part can be removed.

Example 22

Fiber Formation of Soluble Z-Rep$_4$CT in the Presence of IgG

When mixing soluble Z- depletion was achieved by transferring the cell suspension to a T-75 tissue culture flask, followed by incubation 90 min at 37° C. After monocyte depletion, cells in suspension were recovered and the total number of lymphocytes was counted to $11 \times 10^6$.

In order to bind lymphocytes to Z-Rep$_4$CT (SEQ ID NO: 14) matrices, lymphocytes (1 ml, ~$0.37 \times 10^6$ cells/ml) were applied to fibers and films, followed by incubation for 30 min at +4° C. (with gentle wobbling). Next, fibers and films were washed three times with 3 ml of PBS/2% FCS (pH 7.4). Bound cells were fixated in 2% PFA (ParaFormAldehyde) for 15 min at +4° C. Cell nuclei were stained by immersing fibers and films with bound cells in 200 µl of DAPI (1 µg/ml) staining solution for 5 min at room temperature prior to washing three times with 300 µl PBS. PBS at a volume of 300 µl was added to each fiber and film before fluorescence microscopy analysis using an inverted Nikon Eclipse Ti instrument (excitation at 380-395 nm, detection at 415-475 nm).

The pictures of Z-Rep$_4$CT fibers (not shown) show a few bound lymphocyte cells for the fiber that has not been exposed to anti-human CD3 IgG antibodies, whereas the fiber that has been exposed to IgG seem to have bound more lymphocytes. In the case of Z-Rep$_4$CT films, stained cells are clearly visible for the film exposed to IgG, but also for the film not exposed to IgG. However, also for the films, it seems like the film exposed to anti-human CD3 IgG prior to cell binding has more cells bound than the corresponding film not exposed to IgG before cell binding. Moreover, control fibers and films of Rep$_4$CT (SEQ ID NO: 20) do not show any lymphocyte binding at all.

In this experiment, it has been shown by fluorescence microscopy that fibers and films of Z-Rep$_4$CT, in contrast to those of Rep$_4$CT, have the ability to bind a fluorescently labeled IgG antibody, namely mouse anti-human CD3 IgG. Furthermore, both Z-Rep$_4$CT fibers and films have the ability to bind lymphocytes, regardless of possessing the IgG antibody specifically recognizing human T lymphocytes or not. This could imply that the Z domain itself has some affinity for human lymphocytes. However, the number of bound cells to Z-Rep$_4$CT matrices seems to be slightly increased when coated with IgG prior to cell binding. To be able to know if the bound cells are lymphocytes of T type, it is necessary to apply a second antibody also directed to the human CD3 molecule, in order to distinguish T lymphocytes from other types of lymphocytes (e.g. B lymphocytes and NK cells).

Example 24

Binding of Albumin from Human Plasma to Abd-Rep$_4$CT Films

To evaluate the accessibility of the Abd domain (residues 13-58 in SEQ ID NO: 16) in the films, and the ability of Abd-Rep$_4$CT films to bind albumin, human blood plasma was used as albumin source. Bound albumin was eluted and analyzed by SDS-PAGE.

Six films of Abd-Rep$_4$CT (SEQ ID NO: 16) prepared in Example 7 were incubated with 500 µl of human blood plasma (1:5 dilution) for 1 h at room temperature. After washing three times with 600 µl PBS, bound albumin was eluted in 500 µl by lowering the pH to approximately 2.7 with elution buffer (0.5 M acetic acid, 1 M urea, 100 mM NaCl), after which the eluted fractions were analyzed by non-reducing SDS-PAGE (FIG. 31). Films of Rep$_4$CT (SEQ ID NO: 20), also prepared in Example 7, were used as control material, and were treated in the same way.

The gel shown in FIG. 31 was loaded according to:
(1) Human blood plasma (1:50), 0.7 µl loaded
(2-7) Hexaplicate of Abd-Rep$_4$CT, film, 14 µl loaded
(8) Empty well incubated with human blood plasma, 14 µl loaded
(9) Molecular weight marker
(10-12) Triplicates of Rep$_4$CT, film, 14 µl loaded.

All six films of Abd-Rep$_4$CT have bound albumin from human blood plasma (lanes 2-7). As only a single albumin band (~60 kDa) appears in the eluted fraction of these Abd-Rep$_4$CT films, they seem to not bind anything unspecifically from the human blood plasma. Films of Rep$_4$CT do not show any albumin in the eluted fractions (lanes 10-12).

To investigate the stability of the films, the albumin binding ability of Abd-Rep$_4$CT films that had been used once before (see above), and had been stored 29 days in PBS (+4° C.) was tested again. The six films of Abd-Rep$_4$CT were incubated with 500 µl of human blood plasma (1:5 dilution) for 1 h at room temperature. After washing three times with 600 µl PBS, bound albumin was eluted in 500 µl by lowering the pH to approximately 2.7 with elution buffer (0.5 M acetic acid, 1 M urea, 100 mM NaCl), after which the eluted fractions were analyzed by non-reducing SDS-PAGE (not shown). Films of Rep$_4$CT were used as control material, and were treated in the same way.

All six films of Abd-Rep$_4$CT retained the ability to bind albumin from human blood plasma after storage for 29 days in PBS. Films of Rep$_4$CT did not show any albumin in the eluted fractions.

Example 25

Cleaning of Abd-Rep$_4$CT Films (A) Urea Treatment of Abd-Rep$_4$CT Films
Films of Abd-Rep$_4$CT (SEQ ID NO: 16) (six films in total, previously used in Example 24) were incubated with 500 µl of 8 M urea for 20 min in room temperature, after which they were washed three times in 600 µl PBS. Next, the films were incubated in 500 µl of human blood plasma (1:5 dilution) for 1 h at room temperature. After washing three times with 600 µl PBS, bound albumin was eluted in 500 µl by lowering the pH to approximately 2.7 with elution buffer (i.e. 0.5 M acetic acid, 1 M urea, 100 mM NaCl), after which the eluted fractions were analyzed by non-reducing SDS-PAGE (not shown). All six films of Abd-Rep$_4$CT can still bind albumin from human blood plasma after treatment with 8 M urea.
(B) NaOH Treatment of Abd-Rep$_4$CT Fibers and Films
A fiber of Abd-Rep$_4$CT (SEQ ID NO: 16) was first incubated in 500 µl of human blood plasma (1:5 dilution) for 1 h at room temperature. After washing three times with 600 µl PBS, bound albumin was eluted in 500 µl by lowering the pH to approximately 2.7 with elution buffer (0.5 M acetic acid, 1 M urea, 100 mM NaCl), after which the eluted fraction was analyzed by non-reducing SDS-PAGE. The same procedure was carried out for a Rep$_4$CT (SEQ ID NO: 20) control fiber.

For treatment with NaOH, triplicates of three sets of Abd-Rep$_4$CT (SEQ ID NO: 16) films were used: (i) films previously treated with 8 M urea (see (A) above) that are treated with 1 M NaOH, followed by albumin binding; (ii) previously unused films that are treated with 1 M NaOH, followed by albumin binding; and (iii) previously unused films that are only analyzed for albumin binding. The Abd-Rep$_4$CT fibers used above for albumin binding are treated with 1 M NaOH, followed by albumin binding again.

For treatment with NaOH, the Abd-Rep$_4$CT fiber and films [film sets (i) and (ii)] were incubated with 500 µl of 1 M NaOH for ~20 min in room temperature, after which they were washed three times in 600 μl PBS. Next, the fiber and all three sets of films were incubated in 500 μl of human blood plasma (1:5 dilution) for 1 h at room temperature. After washing three times with 600 μl PBS, bound albumin was eluted in 500 μl by lowering the pH to approximately 2.7 with elution buffer (0.5 M acetic acid, 1 M urea, 100 mM NaCl), after which the eluted fractions were analyzed by non-reducing SDS-PAGE (FIG. 32).

The gel in FIG. 32 was loaded according to:
(1) Human blood plasma (1:5), 1.4 μl loaded
(2-3, 5) Triplicate of Abd-Rep$_4$CT film, treated with 8 M urea and 1 M NaOH before albumin binding, 14 μl loaded
(4) Molecular weight marker
(6-8) Triplicate of Abd-Rep$_4$CT film, untreated before albumin binding, 14 μl loaded
(9-11) Triplicate of Abd-Rep$_4$CT film, treated with 1 M NaOH before albumin binding, 14 μl loaded
(12) Abd-Rep$_4$CT fiber, untreated before albumin binding, 14 μl loaded
(13) Abd-Rep$_4$CT fiber, treated with 1 M NaOH before albumin binding, 14 μl loaded
(14) Rep$_4$CT fiber, untreated before albumin binding, 14 μl loaded.

The Abd-Rep$_4$CT fiber clearly binds albumin (~60 kDa) both before and after treatment with 1 M NaOH (lane 12 and 13, respectively), whereas the corresponding untreated Rep$_4$CT fiber does not show any albumin binding (lane 14). All Abd-Rep$_4$CT films show albumin binding with no obvious difference in band strength between the untreated films and the films treated with 1 M NaOH before albumin binding (lanes 6-8 and 9-11, respectively). However, the films treated with both 8 M urea and 1 M NaOH before albumin binding show a decrease in the strength of the eluted albumin bands (lanes 2, 3 and 5) compared to the other two sets of films.

Example 26

Binding of Rabbit and Mouse IgG to C2-Re 4CT Films and Fibers

Figure 33:
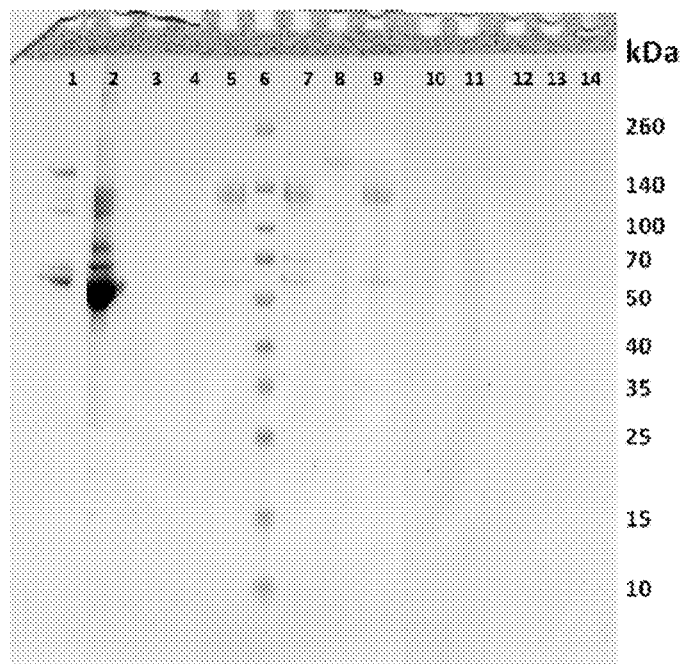
FIG. 33-34 shows non-reducing SDS-PAGE gels illustrating the functionality of the C2 domain in fusion protein structures.

The accessibility of the C2 domain (residues 13-67 in SEQ ID NO: 18) in C2-Rep$_4$CT fibers and films was analysed as follows. Two films and one fiber of C2-Rep$_4$CT (SEQ ID NO: 18) were incubated with 500 μl rabbit serum (1:5 dilution), while another two films and one fiber of C2-Rep$_4$CT (SEQ ID NO: 18) were incubated with 500 μl of ~50 μg/ml mouse IgG$_1$ (monoclonal anti-rabbit immunoglobulins, mouse IgG$_1$ isotype, mouse ascites fluid) for 1 h at room temperature. After washing three times with 600 μl PBS, bound IgG was eluted in 500 μl by lowering the pH to approximately 2.7 with elution buffer (0.5 M acetic acid, 1 M urea, 100 mM NaCl), after which the eluted fractions were analyzed by non-reducing SDS-PAGE (FIG. 33). Films and fibers of Rep$_4$CT (SEQ ID NO: 20) were used as control material, and were treated in the same way.

The gel of FIG. 33 was loaded according to:
(1) Mouse ascites fluid (isotype IgG$_1$)
(2) Rabbit serum (1:50)
(3-4) Duplicates of C2-Rep$_4$CT, film, mouse IgG$_1$
(5, 7) Duplicates of C2-Rep$_4$CT, film, rabbit serum
(6) Molecular weight marker
(8) C2-Rep$_4$CT, fiber, mouse IgG$_1$
(9) C2-Rep$_4$CT, fiber, rabbit serum
(10-11) Duplicates of Rep$_4$CT, film, mouse IgG$_1$
(12) Rep$_4$CT, film, rabbit serum
(13) Rep$_4$CT, fiber, rabbit serum
(14) Rep$_4$CT, fiber, mouse IgG$_1$
[Note: Rabbit IgG is ~146 kDa and mouse IgG is ~160 kDa under non-reducing SDS-PAGE conditions.]

Binding of mouse IgG$_1$ from ascites fluid to C2-Rep$_4$CT films did not give any detectable IgG band in the eluted fractions on SDS-PAGE (lanes 3-4), but the C2-Rep$_4$CT fiber seems to have bound mouse IgG$_1$ (lane 8, mouse IgG is ~160 kDa). However, both films (lanes 5 and 7) and the fiber (lane 9) of C2-Rep$_4$CT show binding of IgG from rabbit serum. As the source of mouse IgG$_1$ is here in the form of an ascites fluid, it may be the case that something in this fluid is somehow disturbing the binding between C2 and IgG$_1$ in the film. Control films and fibers of Rep$_4$CT did not show any IgG in the eluted fractions (lanes 10-14).

Example 27

Binding of IgG from Human Blood Plasma to C2-Rep$_4$CT Films

To further investigate the ability of C2-Rep$_4$CT to bind IgG, two films of each of C2-Rep$_4$CT (SEQ ID NO: 18), Z-Rep$_4$CT (SEQ ID NO: 14) and Rep$_4$CT (SEQ ID NO: 20) were incubated with 500 μl of human blood plasma (1:5 dilution) for 1 h at room temperature. After washing three times with 600 μl PBS, bound IgG was eluted in 500 μl by lowering the pH to approximately 2.7 with elution buffer (0.5 M acetic acid, 1 M urea, 100 mM NaCl), after which the eluted fractions were analyzed by non-reducing SDS-PAGE (FIG. 34).

Figure 34:
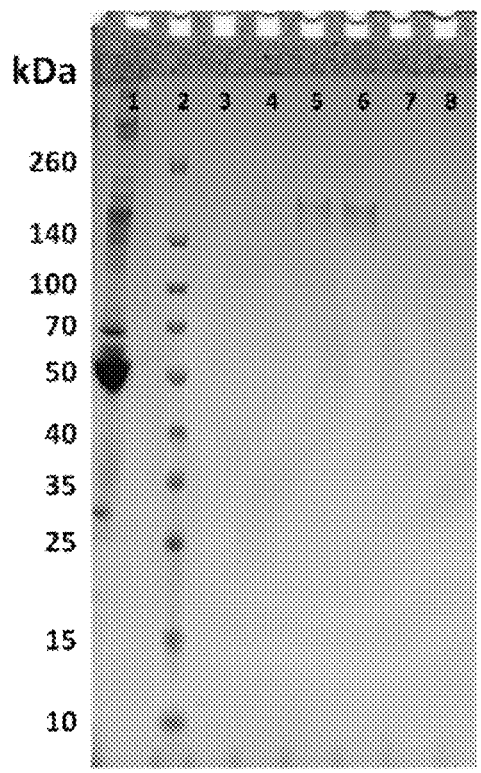

The gel in FIG. 34 was loaded according to:
(1) Human blood plasma (1:5), 1.4 μl loaded
(2) Molecular weight marker
(3-4) Duplicates of C2-Rep$_4$CT, film, 14 μl loaded
(5-6) Duplicates of Z-Rep$_4$CT, film, 14 μl loaded
(7-8) Duplicates of Rep$_4$CT, film, 14 μl loaded.

In FIG. 34, it can be seen that Z-Rep$_4$CT films have clearly bound IgG from human blood plasma (lanes 5-6). The C2-Rep$_4$CT films also show weaker IgG bands in the eluted fractions (lanes 3-4). The control films of Rep$_4$CT show no binding of IgG from human blood plasma (lanes 7-8).

Example 28

Comparison of Secondary Structure in Z-Rep$_4$CT and Rep$_4$CT Fibers and Films Using ATR-FTIR The secondary structure of the Z domain is α-helical in its active conformation, while the secondary structure of Rep$_4$CT fibers is predominantly of β-sheet type. If the Z domains in Z-Rep$_4$CT fibers and films are correctly folded, one would expect a higher α-helical content in those matrices compared to in Rep$_4$CT fibers and films. In order to investigate the difference in secondary structure, fibers and films of Z-Rep$_4$CT and Rep$_4$CT were analyzed by the spectroscopic method Attenuated Total Reflectance Fourier Transform InfraRed spectroscopy (ATR-FTIR), by which it is possible to distinguish α-helical (band position: 1648-1657 cm$^{-1}$) from β-sheet structure (band positions: 1623-1641, 1674-1695 cm$^{-1}$).

One film of Z-Rep$_4$CT (SEQ ID NO: 14) and one of Rep$_4$CT (SEQ ID NO: 20) were made by allowing 15 μl of protein solution to air-dry in room temperature over night. Fibers were made for Z-Rep$_4$CT and Rep$_4$CT and thereafter air-dried for ~30 min in room temperature under tension. ATR-FTIR was then recorded using a platinum ATR unit from Bruker. The IR spectra for both fiber and film (not shown) show that Z-Rep$_4$CT has a higher α-helical content than Rep$_4$CT, which indicates the presence of a correctly folded Z domain. This is in line with maintained functionality of the Z domain in Z-Rep$_4$CT structures according to the invention, see e.g. Examples 2-5, 17-19 and 22-23.

---

The invention claimed is:

1. A protein structure capable of selective interaction with an organic target, wherein said protein structure is a polymer comprising as a repeating structural unit a recombinant fusion protein that is capable of selective interaction with the organic target and comprising the moieties B, REP and CT, and optionally NT, wherein:

B is a non-spidroin moiety of more than 30 amino acid residues, which provides the capacity of selective interaction with the organic target, wherein the B moiety is selected from the group consisting of the Z domain of staphylococcal protein A, staphylococcal protein A and the E, D, A, B and C domains thereof; streptococcal protein G, the albumin-binding domain thereof and the C1, C2 and C3 domains thereof; streptavidin and monomeric streptavidin (M4); GA modules from *Finegoldia magna*; and variants thereof wherein the B moiety is capable of selective interaction with the organic target;

REP is a moiety of from 70 to 300 amino acid residues and is derived from the repetitive fragment of a spider silk protein, wherein the REP moiety is selected from the group of $L(AG)_nL$, $L(AG)_nAL$, $L(GA)_nL$, $L(GA)_nGL$, wherein n is an integer from 2 to 10;

each individual A segment is an amino acid sequence of from 8 to 18 amino acid residues, wherein from 0 to 3 of the amino acid residues are not Ala, and the remaining amino acid residues are Ala;

each individual G segment is an amino acid sequence of from 12 to 30 amino acid residues, wherein at least 40% of the amino acid residues are Gly; and each individual L segment is a linker amino acid sequence of from 0 to 20 amino acid residues;

CT is a moiety of from 70 to 120 amino acid residues and is derived from the C-terminal fragment of a spider silk protein, wherein the CT moiety has at least 50% identity to SEQ ID NO: 9 or at least 80% identity to SEQ ID NO: 7; and NT, when optionally present, is a moiety of from 100 to 160 amino acid residues and is derived from the N-terminal fragment of a spider silk protein; wherein the NT moiety has at least 50% identity to SEQ ID NO: 8 or at least 80% identity to SEQ ID NO: 6.

2. The protein structure according to claim 1, wherein the B moiety is selected from the group consisting of the Z domain derived from staphylococcal protein A, and variants thereof wherein the B moiety is capable of selective interaction with the organic target.

3. The protein structure according to claim 1, wherein the B moiety is selected from the group consisting of staphylococcal protein A, the E, D, A, B and C domains thereof, and variants thereof wherein the B moiety is capable of selective interaction with the organic target.

4. The protein structure according to claim 1, wherein the B moiety is selected from the group consisting of streptococcal protein G, the albumin-binding domain thereof, the C1, C2 and C3 domains thereof and variants thereof wherein the B moiety is capable of selective interaction with the organic target.

5. The protein structure according to claim 1, wherein the B moiety is selected from the group consisting of streptavidin, monomeric streptavidin (M4) and variants thereof wherein the B moiety is capable of selective interaction with the organic target.

6. The protein structure according to claim 1, wherein the B moiety is selected from the group consisting of GA modules from *Finegoldia magna* and protein fragments having at least 70% identity to GA modules from *Finegoldia magna*.

7. The protein structure according to claim 1, wherein said recombinant fusion protein is selected from the group of proteins defined by the formulas:

$$B_x\text{-REP-}B_y\text{-CT-}B_z \text{ and } B_x\text{-CT-}B_y\text{-REP-}B_z,$$

wherein x, y and z are integers from 0 to 5;
and x+y+z≥1.

8. The protein structure according to claim 7, wherein said recombinant fusion protein is selected from the group of proteins defined by the formulas $B_y$-REP-CT, $B_y$-CT-REP, REP-CT-$B_E$ and CT-REP-$B_E$;

wherein x and z are integers from 1 to 5.

9. The protein structure according to claim 8, wherein said recombinant fusion protein is selected from the group of proteins defined by the formulas B-REP-CT, B-CT-REP, REP-CT-B and CT-REP-B.

10. The protein structure according to claim 1, wherein said protein structure has a size of at least 0.1 μm in at least two dimensions.

11. The protein structure according to claim 1, wherein said protein structure is in a physical form selected from the group consisting of fiber, film, foam, net, mesh, sphere and capsule.

12. The protein structure according to claim 1, wherein the CT moiety has at least 90% identity to SEQ ID NO:7.

13. The protein structure according to claim 12, wherein the CT moiety is SEQ ID NO:7.

14. A method for providing a protein structure capable of selective interaction with an organic target, wherein said protein structure is a polymer comprising as a repeating structural unit a recombinant fusion protein that is capable of selective interaction with the organic target and comprising moieties B, REP CT, and optionally NT, wherein the polymer comprises more than 100 fusion protein structural units, and wherein:

B is a non-spidroin moiety of more than 30 amino acid residues, which provides the capacity of selective interaction with the organic target, wherein the B moiety is selected from the group consisting of the Z domain of staphylococcal protein A, staphylococcal protein A and the E, D, A, B and C domains thereof; streptococcal protein G, the albumin-binding domain thereof and the C1, C2 and C3 domains thereof; streptavidin and monomeric streptavidin (M4); GA modules from *Finegoldia magna*; and variants thereof wherein the B moiety is capable of selective interaction with the organic target;

REP is a moiety of from 70 to 300 amino acid residues and is derived from the repetitive fragment of a spider silk protein,
wherein the REP moiety is selected from the group of L(AG)$_n$L, L(AG)$_n$AL, L(GA)$_n$L, L(GA)$_n$GL, wherein n is an integer from 2 to 10;
each individual A segment is an amino acid sequence of from 8 to 18 amino acid residues, wherein from 0 to 3 of the amino acid residues are not Ala, and the remaining amino acid residues are Ala;
each individual G segment is an amino acid sequence of from 12 to 30 amino acid residues, wherein at least 40% of the amino acid residues are Gly; and
each individual L segment is a linker amino acid sequence of from 0 to 20 amino acid residues;
CT is a moiety of from 70 to 120 amino acid residues and is derived from the C-terminal fragment of a spider silk protein, wherein the CT moiety has at least 50% identity to SEQ ID NO: 9 or at least 80% identity to SEQ ID NO: 7; and
NT, when optionally present, is a moiety of from 100 to 160 amino acid residues and is derived from the N-terminal fragment of a spider silk protein; wherein the NT moiety has at least 50% identity to SEQ ID NO: 8 or at least 80% identity to SEQ ID NO: 6,
said method comprising the steps of:
(a) providing said recombinant fusion protein; and
(b) subjecting the fusion protein to conditions to achieve formation of a polymer comprising the recombinant fusion protein.

15. An affinity medium for immobilization of an organic target, said affinity medium comprising a fusion protein that is capable of selective interaction with the organic target and comprising the moieties B, REP, CT, and optionally NT, wherein:
B is a non-spidroin moiety of more than 30 amino acid residues, which provides the capacity of selective interaction with the organic target,
wherein the B moiety is selected from the group consisting of the Z domain of staphylococcal protein A, staphylococcal protein A and the E, D, A, B and C domains thereof; streptococcal protein G, the albumin-binding domain thereof and the C1, C2 and C3 domains thereof; streptavidin and monomeric streptavidin (M4); GA modules from *Finegoldia magna*; and variants thereof wherein the B moiety is capable of selective interaction with the organic target;
REP is a moiety of from 70 to 300 amino acid residues and is derived from the repetitive fragment of a spider silk protein,
wherein the REP moiety is selected from the group of L(AG)$_n$L, L(AG)$_n$AL, L(GA)$_n$L, L(GA)$_n$GL, wherein n is an integer from 2 to 10;
each individual A segment is an amino acid sequence of from 8 to 18 amino acid residues, wherein from 0 to 3 of the amino acid residues are not Ala, and the remaining amino acid residues are Ala;
each individual G segment is an amino acid sequence of from 12 to 30 amino acid residues, wherein at least 40% of the amino acid residues are Gly; and
each individual L segment is a linker amino acid sequence of from 0 to 20 amino acid residues;
CT is a moiety of from 70 to 120 amino acid residues and is derived from the C-terminal fragment of a spider silk protein, wherein the CT moiety has at least 50% identity to SEQ ID NO: 9 or at least 80% identity to SEQ ID NO: 7; and
NT, when optionally present, is a moiety of from 100 to 160 amino acid residues and is derived from the N-terminal fragment of a spider silk protein; wherein the NT moiety has at least 50% identity to SEQ ID NO: 8 or at least 80% identity to SEQ ID NO: 6.

16. A cell scaffold material for cultivation of cells having an organic target that is present on the cell surface, said cell scaffold material comprising the protein structure according to claim 1, wherein said cell scaffold material is further comprising an intermediate organic target, wherein the B moiety is capable of selective interaction with and is bound to said intermediate organic target, and wherein said intermediate organic target is capable of selective interaction with the organic target that is present on the cell surface.

17. A method for separation of an organic target from a sample, comprising the steps of:
providing a sample containing the organic target;
providing the affinity medium according to claim 15, wherein said affinity medium is capable of selective interaction with the organic target;
contacting said affinity medium with said sample under suitable conditions to achieve binding between the affinity medium and the organic target; and
removing non-bound sample.

18. A method for immobilization of cells, comprising
providing a sample comprising cells of interest;
applying said sample to the cell scaffold material according to claim 16, wherein said cell scaffold material is capable of selective interaction with an organic target that is present on the cell surface; and
allowing said cells to immobilize to said cell scaffold material by binding between the organic target on the cell surface and said cell scaffold material.

19. A method for cultivation of cells, comprising
immobilizing cells of interest to a cell scaffold material according to the method of claim 18; and
maintaining said cell scaffold material having cells applied thereto under conditions suitable for cell culture.

* * * * *

```
                         SEQUENCE LISTING

<160> NUMBER OF SEQ ID NOS: 27

<210> SEQ ID NO 1
<211> LENGTH: 149
<212> TYPE: PRT
<213> ORGANISM: Euprosthenops australis

<400> SEQUENCE: 1

Gly Ser Gly Asn Ser Gly Ile Gln Gly Gln Gly Gly Tyr Gly Gly Leu
1               5                   10                  15

Gly Gln Gly Gly Tyr Gly Gln Gly Ala Gly Ser Ser Ala Ala Ala Ala
            20                  25                  30

Ala Ala Ala Ala Ala Ala Ala Ala Gly Gly Gln Gly Gly Gln Gly Gln
        35                  40                  45

Gly Gly Tyr Gly Gln Gly Ser Gly Ser Ala Ala Ala Ala Ala
    50                  55                  60

Ala Ala Ala Ala Ala Ala Ala Ala Ala Gly Arg Gly Gln Gly Gly Tyr
65                  70                  75                  80

Gly Gln Gly Ser Gly Gly Asn Ala Ala Ala Ala Ala Ala Ala Ala
                85                  90                  95

Ala Ala Ala Ala Gly Gln Gly Gly Gln Gly Gly Tyr Gly Arg Gln
            100                 105                 110

Ser Gln Gly Ala Gly Ser Ala Ala Ala Ala Ala Ala Ala Ala Ala
        115                 120                 125

Ala Ala Ala Ala Gly Ser Gly Gln Gly Gly Tyr Gly Gln Gly Gln Gly
    130                 135                 140

Gly Tyr Gly Gln Ser
145

<210> SEQ ID NO 2
<211> LENGTH: 265
<212> TYPE: PRT
<213> ORGANISM: Euprosthenops australis
<220> FEATURE:
<221> NAME/KEY: DOMAIN
<222> LOCATION: (1)..(167)
<223> OTHER INFORMATION: REP fragment
<220> FEATURE:
<221> NAME/KEY: DOMAIN
<222> LOCATION: (168)..(265)
<223> OTHER INFORMATION: CT fragment

<400> SEQUENCE: 2

Gly Ser Gly Asn Ser Gly Ile Gln Gly Gln Gly Gly Tyr Gly Gly Leu
1               5                   10                  15

Gly Gln Gly Gly Tyr Gly Gln Gly Ala Gly Ser Ser Ala Ala Ala Ala
            20                  25                  30

Ala Ala Ala Ala Ala Ala Ala Ala Gly Gly Gln Gly Gly Gln Gly Gln
        35                  40                  45

Gly Gly Tyr Gly Gln Gly Ser Gly Ser Ala Ala Ala Ala Ala
    50                  55                  60

Ala Ala Ala Ala Ala Ala Ala Ala Ala Gly Arg Gly Gln Gly Gly Tyr
65                  70                  75                  80

Gly Gln Gly Ser Gly Gly Asn Ala Ala Ala Ala Ala Ala Ala Ala
```

```
                        85                  90                  95
Ala Ala Ala Ala Ala Gly Gln Gly Gly Gln Gly Gly Tyr Gly Arg Gln
                100                 105                 110

Ser Gln Gly Ala Gly Ser Ala Ala Ala Ala Ala Ala Ala Ala Ala Ala
            115                 120                 125

Ala Ala Ala Gly Ser Gly Gln Gly Gly Tyr Gly Gln Gly Gln Gly
        130                 135                 140

Gly Tyr Gly Gln Ser Ser Ala Ser Ala Ala Ala Ser Ala Ala
145                 150                 155                 160

Ser Thr Val Ala Asn Ser Val Ser Arg Leu Ser Ser Pro Ser Ala Val
                165                 170                 175

Ser Arg Val Ser Ser Ala Val Ser Ser Leu Val Ser Asn Gly Gln Val
            180                 185                 190

Asn Met Ala Ala Leu Pro Asn Ile Ile Ser Asn Ile Ser Ser Ser Val
                195                 200                 205

Ser Ala Ser Ala Pro Gly Ala Ser Gly Cys Glu Val Ile Val Gln Ala
            210                 215                 220

Leu Leu Glu Val Ile Thr Ala Leu Val Gln Ile Val Ser Ser Ser Ser
225                 230                 235                 240

Val Gly Tyr Ile Asn Pro Ser Ala Val Asn Gln Ile Thr Asn Val Val
                245                 250                 255

Ala Asn Ala Met Ala Gln Val Met Gly
            260                 265

<210> SEQ ID NO 3
<211> LENGTH: 296
<212> TYPE: PRT
<213> ORGANISM: Euprosthenops australis
<220> FEATURE:
<221> NAME/KEY: DOMAIN
<222> LOCATION: (1)..(137)
<223> OTHER INFORMATION: NT fragment
<220> FEATURE:
<221> NAME/KEY: DOMAIN
<222> LOCATION: (138)..(296)
<223> OTHER INFORMATION: REP fragment

<400> SEQUENCE: 3

Gly Ser Gly Asn Ser His Thr Thr Pro Trp Thr Asn Pro Gly Leu Ala
1               5                   10                  15

Glu Asn Phe Met Asn Ser Phe Met Gln Gly Leu Ser Ser Met Pro Gly
                20                  25                  30

Phe Thr Ala Ser Gln Leu Asp Asp Met Ser Thr Ile Ala Gln Ser Met
            35                  40                  45

Val Gln Ser Ile Gln Ser Leu Ala Ala Gln Gly Arg Thr Ser Pro Asn
        50                  55                  60

Lys Leu Gln Ala Leu Asn Met Ala Phe Ala Ser Ser Met Ala Glu Ile
65                  70                  75                  80

Ala Ala Ser Glu Glu Gly Gly Gly Ser Leu Ser Thr Lys Thr Ser Ser
                85                  90                  95

Ile Ala Ser Ala Met Ser Asn Ala Phe Leu Gln Thr Thr Gly Val Val
            100                 105                 110

Asn Gln Pro Phe Ile Asn Glu Ile Thr Gln Leu Val Ser Met Phe Ala
        115                 120                 125

Gln Ala Gly Met Asn Asp Val Ser Ala Ser Ala Ser Ala Gly Ala Ser
    130                 135                 140

Ala Ala Ala Ser Ala Gly Ala Ala Ser Gly Gln Gly Gly Tyr Gly Gly
```

```
145                 150                 155                 160
Leu Gly Gln Gly Gly Tyr Gly Gln Gly Ala Gly Ser Ser Ala Ala Ala
                165                 170                 175
Ala Ala Ala Ala Ala Ala Ala Ala Gly Gly Gln Gly Gly Gln Gly
            180                 185                 190
Gln Gly Gly Tyr Gly Gln Ser Gly Gly Ser Ala Ala Ala Ala Ala
            195                 200                 205
Ala Ala Ala Ala Ala Ala Ala Ala Gly Arg Gly Gln Gly Gly
        210                 215                 220
Tyr Gly Gln Gly Ser Gly Gly Asn Ala Ala Ala Ala Ala Ala Ala
225                 230                 235                 240
Ala Ala Ala Ala Ala Ala Gly Gln Gly Gln Gly Gly Tyr Gly
            245                 250                 255
Arg Gln Ser Gln Gly Ala Gly Ser Ala Ala Ala Ala Ala Ala Ala
            260                 265                 270
Ala Ala Ala Ala Ala Gly Ser Gly Gln Gly Gly Tyr Gly Gly Gln
        275                 280                 285
Gly Gln Gly Gly Tyr Gly Gln Ser
        290                 295

<210> SEQ ID NO 4
<211> LENGTH: 340
<212> TYPE: PRT
<213> ORGANISM: Euprosthenops australis
<220> FEATURE:
<221> NAME/KEY: DOMAIN
<222> LOCATION: (1)..(137)
<223> OTHER INFORMATION: NT fragment
<220> FEATURE:
<221> NAME/KEY: DOMAIN
<222> LOCATION: (138)..(340)
<223> OTHER INFORMATION: REP fragment

<400> SEQUENCE: 4

Gly Ser Gly Asn Ser His Thr Thr Pro Trp Thr Asn Pro Gly Leu Ala
1               5                   10                  15
Glu Asn Phe Met Asn Ser Phe Met Gln Gly Leu Ser Ser Met Pro Gly
            20                  25                  30
Phe Thr Ala Ser Gln Leu Asp Asp Met Ser Thr Ile Ala Gln Ser Met
        35                  40                  45
Val Gln Ser Ile Gln Ser Leu Ala Ala Gln Gly Arg Thr Ser Pro Asn
    50                  55                  60
Lys Leu Gln Ala Leu Asn Met Ala Phe Ala Ser Ser Met Ala Glu Ile
65                  70                  75                  80
Ala Ala Ser Glu Glu Gly Gly Gly Ser Leu Ser Thr Lys Thr Ser Ser
                85                  90                  95
Ile Ala Ser Ala Met Ser Asn Ala Phe Leu Gln Thr Thr Gly Val Val
            100                 105                 110
Asn Gln Pro Phe Ile Asn Glu Ile Thr Gln Leu Val Ser Met Phe Ala
        115                 120                 125
Gln Ala Gly Met Asn Asp Val Ser Ala Ser Ala Ser Ala Gly Ala Ser
    130                 135                 140
Ala Ala Ala Ser Ala Gly Ala Pro Gly Tyr Ser Pro Ala Pro Ser Tyr
145                 150                 155                 160
Ser Ser Gly Gly Tyr Ala Ser Ser Ala Ala Ser Ala Ala Ala Ala Ala
                165                 170                 175
Gly Gln Gly Gly Pro Gly Gly Tyr Gly Pro Ala Pro Asn Gln Gly Ala
```

```
                   180                 185                 190
Ser Ser Ala Ala Ala Ala Ala Gly Ser Gly Gln Gly Pro Ser Gly
        195                 200                 205

Pro Tyr Gly Thr Ser Tyr Gln Ile Ser Thr Gln Tyr Thr Gln Thr
    210                 215                 220

Thr Ser Gln Gly Gln Gly Tyr Gly Ser Ser Ala Gly Ala Ala Ala
225                 230                 235                 240

Ala Gly Ala Ala Gly Ala Gly Gln Gly Tyr Gly Gly Gln Gly Gln
                245                 250                 255

Gly Gly Tyr Gly Gln Gly Ala Gly Gly Ala Ala Ala Ala Ala Ala
            260                 265                 270

Ala Ala Ala Ala Ala Ala Ala Gly Gln Gly Gly Gln Gly Gly Gly
        275                 280                 285

Gly Tyr Gly Gln Gly Gly Gln Gly Gly Gln Gly Gly Gln Gly Gly
    290                 295                 300

Gly Tyr Gly Gln Gly Ala Gly Ser Ser Ala Ala Ala Ala Ala Ala
305                 310                 315                 320

Ala Ala Ala Ala Ala Ala Ala Gly Arg Gly Gln Gly Tyr Gly Pro
                325                 330                 335

Gly Ser Gly Gly
        340

<210> SEQ ID NO 5
<211> LENGTH: 424
<212> TYPE: PRT
<213> ORGANISM: Euprosthenops australis
<220> FEATURE:
<221> NAME/KEY: DOMAIN
<222> LOCATION: (1)..(136)
<223> OTHER INFORMATION: NT fragment
<220> FEATURE:
<221> NAME/KEY: DOMAIN
<222> LOCATION: (137)..(313)
<223> OTHER INFORMATION: REP fragment
<220> FEATURE:
<221> NAME/KEY: DOMAIN
<222> LOCATION: (314)..(411)
<223> OTHER INFORMATION: CT fragment
<220> FEATURE:
<221> NAME/KEY: DOMAIN
<222> LOCATION: (412)..(424)
<223> OTHER INFORMATION: His tag

<400> SEQUENCE: 5

Met Lys Ala Ser His Thr Thr Pro Trp Thr Asn Pro Gly Leu Ala Glu
1               5                   10                  15

Asn Phe Met Asn Ser Phe Met Gln Gly Leu Ser Ser Met Pro Gly Phe
                20                  25                  30

Thr Ala Ser Gln Leu Asp Asp Met Ser Thr Ile Ala Gln Ser Met Val
            35                  40                  45

Gln Ser Ile Gln Ser Leu Ala Ala Gln Gly Arg Thr Ser Pro Asn Lys
        50                  55                  60

Leu Gln Ala Leu Asn Met Ala Phe Ala Ser Ser Met Ala Glu Ile Ala
65                  70                  75                  80

Ala Ser Glu Glu Gly Gly Gly Ser Leu Ser Thr Lys Thr Ser Ser Ile
                85                  90                  95

Ala Ser Ala Met Ser Asn Ala Phe Leu Gln Thr Thr Gly Val Val Asn
            100                 105                 110

Gln Pro Phe Ile Asn Glu Ile Thr Gln Leu Val Ser Met Phe Ala Gln
        115                 120                 125
```

-continued

```
Ala Gly Met Asn Asp Val Ser Ala Ser Ala Gly Ala Ser Ala
            130                 135                 140
Ala Ala Ser Ala Gly Ala Ser Gly Gln Gly Tyr Gly Gly Leu
145                 150                 155                 160
Gly Gln Gly Gly Tyr Gly Gln Gly Ala Gly Ser Ser Ala Ala Ala
                165                 170                 175
Ala Ala Ala Ala Ala Ala Ala Gly Gly Gln Gly Gly Gln Gly Gln
                180                 185                 190
Gly Gly Tyr Gly Gln Gly Ser Gly Gly Ser Ala Ala Ala Ala Ala
                195                 200                 205
Ala Ala Ala Ala Ala Ala Ala Ala Gly Arg Gly Gln Gly Gly Tyr
            210                 215                 220
Gly Gln Gly Ser Gly Gly Asn Ala Ala Ala Ala Ala Ala Ala Ala
225                 230                 235                 240
Ala Ala Ala Ala Ala Gly Gln Gly Gln Gly Gly Tyr Gly Arg
                245                 250                 255
Gln Ser Gln Gly Ala Gly Ser Ala Ala Ala Ala Ala Ala Ala
                260                 265                 270
Ala Ala Ala Ala Ala Gly Ser Gly Gln Gly Gly Tyr Gly Gly Gln Gly
            275                 280                 285
Gln Gly Gly Tyr Gly Gln Ser Ser Ala Ser Ala Ser Ala Ala Ala Ser
                290                 295                 300
Ala Ala Ser Thr Val Ala Asn Ser Val Ser Arg Leu Ser Ser Pro Ser
305                 310                 315                 320
Ala Val Ser Arg Val Ser Ser Ala Val Ser Ser Leu Val Ser Asn Gly
                325                 330                 335
Gln Val Asn Met Ala Ala Leu Pro Asn Ile Ile Ser Asn Ile Ser Ser
                340                 345                 350
Ser Val Ser Ala Ser Ala Pro Gly Ala Ser Gly Cys Glu Val Ile Val
                355                 360                 365
Gln Ala Leu Leu Glu Val Ile Thr Ala Leu Val Gln Ile Val Ser Ser
            370                 375                 380
Ser Ser Val Gly Tyr Ile Asn Pro Ser Ala Val Asn Gln Ile Thr Asn
385                 390                 395                 400
Val Val Ala Asn Ala Met Ala Gln Val Met Gly Lys Leu Ala Ala
                405                 410                 415
Leu Glu His His His His His His
            420
```

<210> SEQ ID NO 6
<211> LENGTH: 137
<212> TYPE: PRT
<213> ORGANISM: Euprosthenops australis
<220> FEATURE:
<221> NAME/KEY: VARIANT
<222> LOCATION: (6)..(6)
<223> OTHER INFORMATION: deletion (deltaHis)

<400> SEQUENCE: 6

```
Gly Ser Gly Asn Ser His Thr Thr Pro Trp Thr Asn Pro Gly Leu Ala
1               5                   10                  15
Glu Asn Phe Met Asn Ser Phe Met Gln Gly Leu Ser Ser Met Pro Gly
                20                  25                  30
Phe Thr Ala Ser Gln Leu Asp Asp Met Ser Thr Ile Ala Gln Ser Met
            35                  40                  45
```

```
Val Gln Ser Ile Gln Ser Leu Ala Ala Gln Gly Arg Thr Ser Pro Asn
 50                  55                  60
Lys Leu Gln Ala Leu Asn Met Ala Phe Ala Ser Ser Met Ala Glu Ile
 65                  70                  75                  80
Ala Ala Ser Glu Glu Gly Gly Ser Leu Ser Thr Lys Thr Ser Ser
                 85                  90                  95
Ile Ala Ser Ala Met Ser Asn Ala Phe Leu Gln Thr Thr Gly Val Val
                100                 105                 110
Asn Gln Pro Phe Ile Asn Glu Ile Thr Gln Leu Val Ser Met Phe Ala
                115                 120                 125
Gln Ala Gly Met Asn Asp Val Ser Ala
                130                 135
```

```
<210> SEQ ID NO 7
<211> LENGTH: 98
<212> TYPE: PRT
<213> ORGANISM: Euprosthenops australis

<400> SEQUENCE: 7

Ser Arg Leu Ser Ser Pro Ser Ala Val Ser Arg Val Ser Ser Ala Val
 1               5                  10                  15
Ser Ser Leu Val Ser Asn Gly Gln Val Asn Met Ala Ala Leu Pro Asn
                 20                  25                  30
Ile Ile Ser Asn Ile Ser Ser Ser Val Ser Ala Ser Ala Pro Gly Ala
                 35                  40                  45
Ser Gly Cys Glu Val Ile Val Gln Ala Leu Leu Glu Val Ile Thr Ala
 50                  55                  60
Leu Val Gln Ile Val Ser Ser Ser Ser Val Gly Tyr Ile Asn Pro Ser
 65                  70                  75                  80
Ala Val Asn Gln Ile Thr Asn Val Val Ala Asn Ala Met Ala Gln Val
                 85                  90                  95
Met Gly
```

```
<210> SEQ ID NO 8
<211> LENGTH: 131
<212> TYPE: PRT
<213> ORGANISM: Artificial Sequence
<220> FEATURE:
<223> OTHER INFORMATION: Consensus sequence derived from spidroin NT
      fragments
<220> FEATURE:
<221> NAME/KEY: VARIANT
<222> LOCATION: (20)..(20)
<223> OTHER INFORMATION: Leu
<220> FEATURE:
<221> NAME/KEY: VARIANT
<222> LOCATION: (42)..(42)
<223> OTHER INFORMATION: Asn
<220> FEATURE:
<221> NAME/KEY: VARIANT
<222> LOCATION: (42)..(42)
<223> OTHER INFORMATION: Gln
<220> FEATURE:
<221> NAME/KEY: VARIANT
<222> LOCATION: (50)..(50)
<223> OTHER INFORMATION: Ser
<220> FEATURE:
<221> NAME/KEY: VARIANT
<222> LOCATION: (50)..(50)
<223> OTHER INFORMATION: Lys
<220> FEATURE:
<221> NAME/KEY: VARIANT
<222> LOCATION: (56)..(56)
<223> OTHER INFORMATION: Arg
<220> FEATURE:
```

-continued

```
<221> NAME/KEY: VARIANT
<222> LOCATION: (84)..(84)
<223> OTHER INFORMATION: Leu
<220> FEATURE:
<221> NAME/KEY: VARIANT
<222> LOCATION: (114)..(114)
<223> OTHER INFORMATION: Ser
<220> FEATURE:
<221> NAME/KEY: VARIANT
<222> LOCATION: (121)..(121)
<223> OTHER INFORMATION: Asn
<220> FEATURE:
<221> NAME/KEY: VARIANT
<222> LOCATION: (123)..(123)
<223> OTHER INFORMATION: Leu
<220> FEATURE:
<221> NAME/KEY: VARIANT
<222> LOCATION: (124)..(124)
<223> OTHER INFORMATION: Ser

<400> SEQUENCE: 8

Gln Ala Asn Thr Pro Trp Ser Ser Pro Asn Leu Ala Asp Ala Phe Ile
 1               5                  10                  15

Asn Ser Phe Met Ser Ala Ala Ser Ser Gly Ala Phe Ser Ala Asp
             20                  25                  30

Gln Leu Asp Asp Met Ser Thr Ile Gly Asp Thr Leu Met Ser Ala Met
         35                  40                  45

Asp Asn Met Gly Arg Ser Gly Lys Ser Thr Lys Ser Lys Leu Gln Ala
 50                  55                  60

Leu Asn Met Ala Phe Ala Ser Ser Met Ala Glu Ile Ala Ala Ala Glu
 65                  70                  75                  80

Ser Gly Gly Gly Ser Val Gly Val Lys Thr Asn Ala Ile Ser Asp Ala
                 85                  90                  95

Leu Ser Ser Ala Phe Tyr Gln Thr Thr Gly Ser Val Asn Pro Gln Phe
            100                 105                 110

Val Asn Glu Ile Arg Ser Leu Ile Gly Met Phe Ala Gln Ala Ser Ala
        115                 120                 125

Asn Glu Val
    130

<210> SEQ ID NO 9
<211> LENGTH: 100
<212> TYPE: PRT
<213> ORGANISM: Artificial Sequence
<220> FEATURE:
<223> OTHER INFORMATION: Consensus sequence derived from known MaSp1 and
      MaSp2 proteins
<220> FEATURE:
<221> NAME/KEY: MISC_FEATURE
<222> LOCATION: (1)..(71)
<223> OTHER INFORMATION: Sequence length present in known species
      variants
<220> FEATURE:
<221> NAME/KEY: VARIANT
<222> LOCATION: (7)..(7)
<223> OTHER INFORMATION: Glu

<400> SEQUENCE: 9

Ser Arg Leu Ser Ser Pro Gln Ala Ser Ser Arg Val Ser Ser Ala Val
 1               5                  10                  15

Ser Asn Leu Val Ser Ser Gly Pro Thr Asn Ser Ala Ala Leu Ser Asn
             20                  25                  30

Thr Ile Ser Asn Val Val Ser Gln Ile Ser Ala Ser Asn Pro Gly Leu
         35                  40                  45

Ser Gly Cys Asp Val Leu Val Gln Ala Leu Leu Glu Val Val Ser Ala
```

```
                    50                  55                  60
Leu Val His Ile Leu Gly Ser Ser Ile Gly Gln Val Asn Tyr Gly
 65                  70                  75                  80

Ser Ala Gly Gln Ala Thr Gln Ile Val Gly Gln Ser Val Ala Gln Ala
                 85                  90                  95

Leu Gly Glu Phe
            100

<210> SEQ ID NO 10
<211> LENGTH: 1110
<212> TYPE: PRT
<213> ORGANISM: Euprosthenops australis
<220> FEATURE:
<221> NAME/KEY: REPEAT
<222> LOCATION: (7)..(19)
<220> FEATURE:
<221> NAME/KEY: REPEAT
<222> LOCATION: (20)..(42)
<220> FEATURE:
<221> NAME/KEY: REPEAT
<222> LOCATION: (43)..(56)
<220> FEATURE:
<221> NAME/KEY: REPEAT
<222> LOCATION: (57)..(70)
<220> FEATURE:
<221> NAME/KEY: REPEAT
<222> LOCATION: (71)..(83)
<220> FEATURE:
<221> NAME/KEY: REPEAT
<222> LOCATION: (84)..(106)
<220> FEATURE:
<221> NAME/KEY: REPEAT
<222> LOCATION: (107)..(120)
<220> FEATURE:
<221> NAME/KEY: REPEAT
<222> LOCATION: (121)..(134)
<220> FEATURE:
<221> NAME/KEY: REPEAT
<222> LOCATION: (135)..(147)
<220> FEATURE:
<221> NAME/KEY: REPEAT
<222> LOCATION: (148)..(170)
<220> FEATURE:
<221> NAME/KEY: REPEAT
<222> LOCATION: (171)..(183)
<220> FEATURE:
<221> NAME/KEY: REPEAT
<222> LOCATION: (184)..(197)
<220> FEATURE:
<221> NAME/KEY: REPEAT
<222> LOCATION: (198)..(211)
<220> FEATURE:
<221> NAME/KEY: REPEAT
<222> LOCATION: (212)..(234)
<220> FEATURE:
<221> NAME/KEY: REPEAT
<222> LOCATION: (235)..(248)
<220> FEATURE:
<221> NAME/KEY: REPEAT
<222> LOCATION: (249)..(265)
<220> FEATURE:
<221> NAME/KEY: REPEAT
<222> LOCATION: (266)..(279)
<220> FEATURE:
<221> NAME/KEY: REPEAT
<222> LOCATION: (280)..(293)
<220> FEATURE:
<221> NAME/KEY: REPEAT
<222> LOCATION: (294)..(306)
<220> FEATURE:
<221> NAME/KEY: REPEAT
<222> LOCATION: (307)..(329)
<220> FEATURE:
<221> NAME/KEY: REPEAT
<222> LOCATION: (330)..(342)
```

```
<220> FEATURE:
<221> NAME/KEY: REPEAT
<222> LOCATION: (343)..(356)
<220> FEATURE:
<221> NAME/KEY: REPEAT
<222> LOCATION: (357)..(370)
<220> FEATURE:
<221> NAME/KEY: REPEAT
<222> LOCATION: (371)..(393)
<220> FEATURE:
<221> NAME/KEY: REPEAT
<222> LOCATION: (394)..(406)
<220> FEATURE:
<221> NAME/KEY: REPEAT
<222> LOCATION: (407)..(420)
<220> FEATURE:
<221> NAME/KEY: REPEAT
<222> LOCATION: (421)..(434)
<220> FEATURE:
<221> NAME/KEY: REPEAT
<222> LOCATION: (435)..(457)
<220> FEATURE:
<221> NAME/KEY: REPEAT
<222> LOCATION: (458)..(470)
<220> FEATURE:
<221> NAME/KEY: REPEAT
<222> LOCATION: (471)..(488)
<220> FEATURE:
<221> NAME/KEY: REPEAT
<222> LOCATION: (489)..(502)
<220> FEATURE:
<221> NAME/KEY: REPEAT
<222> LOCATION: (503)..(516)
<220> FEATURE:
<221> NAME/KEY: REPEAT
<222> LOCATION: (517)..(529)
<220> FEATURE:
<221> NAME/KEY: REPEAT
<222> LOCATION: (530)..(552)
<220> FEATURE:
<221> NAME/KEY: REPEAT
<222> LOCATION: (553)..(566)
<220> FEATURE:
<221> NAME/KEY: REPEAT
<222> LOCATION: (567)..(580)
<220> FEATURE:
<221> NAME/KEY: REPEAT
<222> LOCATION: (581)..(594)
<220> FEATURE:
<221> NAME/KEY: REPEAT
<222> LOCATION: (595)..(617)
<220> FEATURE:
<221> NAME/KEY: REPEAT
<222> LOCATION: (618)..(630)
<220> FEATURE:
<221> NAME/KEY: REPEAT
<222> LOCATION: (631)..(647)
<220> FEATURE:
<221> NAME/KEY: REPEAT
<222> LOCATION: (648)..(661)
<220> FEATURE:
<221> NAME/KEY: REPEAT
<222> LOCATION: (662)..(675)
<220> FEATURE:
<221> NAME/KEY: REPEAT
<222> LOCATION: (676)..(688)
<220> FEATURE:
<221> NAME/KEY: REPEAT
<222> LOCATION: (689)..(711)
<220> FEATURE:
<221> NAME/KEY: REPEAT
<222> LOCATION: (712)..(725)
<220> FEATURE:
<221> NAME/KEY: REPEAT
<222> LOCATION: (726)..(739)
<220> FEATURE:
<221> NAME/KEY: REPEAT
<222> LOCATION: (740)..(752)
<220> FEATURE:
```

```
<221> NAME/KEY: REPEAT
<222> LOCATION: (753)..(775)
<220> FEATURE:
<221> NAME/KEY: REPEAT
<222> LOCATION: (776)..(789)
<220> FEATURE:
<221> NAME/KEY: REPEAT
<222> LOCATION: (790)..(803)
<220> FEATURE:
<221> NAME/KEY: REPEAT
<222> LOCATION: (804)..(816)
<220> FEATURE:
<221> NAME/KEY: REPEAT
<222> LOCATION: (817)..(839)
<220> FEATURE:
<221> NAME/KEY: REPEAT
<222> LOCATION: (840)..(853)
<220> FEATURE:
<221> NAME/KEY: REPEAT
<222> LOCATION: (854)..(867)
<220> FEATURE:
<221> NAME/KEY: REPEAT
<222> LOCATION: (868)..(880)
<220> FEATURE:
<221> NAME/KEY: REPEAT
<222> LOCATION: (881)..(903)
<220> FEATURE:
<221> NAME/KEY: REPEAT
<222> LOCATION: (904)..(917)
<220> FEATURE:
<221> NAME/KEY: REPEAT
<222> LOCATION: (918)..(931)
<220> FEATURE:
<221> NAME/KEY: REPEAT
<222> LOCATION: (932)..(945)
<220> FEATURE:
<221> NAME/KEY: REPEAT
<222> LOCATION: (946)..(968)
<220> FEATURE:
<221> NAME/KEY: REPEAT
<222> LOCATION: (969)..(981)
<220> FEATURE:
<221> NAME/KEY: REPEAT
<222> LOCATION: (982)..(998)
<220> FEATURE:
<221> NAME/KEY: REPEAT
<222> LOCATION: (999)..(1013)
<220> FEATURE:
<221> NAME/KEY: REPEAT
<222> LOCATION: (1014)..(1027)
<220> FEATURE:
<221> NAME/KEY: REPEAT
<222> LOCATION: (1028)..(1042)
<220> FEATURE:
<221> NAME/KEY: REPEAT
<222> LOCATION: (1043)..(1059)
<220> FEATURE:
<221> NAME/KEY: REPEAT
<222> LOCATION: (1060)..(1073)
<220> FEATURE:
<221> NAME/KEY: REPEAT
<222> LOCATION: (1074)..(1092)

<400> SEQUENCE: 10

Gln Gly Ala Gly Gly Asn Ala Ala Ala Ala Ala Ala Ala Ala Ala
 1               5                  10                  15

Ala Ala Ala Gly Gln Gly Gly Gln Gly Gly Tyr Gly Gly Leu Gly Gln
                20                  25                  30

Gly Gly Tyr Gly Gln Gly Ala Gly Ser Ser Ala Ala Ala Ala Ala
            35                  40                  45

Ala Ala Ala Ala Ala Ala Ala Ala Gly Arg Gly Gln Gly Gly Tyr Gly
        50                  55                  60

Gln Gly Ser Gly Gly Asn Ala Ala Ala Ala Ala Ala Ala Ala Ala
65                  70                  75                  80
```

-continued

Ala Ala Ser Gly Gln Gly Gln Gly Gln Gly Gln Gly Gln
            85              90              95

Gly Gly Tyr Gly Gln Gly Ala Gly Ser Ser Ala Ala Ala Ala Ala
            100             105             110

Ala Ala Ala Ala Ala Ala Ala Ala Gly Gln Gly Gln Gly Arg Tyr Gly
            115             120             125

Gln Gly Ala Gly Asn Ala Ala Ala Ala Ala Ala Ala Ala
130             135             140

Ala Ala Ala Gly Gln Gly Gly Gln Gly Gly Gln Gly Gly Leu Gly Gln
145             150             155             160

Gly Gly Tyr Gly Gln Gly Ala Gly Ser Ser Ala Ala Ala Ala Ala
            165             170             175

Ser Ala Ala Ala Ala Ala Gly Arg Gly Gln Gly Gly Tyr Gly Gln
            180             185             190

Gly Ala Gly Gly Asn Ala Ala Ala Ala Ala Ala Ala Ala Ala
            195             200             205

Ala Ala Ala Gly Gln Gly Gly Gln Gly Gly Tyr Gly Gly Leu Gly Gln
            210             215             220

Gly Gly Tyr Gly Gln Gly Ala Gly Ser Ser Ala Ala Ala Ala Ala
225             230             235             240

Ala Ala Ala Ala Ala Ala Ala Gly Gly Gln Gly Gly Gln Gly Gln Gly
            245             250             255

Arg Tyr Gly Gln Gly Ala Gly Ser Ser Ala Ala Ala Ala Ala Ala
            260             265             270

Ala Ala Ala Ala Ala Ala Ala Gly Gln Gly Gln Gly Gly Tyr Gly Gln
            275             280             285

Gly Ala Gly Gly Asn Ala Ala Ala Ala Ala Ala Ala Ala Ala
            290             295             300

Ala Ala Gly Gln Gly Gly Gln Gly Gly Gln Gly Gly Leu Gly Gln Gly
305             310             315             320

Gly Tyr Gly Gln Gly Ala Gly Ser Ser Ala Ala Ala Ala Ala Ala
            325             330             335

Ala Ala Ala Ala Ala Ala Gly Arg Gly Gln Gly Gly Tyr Gly Gln Gly
            340             345             350

Ala Gly Gly Asn Ala Ala Ala Ala Ala Ala Ala Glu Ala Ala
            355             360             365

Ala Ala Gly Gln Gly Gly Gln Gly Gly Tyr Gly Gly Leu Gly Gln Gly
            370             375             380

Gly Tyr Gly Gln Gly Ala Gly Ser Ser Ala Ala Ala Ala Ala Ala
385             390             395             400

Ala Ala Ala Ala Ala Ala Gly Arg Gly Gln Gly Gly Tyr Gly Gln Gly
            405             410             415

Ala Gly Gly Asn Ala Ala Ala Ala Ala Ala Ala Ala Ala Ala
            420             425             430

Ala Ala Gly Gln Gly Gly Gln Gly Gly Tyr Gly Gly Leu Gly Gln Gly
            435             440             445

Gly Tyr Gly Gln Gly Ala Gly Ser Ser Ala Ala Ala Ala Ala Ala
            450             455             460

Ala Ala Ala Ala Ala Ala Gly Gly Gln Gly Gly Gln Gly Gln Gly Arg
465             470             475             480

Tyr Gly Gln Gly Ala Gly Ser Ser Ala Ala Ala Ala Ala Ala Ala
            485             490             495

```
Ala Ala Ala Ala Ala Gly Arg Gly Gln Gly Gly Tyr Gly Gln Gly
            500                 505                 510

Ser Gly Gly Asn Ala Ala Ala Ala Ala Ala Ala Ala Ala Ala Ala
            515                 520                 525

Ser Gly Gln Gly Ser Gln Gly Gly Gln Gly Gln Gly Gln Gly Gly
            530                 535                 540

Tyr Gly Gln Gly Ala Gly Ser Ser Ala Ala Ala Ala Ala Ala Ala
545                 550                 555                 560

Ala Ala Ala Ala Ala Ser Gly Arg Gly Gln Gly Tyr Gly Gln Gly
            565                 570                 575

Ala Gly Gly Asn Ala Ala Ala Ala Ala Ala Ala Ala Ala Ala Ala
            580                 585                 590

Ala Ala Gly Gln Gly Gly Gln Gly Gly Tyr Gly Gly Leu Gly Gln Gly
            595                 600                 605

Gly Tyr Gly Gln Gly Ala Gly Ser Ser Ala Ala Ala Ala Ala Ala
            610                 615                 620

Ala Ala Ala Ala Ala Gly Gly Gln Gly Gly Gln Gly Gln Gly Gly Tyr
625                 630                 635                 640

Gly Gln Gly Ala Gly Ser Ser Ala Ala Ala Ala Ala Ala Ala Ala
            645                 650                 655

Ala Ala Ala Ala Ala Gly Arg Gly Gln Gly Gly Tyr Gly Gln Gly Ser
            660                 665                 670

Gly Gly Asn Ala Ala Ala Ala Ala Ala Ala Ala Ala Ala Ala Ser
            675                 680                 685

Gly Gln Gly Gly Gln Gly Gly Gln Gly Gly Gln Gly Gln Gly Gly Tyr
            690                 695                 700

Gly Gln Gly Ala Gly Ser Ser Ala Ala Ala Ala Ala Ala Ala Ala
705                 710                 715                 720

Ala Ala Ala Ala Ala Gly Gln Gly Gly Tyr Gly Gln Gly Ala
            725                 730                 735

Gly Gly Asn Ala Ala Ala Ala Ala Ala Ala Ala Ala Ala Ala Ala
            740                 745                 750

Gly Gln Gly Gly Gln Gly Gly Gln Gly Gly Leu Gly Gln Gly Gly Tyr
            755                 760                 765

Gly Gln Gly Ala Gly Ser Ser Ala Ala Ala Ala Ala Ala Ala Ala
            770                 775                 780

Ala Ala Ala Ala Gly Arg Gly Gln Gly Gly Tyr Gly Gln Gly Val
785                 790                 795                 800

Gly Gly Asn Ala Ala Ala Ala Ala Ala Ala Ala Ala Ala Ala Ala
            805                 810                 815

Gly Gln Gly Gly Gln Gly Gly Gln Gly Gly Leu Gly Gln Gly Gly Tyr
            820                 825                 830

Gly Gln Gly Ala Gly Ser Ser Ala Ala Ala Ala Ala Ala Ala Ala
            835                 840                 845

Ala Ala Ala Ala Ala Gly Arg Gly Gln Gly Gly Tyr Gly Gln Gly Ser
            850                 855                 860

Gly Gly Asn Ala Ala Ala Ala Ala Ala Ala Ala Ala Ala Ala Ser
865                 870                 875                 880

Gly Gln Gly Ser Gln Gly Gly Gln Gly Gln Gly Gln Gly Gly Tyr
            885                 890                 895

Gly Gln Gly Ala Gly Ser Ser Ala Ala Ala Ala Ala Ala Ala Ala
            900                 905                 910

Ala Ala Ala Ala Ser Gly Arg Gly Gln Gly Gly Tyr Gly Gln Gly Ala
```

```
              915                 920                 925
Gly Gly Asn Ala Ala Ala Ala Ala Ala Ala Ala Ala
        930                 935                 940

Ala Gly Gln Gly Gly Gln Gly Gly Tyr Gly Gly Leu Gly Gln Gly Gly
945                 950                 955                 960

Tyr Gly Gln Gly Ala Gly Ser Ser Ala Ala Ala Ala Ala Ala Ala
                965                 970                 975

Ala Ala Ala Ala Gly Gly Gln Gly Gly Gln Gly Gln Gly Gly Tyr Gly
            980                 985                 990

Gln Gly Ser Gly Gly Ser Ala Ala  Ala Ala Ala Ala  Ala Ala Ala
                995                 1000                1005

Ala Ala  Ala Ala Ala Gly Arg  Gly Gln Gly Gly Tyr  Gly Gln Gly
    1010                1015                1020

Ser Gly  Gly Asn Ala Ala Ala  Ala Ala Ala Ala  Ala Ala Ala
    1025                1030                1035

Ala Ala  Ala Ala Gly Gln Gly  Gly Gln Gly Gly Tyr  Gly Arg Gln
    1040                1045                1050

Ser Gln  Gly Ala Gly Ser Ala  Ala Ala Ala Ala  Ala Ala Ala
    1055                1060                1065

Ala Ala  Ala Ala Ala Gly Ser  Gly Gln Gly Gly Tyr  Gly Gly Gln
    1070                1075                1080

Gly Gln  Gly Gly Tyr Gly Gln  Ser Ser Ala Ser Ala  Ser Ala Ala
    1085                1090                1095

Ala Ser  Ala Ala Ser Thr Val  Ala Asn Ser Val Ser
    1100                1105                1110

<210> SEQ ID NO 11
<211> LENGTH: 23
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (4)..(4)
<223> OTHER INFORMATION: Ser
<220> FEATURE:
<221> NAME/KEY: VARIANT
<222> LOCATION: (8)..(8)
<223> OTHER INFORMATION: Tyr
<220> FEATURE:
<221> NAME/KEY: VARIANT
<222> LOCATION: (11)..(11)
<223> OTHER INFORMATION: Gln

<400> SEQUENCE: 11

Gly Gln Gly Gly Gln Gly Gly Gln Gly Gly Leu Gly Gln Gly Gly Tyr
1               5                   10                  15

Gly Gln Gly Ala Gly Ser Ser
            20

<210> SEQ ID NO 12
<211> LENGTH: 17
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (9)..(9)
<223> OTHER INFORMATION: Arg
```

```
<220> FEATURE:
<221> NAME/KEY: VARIANT
<222> LOCATION: (14)..(14)
<223> OTHER INFORMATION: Ser
<220> FEATURE:
<221> NAME/KEY: VARIANT
<222> LOCATION: (16)..(16)
<223> OTHER INFORMATION: Gly

<400> SEQUENCE: 12

Gly Gln Gly Gly Gln Gly Gln Gly Gly Tyr Gly Gln Gly Ala Gly Ser
1               5                   10                  15

Ser

<210> SEQ ID NO 13
<211> LENGTH: 14
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (2)..(2)
<223> OTHER INFORMATION: Gln
<220> FEATURE:
<221> NAME/KEY: VARIANT
<222> LOCATION: (6)..(6)
<223> OTHER INFORMATION: Arg
<220> FEATURE:
<221> NAME/KEY: VARIANT
<222> LOCATION: (11)..(11)
<223> OTHER INFORMATION: Ser
<220> FEATURE:
<221> NAME/KEY: VARIANT
<222> LOCATION: (11)..(11)
<223> OTHER INFORMATION: Val

<400> SEQUENCE: 13

Gly Arg Gly Gln Gly Gly Tyr Gly Gln Gly Ala Gly Gly Asn
1               5                   10

<210> SEQ ID NO 14
<211> LENGTH: 339
<212> TYPE: PRT
<213> ORGANISM: Artificial Sequence
<220> FEATURE:
<223> OTHER INFORMATION: Fusion protein
<220> FEATURE:
<221> NAME/KEY: DOMAIN
<222> LOCATION: (13)..(70)
<223> OTHER INFORMATION: Z domain
<220> FEATURE:
<221> NAME/KEY: DOMAIN
<222> LOCATION: (81)..(339)
<223> OTHER INFORMATION: REP-CT

<400> SEQUENCE: 14

Met Gly Ser Ser Gly His His His His His His Met Val Asp Asn Lys
1               5                   10                  15

Phe Asn Lys Glu Gln Gln Asn Ala Phe Tyr Glu Ile Leu His Leu Pro
                20                  25                  30

Asn Leu Asn Glu Glu Gln Arg Asn Ala Phe Ile Gln Ser Leu Lys Asp
            35                  40                  45

Asp Pro Ser Gln Ser Ala Asn Leu Leu Ala Glu Ala Lys Lys Leu Asn
        50                  55                  60

Asp Ala Gln Ala Pro Lys Leu Glu Ala Leu Phe Gln Gly Pro Asn Ser
65                  70                  75                  80
```

Gly Gln Gly Gly Tyr Gly Gly Leu Gly Gln Gly Gly Tyr Gly Gln Gly
                    85                  90                  95

Ala Gly Ser Ser Ala Ala Ala Ala Ala Ala Ala Ala Ala Ala Ala Ala
            100                 105                 110

Gly Gly Gln Gly Gly Gln Gly Gln Gly Gly Tyr Gly Gln Ser Gly
        115                 120                 125

Gly Ser Ala Ala Ala Ala Ala Ala Ala Ala Ala Ala Ala Ala
        130                 135                 140

Ala Gly Arg Gly Gln Gly Gly Tyr Gly Gln Ser Gly Gly Asn Ala
145                 150                 155                 160

Ala Ala Ala Ala Ala Ala Ala Ala Ala Ala Ala Ala Gly Gln
            165                 170                 175

Gly Gly Gln Gly Gly Tyr Gly Arg Gln Ser Gln Gly Ala Gly Ser Ala
            180                 185                 190

Ala Ala Ala Ala Ala Ala Ala Ala Ala Ala Ala Gly Ser Gly
        195                 200                 205

Gln Gly Gly Tyr Gly Gly Gln Gly Gln Gly Gly Tyr Gly Gln Ser Ser
        210                 215                 220

Ala Ser Ala Ser Ala Ala Ala Ser Ala Ala Ser Thr Val Ala Asn Ser
225                 230                 235                 240

Val Ser Arg Leu Ser Ser Pro Ser Ala Val Ser Arg Val Ser Ser Ala
                245                 250                 255

Val Ser Ser Leu Val Ser Asn Gly Gln Val Asn Met Ala Ala Leu Pro
                260                 265                 270

Asn Ile Ile Ser Asn Ile Ser Ser Val Ser Ala Ser Ala Pro Gly
            275                 280                 285

Ala Ser Gly Cys Glu Val Ile Val Gln Ala Leu Leu Glu Val Ile Thr
290                 295                 300

Ala Leu Val Gln Ile Val Ser Ser Ser Val Gly Tyr Ile Asn Pro
305                 310                 315                 320

Ser Ala Val Asn Gln Ile Thr Asn Val Val Ala Asn Ala Met Ala Gln
                325                 330                 335

Val Met Gly

<210> SEQ ID NO 15
<211> LENGTH: 1017
<212> TYPE: DNA
<213> ORGANISM: Artificial Sequence
<220> FEATURE:
<223> OTHER INFORMATION: Fusion protein

<400> SEQUENCE: 15
atgggcagca gcggccatca tcatcatcat catatggtag acaacaaatt caacaaagaa        60
caacaaaacg cgttctatga gatcttacat ttacctaact taaacgaaga caacgaaac        120 gccttcatcc aaagtttaaa agatgaccca agccaaagcg ctaacttgct agcagaagct       180
aaaaagctaa atgatgctca ggcgccgaaa ctggaagctc tgttccaggg tccgaattca       240
ggtcaaggtg gatatggtgg actaggtcaa ggaggatatg gacaaggtgc aggaagttct      300
gcagccgctg ccgccgccgc agcagccgcc gcagcaggtg acaaggtgg acaaggtcaa       360 ggaggatatg gacaaggttc aggaggttct gcagccgccg ccgccgccgc agcagcagca       420
gcagctgcag cagctggacg aggtcaagga ggatatggtc aaggttctgg aggtaatgct       480
gctgccgcag ccgctgccgc cgccgccgcc gctgcagcag ccggacaggg aggtcaaggt       540
ggatatggta gacaaagcca aggtgctggt tccgctgctg ctgctgctgc tgctgctgcc       600

```
gctgctgctg ctgcaggatc tggacaaggt ggatacggtg gacaaggtca aggaggttat    660
ggtcagagta gtgcttctgc ttcagctgct gcgtcagctg ctagtactgt agctaattcg    720
gtgagtcgcc tctcatcgcc ttccgcagta tctcgagttt cttcagcagt ttctagcttg    780
gtttcaaatg gtcaagtgaa tatggcagcg ttacctaata tcatttccaa catttcttct    840
tctgtcagtg catctgctcc tggtgcttct ggatgtgagg tcatagtgca agctctactc    900
gaagtcatca ctgctcttgt tcaaatcgtt agttcttcta gtgttggata tattaatcca    960
tctgctgtga accaaattac taatgttgtt gctaatgcca tggctcaagt aatgggc      1017

<210> SEQ ID NO 16
<211> LENGTH: 327
<212> TYPE: PRT
<213> ORGANISM: Artificial Sequence
<220> FEATURE:
<223> OTHER INFORMATION: Fusion protein
<220> FEATURE:
<221> NAME/KEY: DOMAIN
<222> LOCATION: (13)..(58)
<223> OTHER INFORMATION: Abd domain
<220> FEATURE:
<221> NAME/KEY: DOMAIN
<222> LOCATION: (69)..(327)
<223> OTHER INFORMATION: REP-CT

<400> SEQUENCE: 16

Met Gly Ser Ser Gly His His His His His His Met Leu Ala Glu Ala
1               5                   10                  15

Lys Val Leu Ala Asn Arg Glu Leu Asp Lys Tyr Gly Val Ser Asp Tyr
            20                  25                  30

Tyr Lys Asn Leu Ile Asn Asn Ala Lys Thr Val Glu Gly Val Lys Ala
        35                  40                  45

Leu Ile Asp Glu Ile Leu Ala Ala Leu Pro Leu Glu Ala Leu Phe Gln
    50                  55                  60

Gly Pro Asn Ser Gly Gln Gly Gly Tyr Gly Gly Leu Gly Gln Gly Gly
65                  70                  75                  80

Tyr Gly Gln Gly Ala Gly Ser Ser Ala Ala Ala Ala Ala Ala Ala Ala
                85                  90                  95

Ala Ala Ala Ala Gly Gly Gln Gly Gly Gln Gly Gln Gly Gly Tyr Gly
            100                 105                 110

Gln Gly Ser Gly Gly Ser Ala Ala Ala Ala Ala Ala Ala Ala Ala Ala
        115                 120                 125

Ala Ala Ala Ala Ala Gly Arg Gly Gln Gly Gly Tyr Gly Gln Gly Ser
    130                 135                 140

Gly Gly Asn Ala Ala Ala Ala Ala Ala Ala Ala Ala Ala Ala Ala Ala
145                 150                 155                 160

Ala Ala Gly Gln Gly Gly Gln Gly Gly Tyr Gly Arg Gln Ser Gln Gly
                165                 170                 175

Ala Gly Ser Ala Ala Ala Ala Ala Ala Ala Ala Ala Ala Ala Ala Ala
            180                 185                 190

Ala Gly Ser Gly Gln Gly Gly Tyr Gly Gly Gln Gly Gln Gly Gly Tyr
        195                 200                 205

Gly Gln Ser Ser Ala Ser Ala Ser Ala Ala Ala Ser Ala Ala Ser Thr
    210                 215                 220

Val Ala Asn Ser Val Ser Arg Leu Ser Ser Pro Ser Ala Val Ser Arg
225                 230                 235                 240

Val Ser Ser Ala Val Ser Ser Leu Val Ser Asn Gly Gln Val Asn Met
```

```
                    245                 250                 255
Ala Ala Leu Pro Asn Ile Ile Ser Asn Ile Ser Ser Val Ser Ala
            260                 265                 270

Ser Ala Pro Gly Ala Ser Gly Cys Glu Val Ile Val Gln Ala Leu Leu
        275                 280                 285

Glu Val Ile Thr Ala Leu Val Gln Ile Val Ser Ser Ser Val Gly
    290                 295                 300

Tyr Ile Asn Pro Ser Ala Val Asn Gln Ile Thr Asn Val Val Ala Asn
305                 310                 315                 320

Ala Met Ala Gln Val Met Gly
            325

<210> SEQ ID NO 17
<211> LENGTH: 981
<212> TYPE: DNA
<213> ORGANISM: Artificial Sequence
<220> FEATURE:
<223> OTHER INFORMATION: Fusion protein

<400> SEQUENCE: 17
atgggcagca gcggccatca tcatcatcat catatgttag ctgaagctaa agtcttagct      60
aacagagaac ttgacaaata tggagtaagt gactattaca agaacctaat caacaatgcc    120
aaaactgttg aaggtgtaaa agcactgata gatgaaattt tagctgcatt acctctggaa    180
gctctgttcc agggtccgaa ttcaggtcaa ggtggatatg gtggactagg tcaaggagga    240
tatggacaag gtgcaggaag ttctgcagcc gctgccgccg ccgcagcagc cgccgcagca    300
ggtggacaag gtggacaagg tcaaggagga tatggacaag gttcaggagg ttctgcagcc    360
gccgccgccg ccgcagcagc agcagcagct gcagcagctg gacgaggtca aggaggatat    420
ggtcaaggtt ctggaggtaa tgctgctgcc gcagccgctg ccgccgccgc cgccgctgca    480
gcagccggac aggaggtca aggtggatat ggtagacaaa gccaaggtgc tggttccgct    540
gctgctgctg ctgctgctgc tgccgctgct gctgctgcag atctggaca aggtggatac    600 ggtggacaag gtcaaggagg ttatggtcag agtagtgctt ctgcttcagc tgctgcgtca    660
gctgctagta ctgtagctaa ttcggtgagt cgcctctcat cgccttccgc agtatctcga    720
gtttcttcag cagtttctag cttggtttca aatggtcaag tgaatatggc agcgttacct    780
aatatcattt ccaacatttc ttcttctgtc agtgcatctg ctcctggtgc ttctggatgt    840
gaggtcatag tgcaagctct actcgaagtc atcactgctc ttgttcaaat cgttagttct    900
tctagtgttg gatatattaa tccatctgct gtgaaccaaa ttactaatgt tgttgctaat    960
gccatggctc aagtaatggg c                                               981

<210> SEQ ID NO 18
<211> LENGTH: 336
<212> TYPE: PRT
<213> ORGANISM: Artificial Sequence
<220> FEATURE:
<223> OTHER INFORMATION: Fusion protein
<220> FEATURE:
<221> NAME/KEY: DOMAIN
<222> LOCATION: (13)..(67)
<223> OTHER INFORMATION: C2 domain
<220> FEATURE:
<221> NAME/KEY: DOMAIN
<222> LOCATION: (77)..(336)
<223> OTHER INFORMATION: REP-CT

<400> SEQUENCE: 18
```

```
Met Gly Ser Ser Gly His His His His His Met Thr Tyr Lys Leu
1               5                   10                  15

Val Ile Asn Gly Lys Thr Leu Lys Gly Glu Thr Thr Thr Glu Ala Val
            20                  25                  30

Asp Ala Ala Thr Ala Glu Lys Val Phe Lys Gln Tyr Ala Asn Asp Asn
        35                  40                  45

Gly Val Asp Gly Glu Trp Thr Tyr Asp Asp Ala Thr Lys Thr Phe Thr
    50                  55                  60

Val Thr Glu Leu Glu Ala Leu Phe Gln Gly Pro Asn Ser Gly Gln Gly
65                  70                  75                  80

Gly Tyr Gly Gly Leu Gly Gln Gly Gly Tyr Gly Gln Gly Ala Gly Ser
                85                  90                  95

Ser Ala Ala Ala Ala Ala Ala Ala Ala Ala Ala Ala Gly Gly Gln
            100                 105                 110

Gly Gly Gln Gly Gln Gly Gly Tyr Gly Gln Gly Ser Gly Gly Ser Ala
            115                 120                 125

Ala Ala Ala Ala Ala Ala Ala Ala Ala Ala Ala Ala Ala Ala Gly Arg
        130                 135                 140

Gly Gln Gly Gly Tyr Gly Gln Gly Ser Gly Gly Asn Ala Ala Ala Ala
145                 150                 155                 160

Ala Ala Ala Ala Ala Ala Ala Ala Ala Ala Gly Gln Gly Gly Gln
            165                 170                 175

Gly Gly Tyr Gly Arg Gln Ser Gln Gly Ala Gly Ser Ala Ala Ala Ala
            180                 185                 190

Ala Ala Ala Ala Ala Ala Ala Ala Gly Ser Gly Gln Gly Gly
        195                 200                 205

Tyr Gly Gly Gln Gly Gln Gly Gly Tyr Gly Gln Ser Ser Ala Ser Ala
    210                 215                 220

Ser Ala Ala Ala Ser Ala Ala Ser Thr Val Ala Asn Ser Val Ser Arg
225                 230                 235                 240

Leu Ser Ser Pro Ser Ala Val Ser Arg Val Ser Ser Ala Val Ser Ser
                245                 250                 255

Leu Val Ser Asn Gly Gln Val Asn Met Ala Ala Leu Pro Asn Ile Ile
            260                 265                 270

Ser Asn Ile Ser Ser Ser Val Ser Ala Ser Pro Gly Ala Ser Gly
    275                 280                 285

Cys Glu Val Ile Val Gln Ala Leu Leu Glu Val Ile Thr Ala Leu Val
    290                 295                 300

Gln Ile Val Ser Ser Ser Val Gly Tyr Ile Asn Pro Ser Ala Val
305                 310                 315                 320

Asn Gln Ile Thr Asn Val Val Ala Asn Ala Met Ala Gln Val Met Gly
                325                 330                 335

<210> SEQ ID NO 19
<211> LENGTH: 1008
<212> TYPE: DNA
<213> ORGANISM: Artificial Sequence
<220> FEATURE:
<223> OTHER INFORMATION: Fusion protein

<400> SEQUENCE: 19
atgggcagca gcggccatca tcatcatcat catatgactt acaaacttgt tattaatggt      60
aaaacattga aggcgaaaca aactactgaa gctgttgatg ctgctactgc agaaaaagtc     120
ttcaaacaat acgctaacga caacggtgtt gacggtgaat ggacttacga cgatgcgact     180
```

```
aagaccttta cagttactga actggaagct ctgttccagg gtccgaattc aggtcaaggt    240
ggatatggtg gactaggtca aggaggatat ggacaaggtg caggaagttc tgcagccgct    300
gccgccgccg cagcagccgc cgcagcaggt ggacaaggtg gacaaggtca aggaggatat    360
ggacaaggtt caggaggttc tgcagccgcc gccgccgccg cagcagcagc agcagctgca    420
gcagctggac gaggtcaagg aggatatggt caaggttctg gaggtaatgc tgctgccgca    480
gccgctgccg ccgccgccgc cgctgcagca gccggacagg gaggtcaagg tggatatggt    540
agacaaagcc aaggtgctgg ttccgctgct gctgctgctg ctgctgctgc cgctgctgct    600
gctgcaggat ctggacaagg tggatacggt ggacaaggtc aaggaggtta tggtcagagt    660
agtgcttctg cttcagctgc tgcgtcagct gctagtactg tagctaattc ggtgagtcgc    720
ctctcatcgc cttccgcagt atctcgagtt tcttcagcag tttctagctt ggtttcaaat    780
ggtcaagtga atatggcagc gttacctaat atcatttcca acatttcttc ttctgtcagt    840
gcatctgctc ctggtgcttc tggatgtgag gtcatagtgc aagctctact cgaagtcatc    900
actgctcttg ttcaaatcgt tagttcttct agtgttggat atattaatcc atctgctgtg    960
aaccaaatta ctaatgttgt tgctaatgcc atggctcaag taatgggc                1008
```

<210> SEQ ID NO 20
<211> LENGTH: 263
<212> TYPE: PRT
<213> ORGANISM: Euprosthenops australis
<400> SEQUENCE: 20

```
Gly Pro Asn Ser Gly Gln Gly Gly Tyr Gly Gly Leu Gly Gln Gly Gly
1               5                   10                  15

Tyr Gly Gln Gly Ala Gly Ser Ser Ala Ala Ala Ala Ala Ala Ala Ala
            20                  25                  30

Ala Ala Ala Ala Gly Gly Gln Gly Gly Gln Gly Gln Gly Gly Tyr Gly
        35                  40                  45

Gln Gly Ser Gly Gly Ser Ala Ala Ala Ala Ala Ala Ala Ala Ala Ala
    50                  55                  60

Ala Ala Ala Ala Ala Gly Arg Gly Gln Gly Gly Tyr Gly Gln Gly Ser
65                  70                  75                  80

Gly Gly Asn Ala Ala Ala Ala Ala Ala Ala Ala Ala Ala Ala Ala Ala
                85                  90                  95

Ala Ala Gly Gln Gly Gly Gln Gly Gly Tyr Gly Arg Gln Ser Gln Gly
            100                 105                 110

Ala Gly Ser Ala Ala Ala Ala Ala Ala Ala Ala Ala Ala Ala Ala Ala
        115                 120                 125

Ala Gly Ser Gly Gln Gly Gly Tyr Gly Gly Gln Gly Gln Gly Gly Tyr
    130                 135                 140

Gly Gln Ser Ser Ala Ser Ala Ser Ala Ala Ala Ser Ala Ala Ser Thr
145                 150                 155                 160

Val Ala Asn Ser Val Ser Arg Leu Ser Ser Pro Ser Ala Val Ser Arg
                165                 170                 175

Val Ser Ser Ala Val Ser Ser Leu Val Ser Asn Gly Gln Val Asn Met
            180                 185                 190

Ala Ala Leu Pro Asn Ile Ile Ser Asn Ile Ser Ser Val Ser Ala
        195                 200                 205

Ser Ala Pro Gly Ala Ser Gly Cys Glu Val Ile Val Gln Ala Leu Leu
    210                 215                 220

Glu Val Ile Thr Ala Leu Val Gln Ile Val Ser Ser Ser Ser Val Gly
```

```
225                 230                 235                 240
Tyr Ile Asn Pro Ser Ala Val Asn Gln Ile Thr Asn Val Val Ala Asn
                245                 250                 255

Ala Met Ala Gln Val Met Gly
            260

<210> SEQ ID NO 21
<211> LENGTH: 789
<212> TYPE: DNA
<213> ORGANISM: Euprosthenops australis

<400> SEQUENCE: 21
ggtccgaatt caggtcaagg tggatatggt ggactaggtc aaggaggata tggacaaggt      60
gcaggaagtt ctgcagccgc tgccgccgcc gcagcagccg ccgcagcagg tggacaaggt     120
ggacaaggtc aaggaggata tggacaaggt tcaggaggtt ctgcagccgc cgccgccgcc     180
gcagcagcag cagcagctgc agcagctgga cgaggtcaag gaggatatgg tcaaggttct     240
ggaggtaatg ctgctgccgc agccgctgcc gccgccgccg ccgctgcagc agccggacag     300
ggaggtcaag gtggatatgg tagacaaagc caaggtgctg gttccgctgc tgctgctgct     360
gctgctgctg ccgctgctgc tgctgcagga tctggacaag gtggatacgg tggacaaggt     420
caaggaggtt atggtcagag tagtgcttct gcttcagctg ctgcgtcagc tgctagtact     480
gtagctaatt cggtgagtcg cctctcatcg ccttccgcag tatctcgagt tcttcagca     540 gtttctagct tggtttcaaa tggtcaagtg aatatggcag cgttacctaa tatcatttcc     600
aacatttctt cttctgtcag tgcatctgct cctggtgctt ctggatgtga ggtcatagtg     660
caagctctac tcgaagtcat cactgctctt gttcaaatcg ttagttcttc tagtgttgga     720
tatattaatc catctgctgt gaaccaaatt actaatgttg ttgctaatgc catggctcaa     780
gtaatgggc                                                            789

<210> SEQ ID NO 22
<211> LENGTH: 427
<212> TYPE: PRT
<213> ORGANISM: Artificial Sequence
<220> FEATURE:
<223> OTHER INFORMATION: Fusion protein

<400> SEQUENCE: 22

Gly Pro Asn Ser Ser Asp Pro Ser Lys Asp Ser Lys Ala Gln Val
1               5                   10                  15

Ser Ala Ala Glu Ala Gly Ile Thr Gly Thr Trp Tyr Asn Gln Leu Gly
                20                  25                  30

Ser Thr Phe Ile Val Thr Ala Gly Ala Asp Gly Ala Leu Thr Gly Thr
            35                  40                  45

Tyr Glu Ser Ala Val Gly Asn Ala Glu Ser Arg Tyr Thr Leu Thr Gly
        50                  55                  60

Arg Tyr Asp Ser Ala Pro Ala Thr Asp Gly Ser Gly Thr Ala Leu Gly
65                  70                  75                  80

Trp Arg Val Ala Trp Lys Asn Asn Tyr Arg Asn Ala His Ser Ala Thr
                85                  90                  95

Thr Trp Ser Gly Gln Tyr Val Gly Gly Ala Glu Ala Arg Ile Asn Thr
            100                 105                 110

Gln Trp Thr Leu Thr Ser Gly Thr Thr Glu Ala Asn Ala Trp Lys Ser
        115                 120                 125

Thr Leu Arg Gly His Asp Thr Phe Thr Lys Val Lys Pro Ser Ala Ala
```

```
Ser Ile Asp Ala Ala Lys Lys Ala Gly Val Asn Asn Gly Asn Pro Leu
145                 150                 155                 160

Asp Ala Val Gln Gln Gly Ile Gln Gly Gln Gly Gly Tyr Gly Gly Leu
            165                 170                 175

Gly Gln Gly Gly Tyr Gly Gln Gly Ala Gly Ser Ser Ala Ala Ala Ala
            180                 185                 190

Ala Ala Ala Ala Ala Ala Ala Ala Gly Gly Gln Gly Gly Gln Gly Gln
            195                 200                 205

Gly Gly Tyr Gly Gln Gly Ser Gly Gly Ser Ala Ala Ala Ala Ala Ala
            210                 215                 220

Ala Ala Ala Ala Ala Ala Ala Ala Gly Arg Gly Gln Gly Gly Tyr
225                 230                 235                 240

Gly Gln Gly Ser Gly Gly Asn Ala Ala Ala Ala Ala Ala Ala Ala Ala
            245                 250                 255

Ala Ala Ala Ala Ala Ala Gly Gln Gly Gly Gln Gly Gly Tyr Gly Arg
            260                 265                 270

Gln Ser Gln Gly Ala Gly Ser Ala Ala Ala Ala Ala Ala Ala Ala Ala
            275                 280                 285

Ala Ala Ala Ala Gly Ser Gly Gln Gly Gly Tyr Gly Gly Gln Gly
            290                 295                 300

Gln Gly Gly Tyr Gly Gln Ser Ser Ala Ser Ala Ser Ala Ala Ser
305                 310                 315                 320

Ala Ala Ser Thr Val Ala Asn Ser Val Ser Arg Leu Ser Ser Pro Ser
            325                 330                 335

Ala Val Ser Arg Val Ser Ser Ala Val Ser Ser Leu Val Ser Asn Gly
            340                 345                 350

Gln Val Asn Met Ala Ala Leu Pro Asn Ile Ile Ser Asn Ile Ser Ser
            355                 360                 365

Ser Val Ser Ala Ser Ala Pro Gly Ala Ser Gly Cys Glu Val Ile Val
            370                 375                 380

Gln Ala Leu Leu Glu Val Ile Thr Ala Leu Val Gln Ile Val Ser Ser
385                 390                 395                 400

Ser Ser Val Gly Tyr Ile Asn Pro Ser Ala Val Asn Gln Ile Thr Asn
            405                 410                 415

Val Val Ala Asn Ala Met Ala Gln Val Met Gly
            420                 425

<210> SEQ ID NO 23
<211> LENGTH: 1284
<212> TYPE: DNA
<213> ORGANISM: Artificial Sequence
<220> FEATURE:
<223> OTHER INFORMATION: Fusion protein

<400> SEQUENCE: 23
ggtccgaatt cgagctctga tccgagcaaa gatagcaaag cgcaggtgag cgcggcggaa      60
gcgggcatta ccggcacctg gtataaccag ctgggcagca cctttattgt gaccgcgggc     120
gcggatggcg cgctgaccgg cacctatgaa agcgcggtgg caacgcggaa agccgctat     180 accctgaccg gcgctatga tagcgcgccg gcgaccgatg gcagcggcac cgcgctgggc     240
tggcgcgtgg cgtggaaaaa caactatcgc aacgcgcata gcgcgaccac ctggagcggc     300
cagtatgtgg gcggcgcgga agcgcgcatt aacccccagt ggaccctgac cagcggcacc     360
accgaagcga acgcgtggaa aagcacctg cgcggccatg ataccttac caaagtgaaa     420
```

```
ccgagcgcgg cgagcattga tgcggcgaaa aaagcgggcg tgaacaacgg caacccgctg    480
gatgcggtgc agcagggat ccaaggtcaa ggtggatatg gtggactagg tcaaggagga    540
tatggacaag gtgcaggaag ttctgcagcc gctgccgccg ccgcagcagc cgccgcagca    600
ggtggacaag gtggacaagg tcaaggagga tatggacaag gttcaggagg ttctgcagcc    660
gccgccgccg ccgcagcagc agcagcagct gcagcagctg gacgaggtca aggaggatat    720
ggtcaaggtt ctggaggtaa tgctgctgcc gcagccgctg ccgccgccgc cgccgctgca    780
gcagccggac agggaggtca aggtggatat ggtagacaaa gccaaggtgc tggttccgct    840
gctgctgctg ctgctgctgc tgccgctgct gctgctgcag atctggaca aggtggatac    900 ggtggacaag gtcaaggagg ttatggtcag agtagtgctt ctgcttcagc tgctgcgtca    960
gctgctagta ctgtagctaa ttcggtgagt cgcctctcat cgccttccgc agtatctcga   1020
gtttcttcag cagtttctag cttggtttca atggtcaag tgaatatggc agcgttacct   1080
aatatcattt ccaacatttc ttcttctgtc agtgcatctg ctcctggtgc ttctggatgt   1140
gaggtcatag tgcaagctct actcgaagtc atcactgctc ttgttcaaat cgttagttct   1200
tctagtgttg atatattaa tccatctgct gtgaaccaaa ttactaatgt tgttgctaat   1260
gccatggctc aagtaatggg ctaa                                          1284
```

<210> SEQ ID NO 24
<211> LENGTH: 429
<212> TYPE: PRT
<213> ORGANISM: Artificial Sequence
<220> FEATURE:
<223> OTHER INFORMATION: Fusion protein

<400> SEQUENCE: 24

```
Gly Pro Asn Ser Ser Asp Pro Ser Lys Asp Ser Lys Ala Gln Val
1               5                   10                  15

Ser Ala Ala Glu Ala Gly Ile Thr Gly Thr Trp Tyr Asn Gln Leu Gly
            20                  25                  30

Ser Thr Phe Ile Val Thr Ala Gly Ala Asp Gly Ala Leu Thr Gly Thr
        35                  40                  45

Tyr Glu Ser Ala Val Gly Asn Ala Glu Ser Arg Tyr Thr Leu Thr Gly
    50                  55                  60

Arg Tyr Asp Ser Ala Pro Ala Thr Asp Gly Ser Gly Thr Ala Leu Gly
65                  70                  75                  80

Trp Arg Val Ala Trp Lys Asn Asn Tyr Arg Asn Ala His Ser Ala Thr
                85                  90                  95

Thr Trp Ser Gly Gln Tyr Val Gly Gly Ala Glu Ala Arg Ile Asn Thr
            100                 105                 110

Gln Trp Thr Leu Thr Ser Gly Thr Thr Glu Ala Asn Ala Trp Lys Ser
        115                 120                 125

Thr Leu Arg Gly His Asp Thr Phe Thr Lys Val Lys Pro Ser Ala Ala
    130                 135                 140

Ser Ile Asp Ala Ala Lys Lys Ala Gly Val Asn Asn Gly Asn Pro Leu
145                 150                 155                 160

Asp Ala Val Gln Gln Arg Ala Arg Ile Gln Gly Gln Gly Gly Tyr Gly
                165                 170                 175

Gly Leu Gly Gln Gly Gly Tyr Gly Gln Gly Ala Gly Ser Ser Ala Ala
            180                 185                 190

Ala Ala Ala Ala Ala Ala Ala Ala Ala Gly Gly Gln Gly Gly Gln
        195                 200                 205
```

```
Gly Gln Gly Gly Tyr Gly Gln Gly Ser Gly Gly Ser Ala Ala Ala
    210                 215                 220
Ala Ala Ala Ala Ala Ala Ala Ala Ala Gly Arg Gly Gln Gly
225                 230                 235                 240
Gly Tyr Gly Gln Gly Ser Gly Gly Asn Ala Ala Ala Ala Ala Ala
                245                 250                 255
Ala Ala Ala Ala Ala Ala Gly Gln Gly Gly Gln Gly Gly Tyr
            260                 265                 270
Gly Arg Gln Ser Gln Gly Ala Gly Ser Ala Ala Ala Ala Ala Ala
        275                 280                 285
Ala Ala Ala Ala Ala Gly Ser Gly Gln Gly Gly Tyr Gly Gly
            290                 295                 300
Gln Gly Gln Gly Gly Tyr Gly Gln Ser Ser Ala Ser Ala Ser Ala Ala
305                 310                 315                 320
Ala Ser Ala Ala Ser Thr Val Ala Asn Ser Val Ser Arg Leu Ser Ser
                325                 330                 335
Pro Ser Ala Val Ser Arg Val Ser Ser Ala Val Ser Ser Leu Val Ser
                340                 345                 350
Asn Gly Gln Val Asn Met Ala Ala Leu Pro Asn Ile Ile Ser Asn Ile
                355                 360                 365
Ser Ser Ser Val Ser Ala Ser Ala Pro Gly Ala Ser Gly Cys Glu Val
                370                 375                 380
Ile Val Gln Ala Leu Leu Glu Val Ile Thr Ala Leu Val Gln Ile Val
385                 390                 395                 400
Ser Ser Ser Ser Val Gly Tyr Ile Asn Pro Ser Ala Val Asn Gln Ile
                405                 410                 415
Thr Asn Val Val Ala Asn Ala Met Ala Gln Val Met Gly
                420                 425

<210> SEQ ID NO 25
<211> LENGTH: 1290
<212> TYPE: DNA
<213> ORGANISM: Artificial Sequence
<220> FEATURE:
<223> OTHER INFORMATION: Fusion protein

<400> SEQUENCE: 25
ggtccgaatt cgagctctga tccgagcaaa gatagcaaag cgcaggtgag cgcggcggaa      60
gcgggcatta ccggcacctg gtataaccag ctgggcagca cctttattgt gaccgcgggc     120
gcggatggcg cgctgaccgg cacctatgaa agcgcggtgg caacgcggaa agccgctat      180 accctgaccg ccgctatga tagcgcgccg cgaccgatg gcagcggcac cgcgctgggc      240
tggcgcgtgg cgtggaaaaa caactatcgc aacgcgcata gcgcgaccac ctggagcggc     300
cagtatgtgg gcggcgcgga agcgcgcatt aacacccagt ggaccctgac cagcggcacc     360
accgaagcga acgcgtggaa aagcaccctg cgcggccatg ataccttac caaagtgaaa      420 ccgagcgcgg cgagcattga tgcggcgaaa aaagcgggcg tgaacaacgg caacccctg      480 gatgcggtgc agcagcgagc tcggatccaa ggtcaaggtg gatatggtgg actaggtcaa     540
ggaggatatg gacaaggtgc aggaagttct gcagccgctg ccgccgccgc agcagccgcc     600
gcagcaggtg gacaaggtgg acaaggtcaa ggaggatatg gacaaggttc aggaggttct     660
gcagccgccg ccgccgccgc agcagcagca gcagctgcag cagctggacg aggtcaagga     720
ggatatggtc aaggttctgg aggtaatgct gctgccgcag ccgctgccgc cgccgccgcc     780
```

```
gctgcagcag ccggacaggg aggtcaaggt ggatatggta gacaaagcca aggtgctggt    840
tccgctgctg ctgctgctgc tgctgctgcc gctgctgctg ctgcaggatc tggacaaggt    900
ggatacggtg acaaggtca aggaggttat ggtcagagta gtgcttctgc ttcagctgct    960
gcgtcagctg ctagtactgt agctaattcg gtgagtcgcc tctcatcgcc ttccgcagta   1020
tctcgagttt cttcagcagt ttctagcttg gtttcaaatg gtcaagtgaa tatggcagcg   1080
ttacctaata tcatttccaa catttcttct tctgtcagtg catctgctcc tggtgcttct   1140
ggatgtgagg tcatagtgca agctctactc gaagtcatca ctgctcttgt tcaaatcgtt   1200
agttcttcta gtgttggata tattaatcca tctgctgtga accaaattac taatgttgtt   1260
gctaatgcca tggctcaagt aatgggctaa                                     1290
```

<210> SEQ ID NO 26
<211> LENGTH: 428
<212> TYPE: PRT
<213> ORGANISM: Artificial Sequence
<220> FEATURE:
<223> OTHER INFORMATION: Fusion protein

<400> SEQUENCE: 26

```
Gly Pro Asn Ser Gly Gln Gly Gly Tyr Gly Gly Leu Gly Gln Gly Gly
1               5                   10                  15

Tyr Gly Gln Gly Ala Gly Ser Ser Ala Ala Ala Ala Ala Ala Ala Ala
            20                  25                  30

Ala Ala Ala Ala Gly Gly Gln Gly Gly Gln Gly Gln Gly Gly Tyr Gly
        35                  40                  45

Gln Gly Ser Gly Gly Ser Ala Ala Ala Ala Ala Ala Ala Ala Ala Ala
    50                  55                  60

Ala Ala Ala Ala Ala Gly Arg Gly Gln Gly Gly Tyr Gly Gln Gly Ser
65                  70                  75                  80

Gly Gly Asn Ala Ala Ala Ala Ala Ala Ala Ala Ala Ala Ala Ala Ala
                85                  90                  95

Ala Ala Gly Gln Gly Gly Gln Gly Gly Tyr Gly Arg Gln Ser Gln Gly
            100                 105                 110

Ala Gly Ser Ala Ala Ala Ala Ala Ala Ala Ala Ala Ala Ala Ala Ala
        115                 120                 125

Ala Gly Ser Gly Gln Gly Gly Tyr Gly Gly Gln Gly Gln Gly Gly Tyr
    130                 135                 140

Gly Gln Ser Ser Ala Ser Ala Ser Ala Ala Ser Ala Ala Ser Thr
145                 150                 155                 160

Val Ala Asn Ser Val Ser Arg Leu Ser Ser Pro Ser Ala Val Ser Arg
                165                 170                 175

Val Ser Ser Ala Val Ser Ser Leu Val Ser Asn Gly Gln Val Asn Met
            180                 185                 190

Ala Ala Leu Pro Asn Ile Ile Ser Asn Ile Ser Ser Val Ser Ala
        195                 200                 205

Ser Ala Pro Gly Ala Ser Gly Cys Glu Val Ile Val Gln Ala Leu Leu
    210                 215                 220

Glu Val Ile Thr Ala Leu Val Gln Ile Val Ser Ser Ser Val Gly
225                 230                 235                 240

Tyr Ile Asn Pro Ser Ala Val Asn Gln Ile Thr Asn Val Val Ala Asn
                245                 250                 255

Ala Met Ala Gln Val Met Gly Gly Ser Ser Asp Pro Ser Lys Asp Ser
            260                 265                 270
```

```
Lys Ala Gln Val Ser Ala Ala Glu Ala Gly Ile Thr Gly Thr Trp Tyr
            275                 280                 285
Asn Gln Leu Gly Ser Thr Phe Ile Val Thr Ala Gly Ala Asp Gly Ala
        290                 295                 300
Leu Thr Gly Thr Tyr Glu Ser Ala Val Gly Asn Ala Glu Ser Arg Tyr
305                 310                 315                 320
Thr Leu Thr Gly Arg Tyr Asp Ser Ala Pro Ala Thr Asp Gly Ser Gly
                325                 330                 335
Thr Ala Leu Gly Trp Arg Val Ala Trp Lys Asn Asn Tyr Arg Asn Ala
            340                 345                 350
His Ser Ala Thr Thr Trp Ser Gly Gln Tyr Val Gly Gly Ala Glu Ala
        355                 360                 365
Arg Ile Asn Thr Gln Trp Thr Leu Thr Ser Gly Thr Thr Glu Ala Asn
370                 375                 380
Ala Trp Lys Ser Thr Leu Arg Gly His Asp Thr Phe Thr Lys Val Lys
385                 390                 395                 400
Pro Ser Ala Ala Ser Ile Asp Ala Ala Lys Lys Ala Gly Val Asn Asn
                405                 410                 415
Gly Asn Pro Leu Asp Ala Val Gln Gln Gly Ile Gln
            420                 425
```

<210> SEQ ID NO 27
<211> LENGTH: 1284
<212> TYPE: DNA
<213> ORGANISM: Artificial Sequence
<220> FEATURE:
<223> OTHER INFORMATION: Fusion protein

<400> SEQUENCE: 27

```
ggtccgaatt caggtcaagg tggatatggt ggactaggtc aaggaggata tggacaaggt    60
gcaggaagtt ctgcagccgc tgccgccgcc gcagcagccg ccgcagcagg tggacaaggt   120
ggacaaggtc aaggaggata tggacaaggt tcaggaggtt ctgcagccgc cgccgccgcc   180
gcagcagcag cagcagctgc agcagctgga cgaggtcaag gaggatatgg tcaaggttct   240
ggaggtaatg ctgctgccgc agccgctgcc gccgccgccg ccgctgcagc agccggacag   300
ggaggtcaag gtggatatgg tagacaaagc caaggtgctg gttccgctgc tgctgctgct   360
gctgctgctg ccgctgctgc tgctgcagga tctggacaag gtggatacgg tggacaaggt   420
caaggaggtt atggtcagag tagtgcttct gcttcagctg ctgcgtcagc tgctagtact   480
gtagctaatt cggtgagtcg cctctcatcg ccttccgcag tatctcgagt ttcttcagca   540
gtttctagct tggtttcaaa tggtcaagtg aatatggcag cgttacctaa tatcatttcc   600
aacatttctt cttctgtcag tgcatctgct cctggtgctt ctggatgtga ggtcatagtg   660
caagctctac tcgaagtcat cactgctctt gttcaaatcg ttagttcttc tagtgttgga   720
tatattaatc catctgctgt gaaccaaatt actaatgttg ttgctaatgc catggctcaa   780
gtaatgggcg ggagctctga tccgagcaaa gatagcaaag cgcaggtgag cgcggcggaa   840
gcgggcatta ccggcacctg gtataaccag ctgggcagca cctttattgt gaccgcgggc   900
gcggatggcg cgctgaccgg cacctatgaa agcgcggtgg gcaacgcgga aagccgctat   960
accctgaccg gcgctatga tagcgcgccg gcgaccgatg gcagcggcac cgcgctgggc  1020
tggcgcgtgg cgtggaaaaa caactatcgc aacgcgcata gcgcgaccac ctggagcggc  1080
cagtatgtgg gcggcgcgga agcgcgcatt aacacccagt ggaccctgac cagcggcacc  1140
accgaagcga acgcgtggaa aagcaccctg cgcggccatg ataccttttac caaagtgaaa  1200
```

```
ccgagcgcgg cgagcattga tgcggcgaaa aaagcgggcg tgaacaacgg caacccgctg    1260
gatgcggtgc agcaggggat ccaa                                           1284
```